US008535376B2

(12) United States Patent
Altmann

(10) Patent No.: US 8,535,376 B2
(45) Date of Patent: *Sep. 17, 2013

(54) ASPHERIC LENSES AND LENS FAMILY

(75) Inventor: Griffith E. Altmann, Pittsford, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 9 days.

This patent is subject to a terminal disclaimer.

(21) Appl. No.: 12/913,863

(22) Filed: Oct. 28, 2010

(65) Prior Publication Data
US 2011/0098810 A1 Apr. 28, 2011

Related U.S. Application Data

(63) Continuation of application No. 11/248,052, filed on Oct. 12, 2005, now Pat. No. 7,905,917, which is a continuation-in-part of application No. 11/057,278, filed on Feb. 11, 2005, now abandoned, which is a continuation-in-part of application No. 11/054,823, filed on Feb. 10, 2005, now abandoned, which is a continuation-in-part of application No. 10/703,884, filed on Nov. 7, 2003, now abandoned, which is a continuation-in-part of application No. 10/403,808, filed on Mar. 31, 2003, now abandoned.

(51) Int. Cl.
*A61F 2/16* (2006.01)
*G02C 7/10* (2006.01)

(52) U.S. Cl.
USPC .......................................... 623/6.23; 351/165

(58) Field of Classification Search
USPC ................................ 623/6.11–6.38; 351/165
See application file for complete search history.

(56) References Cited

U.S. PATENT DOCUMENTS 4,504,982 A 3/1985 Burk
4,710,193 A 12/1987 Volk
(Continued)

FOREIGN PATENT DOCUMENTS

EP 1424049 6/2004
WO WO 92/17134 10/1992
(Continued)

OTHER PUBLICATIONS

CVI Melles Griot Optics Guide—Spherical Aberration http://www.mellesgriot.com/products/optics/fo_3_2_1.htm.
(Continued)

*Primary Examiner* — Suzette J Gherbi
(74) *Attorney, Agent, or Firm* — Jeffrey B Powers

(57) ABSTRACT

In an embodiment, an aspheric IOL for use in a pseudophakic ocular system has no inherent spherical aberration. In an embodiment, an aspheric IOL for use in a pseudophakic ocular system has a controlled amount of inherent negative spherical aberration such that the IOL induces no spherical aberration in a converging wavefront from a cornea passing through the lens. An embodiment of the invention is directed to a family of aspheric IOLs made up of any two or more member aspheric IOLs each having different spherical aberration values and different lens shape factors. A lens constant, such as the well known A-constant, is kept constant throughout the family of lenses. An embodiment of the invention is directed to a multi-component accommodating intraocular lens (A-IOL). In a particular embodiment, the A-IOL introduces substantially no residual spherical aberration to a wavefront incident upon and passing through the A-IOL.

18 Claims, 45 Drawing Sheets

(56) References Cited

U.S. PATENT DOCUMENTS

| | | | |
|---|---|---|---|
| 4,720,286 A | 1/1988 | Bailey et al. | |
| 4,957,506 A | 9/1990 | Mercier | |
| 5,089,024 A | 2/1992 | Christie et al. | |
| 5,116,115 A | 5/1992 | Lange et al. | |
| 5,173,723 A | 12/1992 | Volk | |
| 5,178,636 A | 1/1993 | Silberman | |
| 5,191,366 A | 3/1993 | Kashiwagi | |
| 5,201,762 A | 4/1993 | Hauber | |
| 5,275,623 A | 1/1994 | Sarfarazi | |
| 5,282,852 A * | 2/1994 | Capetan et al. | 623/6.11 |
| 5,384,606 A | 1/1995 | Koch et al. | |
| 5,443,507 A | 8/1995 | Jacobi | |
| 5,760,871 A | 6/1998 | Kosoburd et al. | |
| 5,800,532 A | 9/1998 | Liberman | |
| 6,089,711 A | 7/2000 | Blankenbecler et al. | |
| 6,113,633 A | 9/2000 | Portney | |
| 6,210,005 B1 | 4/2001 | Portney | |
| 6,224,211 B1 | 5/2001 | Gordon | |
| 6,423,094 B1 | 7/2002 | Sarfarazi | |
| 6,428,573 B2 | 8/2002 | Barnett | |
| 6,474,814 B1 * | 11/2002 | Griffin | 351/159.41 |
| 6,488,708 B2 | 12/2002 | Sarfarazi | |
| 6,554,425 B1 | 4/2003 | Roffman et al. | |
| 6,609,793 B2 * | 8/2003 | Norrby et al. | 351/212 |
| 6,808,265 B2 | 10/2004 | Cox | |
| 6,830,332 B2 * | 12/2004 | Piers et al. | 351/159.11 |
| 6,858,040 B2 | 2/2005 | Nguyen | |
| 6,884,261 B2 * | 4/2005 | Zadno-Azizi et al. | 623/6.12 |
| 6,884,263 B2 | 4/2005 | Valyunin et al. | |
| 6,902,577 B2 | 6/2005 | Lipshitz et al. | |
| 6,935,743 B2 | 8/2005 | Shadduck | |
| 7,048,759 B2 | 5/2006 | Bogaert et al. | |
| 7,137,702 B2 | 11/2006 | Piers et al. | |
| 7,182,780 B2 | 2/2007 | Terwee et al. | |
| 7,198,640 B2 | 4/2007 | Nguyen | |
| 7,241,311 B2 | 7/2007 | Norrby et al. | |
| 7,264,351 B2 | 9/2007 | Shadduck | |
| 7,377,641 B2 | 5/2008 | Piers et al. | |
| 7,381,221 B2 * | 6/2008 | Lang et al. | 623/6.24 |
| 7,662,179 B2 | 2/2010 | Sarfarazi | |
| 7,841,720 B2 | 11/2010 | Norrby et al. | |
| 7,905,917 B2 * | 3/2011 | Altmann | 623/6.23 |
| 2004/0015236 A1 | 1/2004 | Sarfarazi | |
| 2004/0156014 A1 * | 8/2004 | Piers et al. | 351/168 |

FOREIGN PATENT DOCUMENTS

| | | |
|---|---|---|
| WO | WO 93/03686 | 3/1993 |
| WO | WO 94/11765 | 5/1994 |
| WO | WO 00/61036 | 10/2000 |
| WO | WO 01/98424 | 11/2001 |
| WO | WO 02/071983 | 9/2002 |
| WO | WO 2004/090611 | 10/2004 |
| WO | WO 2005/046527 | 5/2005 |

OTHER PUBLICATIONS

Taketani et al., "Influence of intraocular lens tilt and decentration on wavefront aberrations," J Cataract Refract Surg, Oct. 2004, (vol. 30), (pp. 2158-2162).

Wang et al., "Effect of decentration of wavefront-corrected intraocular lens on the higher-order aberrations of the eye," Arch Ophthalmol, Sep. 2005, (vol. 123), (pp. 1226-1230).

Altmann et al., "Optical performance of 3 intraocular lens designs in the presence of decentration," J cataract Refract Surg, Mar. 2005, (vol. 31), (pp. 574-585).

Oshika et al., "Influence of tilt and decentration of scleral-sutured intraocular lens on ocular higher-order wavefront aberration," Br J Ophthalmol, 2007, (vol. 91), (pp. 185-188).

Bellucci et al., "Spherical aberration and coma with an aspherical and a spherical intraocular lens in normal age-matched eyes," J Cataract Refract Surg., Feb. 2007, (vol. 33), (pp. 203-209).

Geary, "Aberrations induced by decenration," Introduction to Lens Design, Chapter 37, subsec. 37.7, 2002, Willmann-Bell (Richmond Virginia) (p. 426-430).

Hecht, "Aberrations," Optics, Chapter 6, subsec. 6.3, 1990, $2^{nd}$ ed., Addison-Wesley (Reading, Massachusetts), (pp. 220-237).

International Search Report (PCT/ISA/210) and Written Opinion (PCT/ISA/237) mailed on Oct. 14, 2004, regarding U.S. Appl. No. 10/703,884.

International Search Report (PCT/ISA/210) and Written Opinion (PCT/ISA/237) mailed on Dec. 20, 2005, regarding U.S. Appl. No. 11/057,278.

\* cited by examiner

EQUICONVEX SPHERICAL LENS FAMILY
Nm = 1.427   Na = 1.336

| Power (diopter) | Rx (mm) | Rp (mm) | CT (mm) | ET (mm) | E2H2 (mm) (Y/Fig 13) | Effect of H2 Position (diopter) | SA(D) Equi-convex sphere (diopter) (Y/Fig 12) | Effect of SA (diopter) | A-const Delta Equiconvex (dipter) |
|---|---|---|---|---|---|---|---|---|---|
| 10 | 18.174 | -18.174 | 0.799 | 0.300 | -0.125 | -0.008 | 0.020 | 0.140 | 0.132 |
| 10.5 | 17.307 | -17.307 | 0.824 | 0.300 | -0.124 | -0.008 | 0.023 | 0.137 | 0.128 |
| 11 | 16.518 | -16.518 | 0.849 | 0.300 | -0.124 | -0.008 | 0.026 | 0.133 | 0.125 |
| 11.5 | 15.798 | -15.798 | 0.875 | 0.300 | -0.123 | -0.008 | 0.030 | 0.129 | 0.121 |
| 12 | 15.138 | -15.138 | 0.900 | 0.300 | -0.122 | -0.008 | 0.034 | 0.125 | 0.117 |
| 12.5 | 14.530 | -14.530 | 0.926 | 0.300 | -0.121 | -0.008 | 0.039 | 0.121 | 0.113 |
| 13 | 13.970 | -13.970 | 0.952 | 0.300 | -0.121 | -0.008 | 0.044 | 0.116 | 0.106 |
| 13.5 | 13.450 | -13.450 | 0.978 | 0.300 | -0.120 | -0.008 | 0.049 | 0.111 | 0.103 |
| 14 | 12.968 | -12.968 | 1.004 | 0.300 | -0.119 | -0.007 | 0.054 | 0.105 | 0.098 |
| 14.5 | 12.519 | -12.519 | 1.030 | 0.300 | -0.118 | -0.007 | 0.060 | 0.099 | 0.092 |
| 15 | 12.100 | -12.100 | 1.058 | 0.300 | -0.118 | -0.007 | 0.067 | 0.093 | 0.088 |
| 15.5 | 11.707 | -11.707 | 1.082 | 0.300 | -0.117 | -0.006 | 0.074 | 0.086 | 0.079 |
| 16 | 11.340 | -11.340 | 1.108 | 0.300 | -0.116 | -0.006 | 0.081 | 0.078 | 0.072 |
| 16.5 | 10.994 | -10.994 | 1.134 | 0.300 | -0.116 | -0.005 | 0.089 | 0.070 | 0.065 |
| 17 | 10.669 | -10.669 | 1.161 | 0.300 | -0.115 | -0.005 | 0.098 | 0.062 | 0.057 |
| 17.5 | 10.362 | -10.362 | 1.188 | 0.300 | -0.114 | -0.004 | 0.107 | 0.053 | 0.049 |
| 18 | 10.072 | -10.072 | 1.214 | 0.300 | -0.113 | -0.003 | 0.116 | 0.043 | 0.040 |
| 18.5 | 9.798 | -9.798 | 1.241 | 0.300 | -0.113 | -0.002 | 0.126 | 0.033 | 0.031 |
| 19 | 9.538 | -9.538 | 1.268 | 0.300 | -0.112 | -0.002 | 0.137 | 0.023 | 0.021 |
| 19.5 | 9.292 | -9.292 | 1.295 | 0.300 | -0.111 | -0.001 | 0.148 | 0.012 | 0.011 |
| 20 | 9.058 | -9.058 | 1.322 | 0.300 | -0.111 | 0.000 | 0.160 | 0.000 | 0.000 |
| 20.5 | 8.835 | -8.835 | 1.350 | 0.300 | -0.110 | 0.001 | 0.172 | -0.012 | -0.011 |
| 21 | 8.623 | -8.623 | 1.377 | 0.300 | -0.109 | 0.002 | 0.185 | -0.025 | -0.023 |
| 21.5 | 8.420 | -8.420 | 1.405 | 0.300 | -0.109 | 0.003 | 0.198 | -0.039 | -0.036 |
| 22 | 8.227 | -8.227 | 1.433 | 0.300 | -0.108 | 0.004 | 0.213 | -0.053 | -0.049 |
| 22.5 | 8.042 | -8.042 | 1.461 | 0.300 | -0.107 | 0.005 | 0.228 | -0.068 | -0.063 |
| 23 | 7.865 | -7.865 | 1.489 | 0.300 | -0.107 | 0.006 | 0.243 | -0.084 | -0.077 |
| 23.5 | 7.696 | -7.696 | 1.518 | 0.300 | -0.106 | 0.007 | 0.259 | -0.100 | -0.093 |
| 24 | 7.534 | -7.534 | 1.546 | 0.300 | -0.105 | 0.009 | 0.276 | -0.117 | -0.108 |
| 24.5 | 7.378 | -7.378 | 1.575 | 0.300 | -0.105 | 0.010 | 0.294 | -0.135 | -0.125 |
| 25 | 7.228 | -7.228 | 1.604 | 0.300 | -0.104 | 0.011 | 0.313 | -0.153 | -0.142 |
| 25.5 | 7.085 | -7.085 | 1.633 | 0.300 | -0.104 | 0.012 | 0.332 | -0.172 | -0.160 |
| 26 | 6.947 | -6.947 | 1.662 | 0.300 | -0.103 | 0.014 | 0.352 | -0.192 | -0.179 |
| 26.5 | 6.814 | -6.814 | 1.692 | 0.300 | -0.102 | 0.015 | 0.373 | -0.213 | -0.198 |
| 27 | 6.685 | -6.685 | 1.722 | 0.300 | -0.102 | 0.017 | 0.394 | -0.235 | -0.218 |
| 27.5 | 6.562 | -6.562 | 1.752 | 0.300 | -0.101 | 0.018 | 0.417 | -0.257 | -0.239 |
| 28 | 6.443 | -6.443 | 1.782 | 0.300 | -0.101 | 0.020 | 0.440 | -0.280 | -0.261 |
| 28.5 | 6.328 | -6.328 | 1.813 | 0.300 | -0.100 | 0.021 | 0.484 | -0.305 | -0.284 |
| 29 | 6.217 | -6.217 | 1.844 | 0.300 | -0.099 | 0.023 | 0.489 | -0.330 | -0.307 |
| 29.5 | 6.109 | -6.109 | 1.875 | 0.300 | -0.099 | 0.024 | 0.515 | -0.355 | -0.331 |
| 30 | 6.005 | -6.005 | 1.906 | 0.300 | -0.098 | 0.026 | 0.542 | -0.382 | -0.356 |

FIG. 20

BIOCONVEX SPHERICAL LENS FAMILY
Nm = 1.427   Na = 1.336

| Power (diopter) | Ra (mm) | Rp (mm) | CT (mm) | ET (mm) | E2H2 (mm) (Y/Fig 13) | Biconvex (Ra:Rp=1:2) (diopter) | Power Delta Equi-convex Sphere (diopter) (Y/Fig 11) |
|---|---|---|---|---|---|---|---|
| 10 | 13.633 | -27.266 | 0.800 | 0.300 | -0.334 | 0.095 | -0.036 |
| 10.5 | 12.982 | -25.965 | 0.825 | 0.300 | -0.342 | 0.097 | -0.032 |
| 11 | 12.391 | -24.782 | 0.851 | 0.300 | -0.350 | 0.098 | -0.027 |
| 11.5 | 11.851 | -23.702 | 0.877 | 0.300 | -0.357 | 0.098 | -0.023 |
| 12 | 11.356 | -22.712 | 0.902 | 0.300 | -0.365 | 0.098 | -0.019 |
| 12.5 | 10.900 | -21.800 | 0.928 | 0.300 | -0.373 | 0.097 | -0.016 |
| 13 | 10.480 | -20.959 | 0.954 | 0.300 | -0.381 | 0.095 | -0.013 |
| 13.5 | 10.090 | -20.180 | 0.981 | 0.300 | -0.389 | 0.093 | -0.010 |
| 14 | 9.729 | -19.457 | 1.007 | 0.300 | -0.397 | 0.090 | -0.007 |
| 14.5 | 9.392 | -18.784 | 1.033 | 0.300 | -0.405 | 0.087 | -0.005 |
| 15 | 9.077 | -18.155 | 1.060 | 0.300 | -0.413 | 0.083 | -0.003 |
| 15.5 | 8.783 | -17.567 | 1.086 | 0.300 | -0.422 | 0.078 | -0.002 |
| 16 | 8.508 | -17.015 | 1.113 | 0.300 | -0.430 | 0.072 | 0.000 |
| 16.5 | 8.248 | -16.497 | 1.140 | 0.300 | -0.439 | 0.066 | 0.001 |
| 17 | 8.005 | -16.009 | 1.167 | 0.300 | -0.447 | 0.059 | 0.001 |
| 17.5 | 7.775 | -15.549 | 1.194 | 0.300 | -0.456 | 0.051 | 0.002 |
| 18 | 7.557 | -15.115 | 1.222 | 0.300 | -0.464 | 0.042 | 0.002 |
| 18.5 | 7.352 | -14.703 | 1.249 | 0.300 | -0.473 | 0.033 | 0.002 |
| 19 | 7.157 | -14.314 | 1.277 | 0.300 | -0.482 | 0.023 | 0.002 |
| 19.5 | 6.972 | -13.944 | 1.305 | 0.300 | -0.491 | 0.012 | 0.001 |
| 20 | 6.797 | -13.593 | 1.333 | 0.300 | -0.500 | 0.000 | 0.000 |
| 20.5 | 6.629 | -13.259 | 1.361 | 0.300 | -0.510 | -0.013 | -0.001 |
| 21 | 6.470 | -12.941 | 1.390 | 0.300 | -0.519 | -0.026 | -0.003 |
| 21.5 | 6.319 | -12.637 | 1.419 | 0.300 | -0.529 | -0.041 | -0.005 |
| 22 | 6.174 | -12.347 | 1.448 | 0.300 | -0.538 | -0.056 | -0.007 |
| 22.5 | 6.035 | -12.070 | 1.477 | 0.300 | -0.548 | -0.072 | -0.009 |
| 23 | 5.903 | -11.805 | 1.507 | 0.300 | -0.558 | -0.090 | -0.012 |
| 23.5 | 5.776 | -11.551 | 1.537 | 0.300 | -0.568 | -0.108 | -0.015 |
| 24 | 5.654 | -11.308 | 1.567 | 0.300 | -0.578 | -0.127 | -0.019 |
| 24.5 | 5.537 | -11.075 | 1.597 | 0.300 | -0.589 | -0.148 | -0.023 |
| 25 | 5.425 | -10.850 | 1.628 | 0.300 | -0.600 | -0.169 | -0.027 |
| 25.5 | 5.317 | -10.635 | 1.659 | 0.300 | -0.610 | -0.192 | -0.032 |
| 26 | 5.214 | -10.428 | 1.690 | 0.300 | -0.622 | -0.216 | -0.037 |
| 26.5 | 5.114 | -10.228 | 1.722 | 0.300 | -0.633 | -0.241 | -0.043 |
| 27 | 5.018 | -10.036 | 1.754 | 0.300 | -0.644 | -0.267 | -0.049 |
| 27.5 | 4.925 | -9.851 | 1.787 | 0.300 | -0.656 | -0.295 | -0.056 |
| 28 | 4.836 | -9.672 | 1.820 | 0.300 | -0.668 | -0.324 | -0.063 |
| 28.5 | 4.750 | -9.499 | 1.853 | 0.300 | -0.680 | -0.355 | -0.071 |
| 29 | 4.666 | -9.333 | 1.887 | 0.300 | -0.693 | -0.387 | -0.080 |
| 29.5 | 4.586 | -9.172 | 1.922 | 0.300 | -0.706 | -0.421 | -0.089 |
| 30 | 4.508 | -9.016 | 1.957 | 0.300 | -0.719 | -0.456 | -0.099 |

FIG. 21

BIOCONVEX ASPHERICAL LENS FAMILY
Nm = 1.427   Na = 1.336   SA = 0   Ka = Kp = 0.97799

| Power (diopter) | Ra (mm) | Rp (mm) | CT (mm) | ET (mm) | E2H2 (mm) (Y/Fig 13) | Effect of H2 Position (diopter) | Biconvex (Ra:Rp=1:2) (diopter) | Power Delta Equi-convex Sphere (diopter) (Y/Fig 11) |
|---|---|---|---|---|---|---|---|---|
| 10 | 13.633 | -27.266 | 0.795 | 0.300 | -0.332 | 0.085 | 0.180 | -0.047 |
| 10.5 | 12.983 | -25.965 | 0.820 | 0.300 | -0.339 | 0.086 | 0.182 | -0.043 |
| 11 | 12.391 | -24.782 | 0.845 | 0.300 | -0.347 | 0.086 | 0.183 | -0.039 |
| 11.5 | 11.851 | -23.702 | 0.870 | 0.300 | -0.354 | 0.086 | 0.183 | -0.035 |
| 12 | 11.356 | -22.712 | 0.895 | 0.300 | -0.361 | 0.086 | 0.182 | -0.031 |
| 12.5 | 10.900 | -21.801 | 0.919 | 0.300 | -0.368 | 0.085 | 0.180 | -0.028 |
| 13 | 10.480 | -20.960 | 0.944 | 0.300 | -0.376 | 0.083 | 0.176 | -0.025 |
| 13.5 | 10.090 | -20.181 | 0.969 | 0.300 | -0.383 | 0.081 | 0.171 | -0.022 |
| 14 | 9.729 | -19.458 | 0.994 | 0.300 | -0.391 | 0.078 | 0.165 | -0.020 |
| 14.5 | 9.392 | -18.784 | 1.019 | 0.300 | -0.398 | 0.075 | 0.158 | -0.017 |
| 15 | 9.078 | -18.156 | 1.044 | 0.300 | -0.405 | 0.071 | 0.150 | -0.015 |
| 15.5 | 8.764 | -17.567 | 1.069 | 0.300 | -0.413 | 0.066 | 0.140 | -0.013 |
| 16 | 8.508 | -17.016 | 1.094 | 0.300 | -0.420 | 0.061 | 0.130 | -0.011 |
| 16.5 | 8.249 | -16.498 | 1.119 | 0.300 | -0.427 | 0.056 | 0.118 | -0.009 |
| 17 | 8.005 | -16.010 | 1.144 | 0.300 | -0.435 | 0.049 | 0.104 | -0.008 |
| 17.5 | 7.775 | -15.550 | 1.169 | 0.300 | -0.442 | 0.043 | 0.090 | -0.006 |
| 18 | 7.558 | -15.116 | 1.194 | 0.300 | -0.450 | 0.035 | 0.074 | -0.005 |
| 18.5 | 7.352 | -14.705 | 1.219 | 0.300 | -0.457 | 0.027 | 0.058 | -0.004 |
| 19 | 7.158 | -14.315 | 1.244 | 0.300 | -0.465 | 0.019 | 0.040 | -0.002 |
| 19.5 | 6.973 | -13.946 | 1.269 | 0.300 | -0.472 | 0.010 | 0.020 | -0.001 |
| 20 | 6.797 | -13.595 | 1.294 | 0.300 | -0.480 | 0.000 | 0.000 | 0.000 |
| 20.5 | 6.630 | -13.261 | 1.319 | 0.300 | -0.487 | -0.010 | -0.022 | 0.001 |
| 21 | 6.471 | -12.943 | 1.344 | 0.300 | -0.495 | -0.021 | -0.045 | 0.002 |
| 21.5 | 6.320 | -12.639 | 1.369 | 0.300 | -0.502 | -0.033 | -0.069 | 0.003 |
| 22 | 6.175 | -12.350 | 1.394 | 0.300 | -0.510 | -0.045 | -0.094 | 0.005 |
| 22.5 | 6.036 | -12.073 | 1.419 | 0.300 | -0.517 | -0.057 | -0.121 | 0.006 |
| 23 | 5.904 | -11.808 | 1.445 | 0.300 | -0.525 | -0.071 | -0.149 | 0.007 |
| 23.5 | 5.777 | -11.554 | 1.470 | 0.300 | -0.533 | -0.084 | -0.178 | 0.008 |
| 24 | 5.656 | -11.311 | 1.495 | 0.300 | -0.540 | -0.099 | -0.208 | 0.009 |
| 24.5 | 5.539 | -11.078 | 1.520 | 0.300 | -0.548 | -0.114 | -0.240 | 0.011 |
| 25 | 5.427 | -10.854 | 1.545 | 0.300 | -0.556 | -0.130 | -0.272 | 0.012 |
| 25.5 | 5.319 | -10.639 | 1.571 | 0.300 | -0.563 | -0.146 | -0.306 | 0.014 |
| 26 | 5.216 | -10.432 | 1.596 | 0.300 | -0.571 | -0.163 | -0.342 | 0.016 |
| 26.5 | 5.116 | -10.232 | 1.621 | 0.300 | -0.579 | -0.180 | -0.378 | 0.018 |
| 27 | 5.020 | -10.041 | 1.647 | 0.300 | -0.587 | -0.198 | -0.416 | 0.020 |
| 27.5 | 4.928 | -9.856 | 1.672 | 0.300 | -0.594 | -0.217 | -0.455 | 0.022 |
| 28 | 4.839 | -9.677 | 1.697 | 0.300 | -0.602 | -0.236 | -0.496 | 0.024 |
| 28.5 | 4.753 | -9.505 | 1.723 | 0.300 | -0.610 | -0.256 | -0.538 | 0.027 |
| 29 | 4.669 | -9.339 | 1.748 | 0.300 | -0.618 | -0.277 | -0.581 | 0.030 |
| 29.5 | 4.589 | -9.178 | 1.773 | 0.300 | -0.626 | -0.298 | -0.625 | 0.033 |
| 30 | 4.511 | -9.023 | 1.799 | 0.300 | -0.633 | -0.320 | -0.670 | 0.036 |

FIG. 22

EQUICONVEX ASPHERE LENS FAMILY
Nm = 1.427  Na = 1.336  SA = 0  Ka = Kp = 1.16133  SA = 0

| Power (diopter) | Ra (mm) | Rp (mm) | CT (mm) | ET (mm) | E2H2 (mm) | Effect of H2 Position | Equiconic (Ra:Rp=1:1) | Power Delta Equi-convex Sphere (Y/Fig 11) |
|---|---|---|---|---|---|---|---|---|
| 10 | 18.175 | -18.175 | 0.795 | 0.300 | 0.125 | -0.008 | -0.008 | -0.139 |
| 10.5 | 17.307 | -17.307 | 0.819 | 0.300 | 0.124 | -0.008 | -0.008 | -0.136 |
| 11 | 16.518 | -16.518 | 0.844 | 0.300 | 0.124 | -0.008 | -0.008 | -0.133 |
| 11.5 | 15.798 | -15.798 | 0.869 | 0.300 | 0.123 | -0.008 | -0.008 | -0.129 |
| 12 | 15.138 | -15.138 | 0.894 | 0.300 | 0.122 | -0.008 | -0.008 | -0.125 |
| 12.5 | 14.531 | -14.531 | 0.918 | 0.300 | 0.122 | -0.008 | -0.008 | -0.120 |
| 13 | 13.970 | -13.970 | 0.943 | 0.300 | 0.121 | -0.007 | -0.007 | -0.115 |
| 13.5 | 13.451 | -13.451 | 0.968 | 0.300 | 0.120 | -0.007 | -0.007 | -0.110 |
| 14 | 12.968 | -12.968 | 0.993 | 0.300 | 0.119 | -0.007 | -0.007 | -0.105 |
| 14.5 | 12.519 | -12.519 | 1.017 | 0.300 | 0.119 | -0.007 | -0.007 | -0.099 |
| 15 | 12.100 | -12.100 | 1.042 | 0.300 | 0.118 | -0.006 | -0.006 | -0.092 |
| 15.5 | 11.708 | -11.708 | 1.067 | 0.300 | 0.117 | -0.006 | -0.006 | -0.085 |
| 16 | 11.340 | -11.340 | 1.091 | 0.300 | 0.117 | -0.005 | -0.005 | -0.078 |
| 16.5 | 10.995 | -10.995 | 1.116 | 0.300 | 0.116 | -0.005 | -0.005 | -0.070 |
| 17 | 10.669 | -10.669 | 1.141 | 0.300 | 0.115 | -0.004 | -0.004 | -0.061 |
| 17.5 | 10.363 | -10.363 | 1.166 | 0.300 | 0.115 | -0.004 | -0.004 | -0.053 |
| 18 | 10.073 | -10.073 | 1.190 | 0.300 | 0.114 | -0.003 | -0.003 | -0.043 |
| 18.5 | 9.799 | -9.799 | 1.215 | 0.300 | 0.114 | -0.002 | -0.002 | -0.033 |
| 19 | 9.539 | -9.539 | 1.240 | 0.300 | 0.113 | -0.002 | -0.002 | -0.023 |
| 19.5 | 9.293 | -9.293 | 1.264 | 0.300 | 0.112 | -0.001 | -0.001 | -0.012 |
| 20 | 9.059 | -9.059 | 1.289 | 0.300 | 0.112 | 0.000 | 0.000 | 0.000 |
| 20.5 | 8.836 | -8.836 | 1.314 | 0.300 | 0.111 | 0.001 | 0.001 | 0.012 |
| 21 | 8.624 | -8.624 | 1.339 | 0.300 | 0.110 | 0.002 | 0.002 | 0.025 |
| 21.5 | 8.421 | -8.421 | 1.363 | 0.300 | 0.110 | 0.003 | 0.003 | 0.039 |
| 22 | 8.228 | -8.228 | 1.388 | 0.300 | 0.109 | 0.004 | 0.004 | 0.053 |
| 22.5 | 8.044 | -8.044 | 1.413 | 0.300 | 0.109 | 0.005 | 0.005 | 0.067 |
| 23 | 7.867 | -7.867 | 1.437 | 0.300 | 0.108 | 0.005 | 0.005 | 0.083 |
| 23.5 | 7.698 | -7.698 | 1.462 | 0.300 | 0.108 | 0.007 | 0.007 | 0.099 |
| 24 | 7.536 | -7.536 | 1.487 | 0.300 | 0.107 | 0.008 | 0.008 | 0.116 |
| 24.5 | 7.380 | -7.380 | 1.511 | 0.300 | 0.106 | 0.009 | 0.009 | 0.133 |
| 25 | 7.231 | -7.231 | 1.536 | 0.300 | 0.106 | 0.010 | 0.010 | 0.152 |
| 25.5 | 7.087 | -7.087 | 1.561 | 0.300 | 0.105 | 0.011 | 0.011 | 0.171 |
| 26 | 6.949 | -6.949 | 1.588 | 0.300 | 0.105 | 0.012 | 0.012 | 0.191 |
| 26.5 | 6.816 | -6.816 | 1.610 | 0.300 | 0.104 | 0.013 | 0.013 | 0.211 |
| 27 | 6.688 | -6.688 | 1.635 | 0.300 | 0.104 | 0.014 | 0.014 | 0.233 |
| 27.5 | 6.565 | -6.565 | 1.660 | 0.300 | 0.103 | 0.016 | 0.016 | 0.255 |
| 28 | 6.446 | -6.446 | 1.684 | 0.300 | 0.103 | 0.017 | 0.017 | 0.278 |
| 28.5 | 6.331 | -6.331 | 1.709 | 0.300 | 0.102 | 0.018 | 0.018 | 0.302 |
| 29 | 6.220 | -6.220 | 1.734 | 0.300 | 0.102 | 0.019 | 0.019 | 0.326 |
| 29.5 | 6.113 | -6.113 | 1.758 | 0.300 | 0.102 | 0.021 | 0.021 | 0.352 |
| 30 | 6.009 | -6.009 | 1.783 | 0.300 | 0.101 | 0.022 | 0.022 | 0.378 |

FIG. 23

(15-D) A-IOL 600-4

| Surface | Radius | Conic Constant | Center Thickness (mm) | Edge Thickness $E_T$ (mm) | Lens Volume (cc) | Refractive Index |
|---|---|---|---|---|---|---|
| 1 | 4.5178 | -0.1423 | 1.6160 | 0.2 | .022 | 1.425 |
| 2 | -7.8227 | 0 | --- | --- | --- | 1.336 |
| 3 | -5.2293 | 0 | 0.2 | 0.8174 | .013 | 1.425 |
| 4 | -200 | 0 | --- | --- | --- | 1.336 |

Fig. 29D

(20-D) A-IOL 600-3

| Surface | Radius | Conic Constant | Center Thickness (mm) | Edge Thickness $E_T$ (mm) | Lens Volume (cc) | Refractive Index |
|---|---|---|---|---|---|---|
| 1 | 4.4343 | -0.4438 | 1.6079 | 0.2 | .022 | 1.425 |
| 2 | -7.7561 | 0 | --- | --- | --- | 1.336 |
| 3 | -6.1654 | 0 | 0.4 | 0.8182 | .015 | 1.425 |
| 4 | -33.9942 | 0 | --- | --- | --- | 1.336 |

Fig. 29C

(25-D) A-IOL 600-2

| Surface | Radius | Conic Constant | Center Thickness (mm) | Edge Thickness $E_T$ (mm) | Lens Volume (cc) | Refractive Index |
|---|---|---|---|---|---|---|
| 1 | 5.0422 | -1.3440 | 1.5863 | 0.2 | .021 | 1.425 |
| 2 | -6.1031 | 0 | --- | --- | --- | 1.336 |
| 3 | -7.2250 | 0 | 0.4 | 0.6289 | .013 | 1.425 |
| 4 | -17.5031 | 0 | --- | --- | --- | 1.336 |

Fig. 29B

(30-D) A-IOL 600-1

| Surface | Radius | Conic Constant | Center Thickness (mm) | Edge Thickness $E_T$ (mm) | Lens Volume (cc) | Refractive Index |
|---|---|---|---|---|---|---|
| 1 | 5.4768 | -3.0400 | 1.5778 | 0.2 | .021 | 1.425 |
| 2 | -5.3628 | 0 | --- | --- | --- | 1.336 |
| 3 | -8.6642 | 0 | 0.4 | 0.4383 | .011 | 1.425 |
| 4 | -11.6142 | 0 | --- | --- | --- | 1.336 |

Fig. 29A

Surface (3) Values

| | 15 D | 20 D | 25 D | 30 D |
|---|---|---|---|---|
| Vertix Radius | 4.590161 | 6.506186 | 9.480051 | 20.33516 |
| Conic Constant | -1.335691 | -0.02292 | 0.266577 | 15 |

Surface (3) Sag Values

| Radial Coordinate of Optical Zone | 15 D | 20 D | 25 D | 30 D |
|---|---|---|---|---|
| 0 | 0 | 0 | 0 | 0 |
| 0.01 | 1.09E-05 | 7.68E-06 | 5.27E-06 | 2.46E-06 |
| 0.02 | 4.36E-05 | 3.07E-05 | 2.11E-05 | 9.84E-06 |
| 0.03 | 9.8E-05 | 6.92E-05 | 4.75E-05 | 2.21E-05 |
| 0.04 | 0.000174 | 0.000123 | 8.44E-05 | 3.93E-05 |
| 0.05 | 0.000272 | 0.000192 | 0.000132 | 6.15E-05 |
| 0.06 | 0.000392 | 0.000277 | 0.00019 | 8.85E-05 |
| 0.07 | 0.000534 | 0.000377 | 0.000258 | 0.00012 |
| 0.08 | 0.000697 | 0.000492 | 0.000338 | 0.000157 |
| 0.09 | 0.000882 | 0.000623 | 0.000427 | 0.000199 |
| 0.1 | 0.001089 | 0.000769 | 0.000527 | 0.000246 |
| 0.11 | 0.001318 | 0.000931 | 0.000638 | 0.000298 |
| 0.12 | 0.001568 | 0.001107 | 0.00076 | 0.000354 |
| 0.13 | 0.001841 | 0.001299 | 0.000891 | 0.000416 |
| 0.14 | 0.002135 | 0.001506 | 0.001034 | 0.000482 |
| 0.15 | 0.002451 | 0.001729 | 0.001187 | 0.000553 |
| 0.16 | 0.002788 | 0.001968 | 0.00135 | 0.00063 |
| 0.17 | 0.003148 | 0.002221 | 0.001524 | 0.000711 |
| 0.18 | 0.003529 | 0.00249 | 0.001709 | 0.000797 |
| 0.19 | 0.003932 | 0.002775 | 0.001904 | 0.000888 |
| 0.2 | 0.004356 | 0.003075 | 0.002326 | 0.000984 |
| 0.21 | 0.004803 | 0.00339 | 0.002553 | 0.001085 |
| 0.22 | 0.005271 | 0.003721 | 0.002553 | 0.001191 |
| 0.23 | 0.005761 | 0.004067 | 0.002791 | 0.001301 |
| 0.24 | 0.006273 | 0.004428 | 0.003039 | 0.001417 |

Fresnel Sag Values

| 15 D Fresnel | 20 D Fresnel |
|---|---|
| 0 | 0 |
| 1.08929E-05 | 7.685E-06 |
| 4.35714E-05 | 3.074E-05 |
| 9.80354E-05 | 6.91653E-05 |
| 0.000174285 | 0.000122961 |
| 0.000272319 | 0.000192128 |
| 0.000392137 | 0.000276666 |
| 0.00053374 | 0.000376575 |
| 0.000697126 | 0.000491858 |
| 0.000882294 | 0.000622514 |
| 0.001089243 | 0.000768544 |
| 0.001317973 | 0.000929949 |
| 0.001568482 | 0.001106731 |
| 0.00184077 | 0.001298891 |
| 0.002134835 | 0.001506429 |
| 0.002450675 | 0.001729348 |
| 0.002788289 | 0.001967649 |
| 0.003147675 | 0.002221334 |
| 0.003528833 | 0.002490404 |
| 0.003931759 | 0.002774861 |
| 0.004356452 | 0.003074707 |
| 0.00480291 | 0.003389945 |
| 0.005271113 | 0.003720576 |
| 0.005761111 | 0.004066604 |
| 0.006272851 | 0.004428029 |

FIG. 30

| | | | |
|---|---|---|---|
| 0.25 | 0.006806 | 0.004805 | 0.003297 | 0.001538 |
| 0.26 | 0.007352 | 0.005197 | 0.003566 | 0.001663 |
| 0.27 | 0.007939 | 0.005605 | 0.003846 | 0.001794 |
| 0.28 | 0.008537 | 0.006028 | 0.004136 | 0.001929 |
| 0.29 | 0.009158 | 0.006466 | 0.004437 | 0.00207 |
| 0.3 | 0.0098 | 0.00692 | 0.004748 | 0.002215 |
| 0.31 | 0.010464 | 0.007389 | 0.00507 | 0.002365 |
| 0.32 | 0.011115 | 0.007874 | 0.005403 | 0.00252 |
| 0.33 | 0.011857 | 0.008374 | 0.005746 | 0.00268 |
| 0.34 | 0.012586 | 0.00889 | 0.006099 | 0.002846 |
| 0.35 | 0.013337 | 0.009421 | 0.006464 | 0.003016 |
| 0.36 | 0.01411 | 0.009967 | 0.006839 | 0.003191 |
| 0.37 | 0.014904 | 0.010529 | 0.007224 | 0.003371 |
| 0.38 | 0.01572 | 0.011106 | 0.00762 | 0.003555 |
| 0.39 | 0.016558 | 0.011699 | 0.008026 | 0.003745 |
| 0.4 | 0.017417 | 0.012307 | 0.008444 | 0.00394 |
| 0.41 | 0.018299 | 0.012931 | 0.008871 | 0.00414 |
| 0.42 | 0.019202 | 0.01357 | 0.00931 | 0.004345 |
| 0.43 | 0.020126 | 0.014225 | 0.009758 | 0.004554 |
| 0.44 | 0.021072 | 0.014895 | 0.010218 | 0.004769 |
| 0.45 | 0.02204 | 0.01558 | 0.010688 | 0.004989 |
| 0.46 | 0.023029 | 0.016281 | 0.011169 | 0.005214 |
| 0.47 | 0.024041 | 0.016998 | 0.01166 | 0.005443 |
| 0.48 | 0.025074 | 0.01773 | 0.012162 | 0.005678 |
| 0.49 | 0.026129 | 0.018477 | 0.012674 | 0.005917 |
| 0.5 | 0.027205 | 0.01924 | 0.013197 | 0.006162 |
| 0.51 | 0.028303 | 0.020019 | 0.013731 | 0.006412 |
| 0.52 | 0.029423 | 0.020813 | 0.014275 | 0.006666 |
| 0.53 | 0.030564 | 0.021622 | 0.01483 | 0.006926 |
| 0.54 | 0.031727 | 0.022447 | 0.015395 | 0.00719 |
| 0.55 | 0.032911 | 0.023288 | 0.015972 | 0.00746 |
| 0.56 | 0.034117 | 0.024144 | 0.016558 | 0.007734 |
| 0.57 | 0.035345 | 0.025016 | 0.017156 | 0.008014 |
| 0.58 | 0.036595 | 0.025903 | 0.017764 | 0.008298 |
| 0.59 | 0.037866 | 0.026805 | 0.018382 | 0.008588 |
| 0.6 | 0.039158 | 0.027724 | 0.019011 | 0.008883 |
| 0.61 | 0.040472 | 0.028658 | 0.019651 | 0.009182 |

| | |
|---|---|
| 0.006803346 | 0.004804855 |
| 0.007361594 | 0.005197084 |
| 0.007938593 | 0.005604719 |
| 0.00853734 | 0.006027764 |
| 0.009157832 | 0.00646622 |
| 0.009800066 | 0.006692009 |
| 0.010464039 | 0.007389379 |
| 0.011149747 | 0.007874089 |
| 0.011857188 | 0.008374224 |
| 0.012586358 | 0.008889787 |
| 0.013337254 | 0.009420782 |
| 0.014109872 | 0.009967212 |
| 0.014904208 | 0.010529081 |
| 0.015720259 | 0.011106394 |
| 0.016558021 | 0.011699153 |
| 0.017417489 | 0.012307364 |
| 0.018298661 | 0.012931103 |
| 0.019201553 | 0.013570157 |
| 0.020126094 | 0.014224747 |
| 0.021072348 | 0.014894807 |
| 0.022040287 | 0.01558034 |
| 0.023029907 | 0.016281352 |
| 0.024041202 | 0.016997847 |
| 0.025074169 | 0.017729983 |
| 0.026128802 | 0.018477306 |
| 0.027205097 | 0.019240282 |
| 0.028303048 | 0.020018761 |
| 0.029422649 | 0.020812275 |
| 0.030563897 | 0.021622254 |
| 0.031726784 | 0.022447278 |
| 0.032911307 | 0.023287829 |
| 0.034117459 | 0.024143912 |
| 0.035345234 | 0.025015534 |
| 0.036594626 | 0.0259027 |
| 0.037865631 | 0.026805417 |
| 0.039158241 | 0.027723691 |
| 0.040472451 | 0.028657529 |

FIG. 30 (cont'd)

| | | | | |
|---|---|---|---|---|
| 0.62 | 0.041808 | 0.029607 | 0.020302 | 0.009487 | 0.041808254 | 0.029606937 |
| 0.63 | 0.043166 | 0.030572 | 0.020963 | 0.009797 | 0.043165645 | 0.030571922 |
| 0.64 | 0.044545 | 0.031552 | 0.021635 | 0.010111 | 0.044544616 | 0.031155249 |
| 0.65 | 0.045945 | 0.032549 | 0.022317 | 0.010431 | 0.045945161 | 0.032548649 |
| 0.66 | 0.047367 | 0.03356 | 0.02301 | 0.010756 | 0.047367274 | 0.033560406 |
| 0.67 | 0.048811 | 0.034588 | 0.023714 | 0.011086 | 0.048810947 | 0.034587767 |
| 0.68 | 0.050276 | 0.035631 | 0.024428 | 0.011421 | 0.050276175 | 0.035630741 |
| 0.69 | 0.051763 | 0.036689 | 0.025153 | 0.011761 | 0.05176295 | 0.036689333 |
| 0.7 | 0.053271 | 0.037764 | 0.025889 | 0.012106 | 0.053271265 | 0.037763553 |
| 0.71 | 0.054801 | 0.038853 | 0.026635 | 0.012456 | 0.054801113 | 0.038853407 |
| 0.72 | 0.056352 | 0.039959 | 0.027392 | 0.012811 | 0.056352487 | 0.039958904 |
| 0.73 | 0.057925 | 0.04108 | 0.028159 | 0.013171 | 0.05792538 | 0.04108005 |
| 0.74 | 0.05952 | 0.042217 | 0.028938 | 0.013536 | 0.059519784 | 0.042216854 |
| 0.75 | 0.061136 | 0.043369 | 0.029727 | 0.013907 | 0.061135691 | 0.043369325 |
| 0.76 | 0.062773 | 0.044537 | 0.030526 | 0.014282 | 0.062773095 | 0.04453747 |
| 0.77 | 0.064432 | 0.045721 | 0.031337 | 0.014663 | 0.064431987 | 0.045721297 |
| 0.78 | 0.066112 | 0.046921 | 0.032158 | 0.015048 | 0.066112359 | 0.046920815 |
| 0.79 | 0.067814 | 0.048136 | 0.032989 | 0.015439 | 0.067814205 | 0.048136033 |
| 0.8 | 0.069538 | 0.049367 | 0.033832 | 0.015835 | 0.069537515 | 0.049366959 |
| 0.81 | 0.071282 | 0.050614 | 0.034685 | 0.016236 | 0.071282282 | 0.050613602 |
| 0.82 | 0.073048 | 0.051876 | 0.035548 | 0.016642 | 0.073048497 | 0.051875971 |
| 0.83 | 0.074836 | 0.053154 | 0.036423 | 0.017053 | 0.074836153 | 0.053154075 |
| 0.84 | 0.076645 | 0.054448 | 0.037308 | 0.017469 | 0.076645240 | 0.054447923 |
| 0.85 | 0.078476 | 0.055758 | 0.038204 | 0.017891 | 0.078475751 | 0.055757524 |
| 0.86 | 0.080328 | 0.057083 | 0.03911 | 0.018317 | 0.080327677 | 0.057082888 |
| 0.87 | 0.082201 | 0.058424 | 0.040028 | 0.018749 | 0.082201009 | 0.058424024 |
| 0.88 | 0.084096 | 0.059781 | 0.040956 | 0.019186 | 0.084095739 | 0.059780942 |
| 0.89 | 0.086012 | 0.061154 | 0.041894 | 0.019628 | 0.086011857 | 0.061153651 |
| 0.9 | 0.087949 | 0.062542 | 0.042844 | 0.020075 | 0.087949355 | 0.062542161 |
| 0.91 | 0.089908 | 0.063946 | 0.043804 | 0.020527 | 0.089908224 | 0.063946483 |
| 0.92 | 0.091888 | 0.065367 | 0.044775 | 0.020984 | 0.091888454 | 0.065366627 |
| 0.93 | 0.09389 | 0.066803 | 0.045757 | 0.021447 | 0.093890037 | 0.066802602 |
| 0.94 | 0.095913 | 0.068254 | 0.046749 | 0.021915 | 0.095912962 | 0.068254419 |
| 0.95 | 0.097957 | 0.069722 | 0.047752 | 0.022388 | 0.0020042778 | 0.069722088 |
| 0.96 | 0.100023 | 0.071206 | 0.048766 | 0.022866 | 2.28052E-05 | 0.071205621 |
| 0.97 | 0.10211 | 0.072705 | 0.049791 | 0.023349 | 0.002109703 | 0.072705028 |
| 0.98 | 0.104218 | 0.07422 | 0.050826 | 0.023838 | 0.004217906 | 0.074220319 |

FIG. 30 (cont'd)

| | | | | |
|---|---|---|---|---|
| 0.99 | 0.106347 | 0.075752 | 0.051873 | 0.024332 | 0.006347404 | 0.075751505 |
| 1 | 0.108498 | 0.077299 | 0.052929 | 0.024831 | 0.008498187 | 0.077298599 |
| 1.01 | 0.11067 | 0.078862 | 0.053997 | 0.025335 | 0.010670245 | 0.07886161 |
| 1.02 | 0.112864 | 0.080441 | 0.055076 | 0.025844 | 0.012863569 | 0.080440551 |
| 1.03 | 0.115078 | 0.082035 | 0.056165 | 0.026359 | 0.015078148 | 0.082035433 |
| 1.04 | 0.117314 | 0.083646 | 0.057265 | 0.026879 | 0.017313971 | 0.083646266 |
| 1.05 | 0.119571 | 0.085273 | 0.058376 | 0.027404 | 0.019571029 | 0.085273064 |
| 1.06 | 0.121849 | 0.086916 | 0.059498 | 0.027934 | 0.021849311 | 0.086915838 |
| 1.07 | 0.124149 | 0.088575 | 0.06063 | 0.02847 | 0.024148806 | 0.0885746 |
| 1.08 | 0.12647 | 0.090249 | 0.061774 | 0.02901 | 0.026469505 | 0.090249362 |
| 1.09 | 0.128811 | 0.09194 | 0.062928 | 0.029557 | 0.028811396 | 0.091940136 |
| 1.1 | 0.131174 | 0.093647 | 0.064093 | 0.030108 | 0.031174468 | 0.093646934 |
| 1.11 | 0.133559 | 0.09537 | 0.065268 | 0.030665 | 0.03355871 | 0.09536977 |
| 1.12 | 0.135964 | 0.097109 | 0.066455 | 0.031227 | 0.035964113 | 0.097108656 |
| 1.13 | 0.138391 | 0.098864 | 0.067652 | 0.031794 | 0.038390664 | 0.098863604 |
| 1.14 | 0.140838 | 0.100635 | 0.068861 | 0.032367 | 0.040838352 | 0.100634628 |
| 1.15 | 0.143307 | 0.102422 | 0.07008 | 0.032945 | 0.043307166 | 0.10242174 |
| 1.16 | 0.145797 | 0.104225 | 0.07131 | 0.033528 | 0.045797096 | 0.104224953 |
| 1.17 | 0.148308 | 0.106044 | 0.072551 | 0.034116 | 0.048308129 | 0.106044282 |
| 1.18 | 0.15084 | 0.10788 | 0.073802 | 0.03471 | 0.050840253 | 0.107879739 |
| 1.19 | 0.153393 | 0.109731 | 0.075065 | 0.035309 | 0.053393458 | 0.109731338 |
| 1.2 | 0.155968 | 0.111599 | 0.076338 | 0.035914 | 0.055967732 | 0.111599092 |
| 1.21 | 0.158563 | 0.113483 | 0.077623 | 0.036524 | 0.058563063 | 0.113483016 |
| 1.22 | 0.161179 | 0.115383 | 0.078918 | 0.037139 | 0.061179439 | 0.115383123 |
| 1.23 | 0.163817 | 0.117299 | 0.080224 | 0.03776 | 0.063816848 | 0.117299428 |
| 1.24 | 0.166475 | 0.119232 | 0.081541 | 0.038386 | 0.066475278 | 0.119231945 |
| 1.25 | 0.169155 | 0.121181 | 0.082869 | 0.039018 | 0.069154717 | 0.121180687 |
| 1.26 | 0.171855 | 0.123146 | 0.084207 | 0.039654 | 0.071855152 | 0.123145671 |
| 1.27 | 0.174577 | 0.125127 | 0.085557 | 0.040297 | 0.074576573 | 0.125126909 |
| 1.28 | 0.177319 | 0.127124 | 0.086918 | 0.040944 | 0.077318965 | 0.127124418 |
| 1.29 | 0.180082 | 0.129138 | 0.088289 | 0.041598 | 0.080082318 | 0.129138212 |
| 1.3 | 0.182867 | 0.131168 | 0.089672 | 0.042256 | 0.082866617 | 0.131168305 |
| 1.31 | 0.185672 | 0.133215 | 0.091065 | 0.04292 | 0.085671851 | 0.133214714 |
| 1.32 | 0.188498 | 0.135277 | 0.092469 | 0.04359 | 0.088498006 | 0.135277454 |
| 1.33 | 0.191345 | 0.137357 | 0.093885 | 0.044264 | 0.091345071 | 0.137356654 |
| 1.34 | 0.194213 | 0.139452 | 0.095311 | 0.044945 | 0.094213032 | 0.139451987 |
| 1.35 | 0.197102 | 0.141564 | 0.096748 | 0.045631 | 0.097101876 | 0.141563812 |

FIG. 30 (cont'd)

| | | | |
|---|---|---|---|
| 1.36 | 0.200012 | 0.143692 | 0.098196 | 0.046322 | | |
| 1.37 | 0.202942 | 0.145837 | 0.099656 | 0.047019 | | |
| 1.38 | 0.205894 | 0.147998 | 0.101126 | 0.047721 | | |
| 1.39 | 0.208866 | 0.150175 | 0.102607 | 0.048429 | | |
| 1.4 | 0.211859 | 0.152369 | 0.104099 | 0.049142 | | |
| 1.41 | 0.214873 | 0.15458 | 0.105602 | 0.049861 | | |
| 1.42 | 0.217907 | 0.156807 | 0.107116 | 0.050586 | | |
| 1.43 | 0.220963 | 0.15905 | 0.108641 | 0.051316 | | |
| 1.44 | 0.224039 | 0.16131 | 0.110177 | 0.052051 | | |
| 1.45 | 0.227136 | 0.163586 | 0.111725 | 0.052793 | | |
| 1.46 | 0.230254 | 0.165879 | 0.113283 | 0.053539 | | |
| 1.47 | 0.233392 | 0.168189 | 0.114852 | 0.054292 | | |
| 1.48 | 0.236551 | 0.170515 | 0.116432 | 0.05505 | | |
| 1.49 | 0.239731 | 0.172858 | 0.118024 | 0.055813 | | |
| 1.5 | 0.242931 | 0.175218 | 0.119626 | 0.056582 | | |
| 1.51 | 0.246153 | 0.177594 | 0.12124 | 0.057357 | | |
| 1.52 | 0.249394 | 0.179987 | 0.122864 | 0.058138 | | |
| 1.53 | 0.252657 | 0.182396 | 0.1245 | 0.058924 | | |
| 1.54 | 0.25594 | 0.184822 | 0.126147 | 0.059716 | | |
| 1.55 | 0.259244 | 0.187265 | 0.127805 | 0.060513 | | |
| 1.56 | 0.262568 | 0.189725 | 0.129474 | 0.061316 | | |
| 1.57 | 0.265913 | 0.192201 | 0.131154 | 0.062125 | | |
| 1.58 | 0.269278 | 0.194694 | 0.132845 | 0.06294 | | |
| 1.59 | 0.272664 | 0.197204 | 0.134547 | 0.06376 | | |
| 1.6 | 0.27607 | 0.199731 | 0.136261 | 0.064586 | 0.10001159 | 0.143692031 |
| 1.61 | 0.279497 | 0.202275 | 0.137985 | 0.065418 | 0.102942162 | 0.145836659 |
| 1.62 | 0.282945 | 0.204836 | 0.139721 | 0.066256 | 0.105893577 | 0.147997713 |
| 1.63 | 0.286413 | 0.207413 | 0.141468 | 0.067099 | 0.108865822 | 0.150175209 |
| 1.64 | 0.289901 | 0.210007 | 0.143226 | 0.067948 | 0.111858885 | 0.152369164 |
| 1.65 | 0.29341 | 0.212618 | 0.144995 | 0.068803 | 0.114872751 | 0.154579594 |
| 1.66 | 0.29694 | 0.215247 | 0.146776 | 0.069664 | 0.117907408 | 0.156806516 |
| 1.67 | 0.300489 | 0.217892 | 0.148568 | 0.07053 | 0.120962841 | 0.059049947 |
| 1.68 | 0.30406 | 0.220554 | 0.15037 | 0.071403 | 0.124039037 | 0.061309905 |
| 1.69 | 0.30765 | 0.223233 | 0.152185 | 0.072281 | 0.127135982 | 0.063586405 |
| 1.7 | 0.311261 | 0.225929 | 0.15401 | 0.073165 | 0.130253662 | 0.065879467 |
| 1.71 | 0.314892 | 0.228642 | 0.155846 | 0.074055 | 0.133392063 | 0.068189107 |
| 1.72 | 0.318544 | 0.231373 | 0.157694 | 0.074951 | 0.13655117 | 0.070515343 |
| | | | | | 0.139730973 | 0.072858193 |
| | | | | | 0.142931453 | 0.075217674 |
| | | | | | 0.146152598 | 0.077593806 |
| | | | | | 0.149394394 | 0.079986607 |
| | | | | | 0.152656825 | 0.082396094 |
| | | | | | 0.155939877 | 0.084822287 |
| | | | | | 0.159243537 | 0.087265204 |
| | | | | | 0.162567788 | 0.089724864 |
| | | | | | 0.165912617 | 0.092201287 |
| | | | | | 0.169278009 | 0.094694491 |
| | | | | | 0.172663948 | 0.097204496 |
| | | | | | 0.17607042 | 0.099731322 |
| | | | | | 0.17949741 | 0.102274988 |
| | | | | | 0.182944902 | 0.104635515 |
| | | | | | 0.186412882 | 0.107412922 |
| | | | | | 0.189901334 | 0.11000723 |
| | | | | | 0.193410243 | 0.112618458 |
| | | | | | 0.096939593 | 0.115246629 |
| | | | | | 0.100489369 | 0.117891761 |
| | | | | | 0.104059555 | 0.120553877 |
| | | | | | 0.107650136 | 0.123232997 |
| | | | | | 0.111261096 | 0.125929143 |
| | | | | | 0.11489242 | 0.128642335 |
| | | | | | 0.11854409 | 0.131372596 |

FIG. 30 (cont'd)

| | | | |
|---|---|---|---|
| 1.73 | 0.322216 | 0.23412 | 0.159553 | 0.075853 | 0.122216092 | 0.134119948 |
| 1.74 | 0.325908 | 0.236884 | 0.161423 | 0.076761 | 0.12590841 | 0.136884412 |
| 1.75 | 0.329621 | 0.239666 | 0.163305 | 0.077674 | 0.129621027 | 0.139666601 |
| 1.76 | 0.333354 | 0.242465 | 0.165198 | 0.078594 | 0.133353927 | 0.142464765 |
| 1.77 | 0.337107 | 0.245281 | 0.167102 | 0.079519 | 0.137107094 | 0.145280699 |
| 1.78 | 0.340881 | 0.248114 | 0.169017 | 0.080451 | 0.140880512 | 0.148113834 |
| 1.79 | 0.344674 | 0.250964 | 0.170944 | 0.081388 | 0.144674165 | 0.150964194 |
| 1.8 | 0.348488 | 0.253832 | 0.172882 | 0.082332 | 0.148488035 | 0.153831802 |
| 1.81 | 0.352322 | 0.256717 | 0.174831 | 0.083281 | 0.152322106 | 0.156716681 |
| 1.82 | 0.356176 | 0.259619 | 0.176792 | 0.084237 | 0.156176363 | 0.159618853 |
| 1.83 | 0.360051 | 0.262538 | 0.178764 | 0.085198 | 0.160050788 | 0.162538343 |
| 1.84 | 0.363945 | 0.265475 | 0.180747 | 0.086166 | 0.163945364 | 0.165475175 |
| 1.85 | 0.36786 | 0.268429 | 0.182741 | 0.08714 | 0.167860076 | 0.168429372 |
| 1.86 | 0.371795 | 0.271401 | 0.184747 | 0.088119 | 0.171794905 | 0.171400958 |
| 1.87 | 0.37575 | 0.27439 | 0.186765 | 0.089105 | 0.175749835 | 0.174389958 |
| 1.88 | 0.379725 | 0.277396 | 0.188794 | 0.090097 | 0.17972485 | 0.177396396 |
| 1.89 | 0.38372 | 0.28042 | 0.190834 | 0.091095 | 0.183719931 | 0.180420297 |
| 1.9 | 0.387735 | 0.283462 | 0.192885 | 0.0921 | 0.187735063 | 0.183461685 |
| 1.91 | 0.39177 | 0.286521 | 0.194948 | 0.09311 | 0.191770227 | 0.186520586 |
| 1.92 | 0.395825 | 0.289597 | 0.197022 | 0.094127 | 0.195825407 | 0.189597025 |
| 1.93 | 0.399901 | 0.292691 | 0.199108 | 0.095149 | 0.199900585 | 0.192691027 |
| 1.94 | 0.403996 | 0.295803 | 0.201205 | 0.096178 | 0.203995744 | 0.195802618 |
| 1.95 | 0.408111 | 0.298932 | 0.203314 | 0.097214 | 0.208110866 | 0.198931824 |
| 1.96 | 0.412246 | 0.302079 | 0.205434 | 0.098255 | 0.212245934 | 0.202078671 |
| 1.97 | 0.416401 | 0.305243 | 0.207566 | 0.099303 | 0.216400931 | 0.205243185 |
| 1.98 | 0.420576 | 0.308425 | 0.209709 | 0.100357 | 0.220575838 | 0.208425392 |
| 1.99 | 0.424771 | 0.311625 | 0.211863 | 0.101417 | 0.224770639 | 0.211625319 |
| 2 | 0.428985 | 0.314843 | 0.214029 | 0.102484 | 0.228985315 | 0.214842992 |
| 2.01 | 0.43322 | 0.318078 | 0.216207 | 0.103557 | 0.233219848 | 0.218078844 |
| 2.02 | 0.437474 | 0.321332 | 0.218396 | 0.104636 | 0.237474221 | 0.221331689 |
| 2.03 | 0.441748 | 0.324603 | 0.220597 | 0.105722 | 0.241748416 | 0.224602766 |
| 2.04 | 0.446042 | 0.327892 | 0.222809 | 0.106814 | 0.246042414 | 0.227891699 |
| 2.05 | 0.450356 | 0.331199 | 0.225032 | 0.107912 | 0.250356198 | 0.231198517 |
| 2.06 | 0.45469 | 0.334523 | 0.227268 | 0.109017 | 0.25468975 | 0.234523246 |
| 2.07 | 0.459043 | 0.337866 | 0.229515 | 0.110128 | 0.259043051 | 0.237865916 |
| 2.08 | 0.463416 | 0.341227 | 0.231773 | 0.111246 | 0.263416083 | 0.241226554 |
| 2.09 | 0.467809 | 0.344605 | 0.234043 | 0.11237 | 0.267808827 | 0.244460519 |

FIG. 30 (cont'd)

| | | | | |
|---|---|---|---|---|
| 2.1 | 0.472221 | 0.348002 | 0.236325 | 0.113501 | 0.272221267 | 0.248001852 |
| 2.11 | 0.476653 | 0.351417 | 0.238618 | 0.114638 | 0.276653382 | 0.251141657 |
| 2.12 | 0.481105 | 0.354849 | 0.240923 | 0.115782 | 0.281105154 | 0.254849372 |
| 2.13 | 0.485577 | 0.3583 | 0.243239 | 0.116932 | 0.285576566 | 0.258300289 |
| 2.14 | 0.490068 | 0.361769 | 0.245567 | 0.118089 | 0.290067598 | 0.261176935 |
| 2.15 | 0.494578 | 0.365257 | 0.247907 | 0.119253 | 0.294578232 | 0.265256585 |
| 2.16 | 0.499108 | 0.368762 | 0.250258 | 0.120423 | 0.299108448 | 0.268762025 |
| 2.17 | 0.503658 | 0.372286 | 0.252622 | 0.121599 | 0.303658229 | 0.272285699 |
| 2.18 | 0.508228 | 0.375828 | 0.254996 | 0.122783 | 0.308227556 | 0.275827639 |
| 2.19 | 0.512816 | 0.379388 | 0.257383 | 0.123973 | 0.312816408 | 0.279387875 |
| 2.2 | 0.517425 | 0.382966 | 0.259781 | 0.125169 | 0.317424769 | 0.282966439 |
| 2.21 | 0.522053 | 0.386563 | 0.262191 | 0.126373 | 0.322052618 | 0.286563362 |
| 2.22 | 0.5267 | 0.390179 | 0.264613 | 0.127583 | 0.326699936 | 0.290178675 |
| 2.23 | 0.531367 | 0.393812 | 0.267046 | 0.1288 | 0.331366705 | 0.293812411 |
| 2.24 | 0.536053 | 0.397465 | 0.269491 | 0.130024 | 0.336052905 | 0.297464601 |
| 2.25 | 0.540759 | 0.401135 | 0.271948 | 0.131254 | 0.340758517 | 0.301135278 |
| 2.26 | 0.545484 | 0.404824 | 0.274417 | 0.132491 | 0.345483522 | 0.304824475 |
| 2.27 | 0.550228 | 0.408532 | 0.276898 | 0.133735 | 0.350227901 | 0.308532223 |
| 2.28 | 0.554992 | 0.412259 | 0.27939 | 0.134986 | 0.354991633 | 0.312258557 |
| 2.29 | 0.559775 | 0.416004 | 0.281894 | 0.136244 | 0.359775700 | 0.316003509 |
| 2.3 | 0.564577 | 0.419767 | 0.284411 | 0.137509 | 0.364577082 | 0.319767113 |
| 2.31 | 0.569399 | 0.423549 | 0.286938 | 0.138781 | 0.369398760 | 0.323549402 |
| 2.32 | 0.57424 | 0.42735 | 0.289478 | 0.14006 | 0.374239713 | 0.327350412 |
| 2.33 | 0.5791 | 0.43117 | 0.292029 | 0.141345 | 0.379099923 | 0.331170175 |
| 2.34 | 0.583979 | 0.435009 | 0.294593 | 0.142638 | 0.383979371 | 0.335008727 |
| 2.35 | 0.588878 | 0.438866 | 0.297169 | 0.143938 | 0.388878034 | 0.338866103 |
| 2.36 | 0.593796 | 0.442742 | 0.299756 | 0.145244 | 0.393795895 | 0.342742336 |
| 2.37 | 0.598733 | 0.446637 | 0.302355 | 0.146558 | 0.398732933 | 0.346637464 |
| 2.38 | 0.603689 | 0.450552 | 0.304967 | 0.147879 | 0.403689128 | 0.35055152 |
| 2.39 | 0.608664 | 0.454485 | 0.30759 | 0.149207 | 0.408664461 | 0.354484542 |
| 2.4 | 0.613659 | 0.458437 | 0.310225 | 0.150542 | 0.413658911 | 0.358436565 |
| 2.41 | 0.618672 | 0.462408 | 0.312872 | 0.151885 | 0.418672459 | 0.362407626 |
| 2.42 | 0.623705 | 0.466398 | 0.315531 | 0.153234 | 0.423705084 | 0.266397776 |
| 2.43 | 0.628757 | 0.470407 | 0.318202 | 0.154591 | 0.428756766 | 0.270407006 |
| 2.44 | 0.633827 | 0.474435 | 0.320885 | 0.155955 | 0.433827486 | 0.2744354 |
| 2.45 | 0.638917 | 0.478483 | 0.32358 | 0.157327 | 0.438917222 | 0.278482979 |
| 2.46 | 0.644026 | 0.48255 | 0.326287 | 0.158705 | 0.444025954 | 0.282549782 |

FIG. 30 (cont'd)

| | | | | |
|---|---|---|---|---|
| 2.47 | 0.649154 | 0.486636 | 0.329007 | 0.160091 | 0.349153663 | 0.286635846 |
| 2.48 | 0.6543 | 0.490741 | 0.331738 | 0.161485 | 0.354300327 | 0.29074121 |
| 2.49 | 0.659466 | 0.494866 | 0.334481 | 0.162886 | 0.359465927 | 0.294865912 |
| 2.5 | 0.66465 | 0.49901 | 0.337237 | 0.164294 | 0.364650442 | 0.299009961 |

FIG. 30 (cont'd)

(15-D) A-IOL 600-12

| Surface | Radius | Conic Constant | Center Thickness | Edge Thickness | Refractive Index |
|---|---|---|---|---|---|
| 1 | 3.5998 | -0.2905 | 1.6422 | 0.2 | 1.425 |
| 2 | -14.1730 | -7.5034 | --- | --- | 1.336 |
| 3 | -4.5902 | -1.3357 | 0.2 | 0.7493 | 1.425 |
| 4 | -32.8439 | 0 | --- | --- | 1.336 |

Fig. 33D

(20-D) A-IOL 600-11

| Surface | Radius | Conic Constant | Center Thickness | Edge Thickness | Refractive Index |
|---|---|---|---|---|---|
| 1 | 3.5998 | -0.2905 | 1.6303 | 0.2 | 1.425 |
| 2 | -15.1923 | -5.4725 | --- | --- | 1.336 |
| 3 | -6.5062 | -0.0229 | 0.2 | 0.5837 | 1.425 |
| 4 | -32.8439 | 0 | --- | --- | 1.336 |

Fig. 33C

(25-D) A-IOL 600-10

| Surface | Radius | Conic Constant | Center Thickness | Edge Thickness | Refractive Index |
|---|---|---|---|---|---|
| 1 | 3.5998 | -0.2905 | 1.6418 | 0.2 | 1.425 |
| 2 | -13.0683 | -16.4614 | --- | --- | 1.336 |
| 3 | -9.4801 | +0.2666 | 0.2 | 0.4219 | 1.425 |
| 4 | -32.8439 | 0 | --- | --- | 1.336 |

Fig. 33B

(30-D) A-IOL 600-9

| Surface | Radius | Conic Constant | Center Thickness | Edge Thickness | Refractive Index |
|---|---|---|---|---|---|
| 1 | 3.5998 | -0.2905 | 1.6421 | 0.2 | 1.425 |
| 2 | -12.5916 | -20.0448 | --- | --- | 1.336 |
| 3 | -20.3352 | +19.9784 | 0.2 | 0.2530 | 1.425 |
| 4 | -32.8439 | 0 | --- | --- | 1.336 |

Fig. 33A

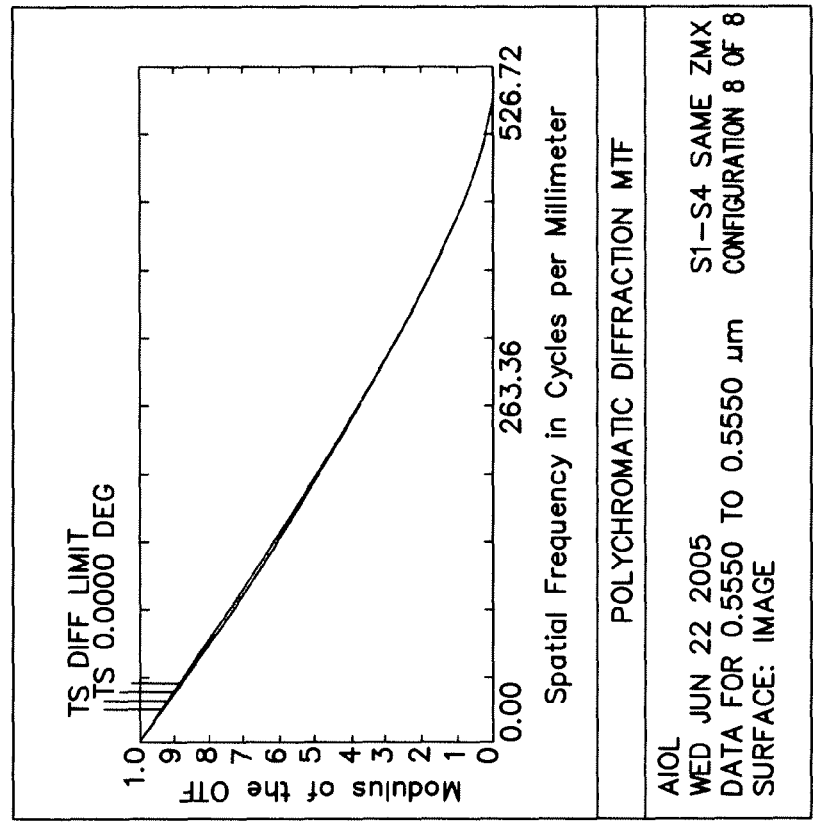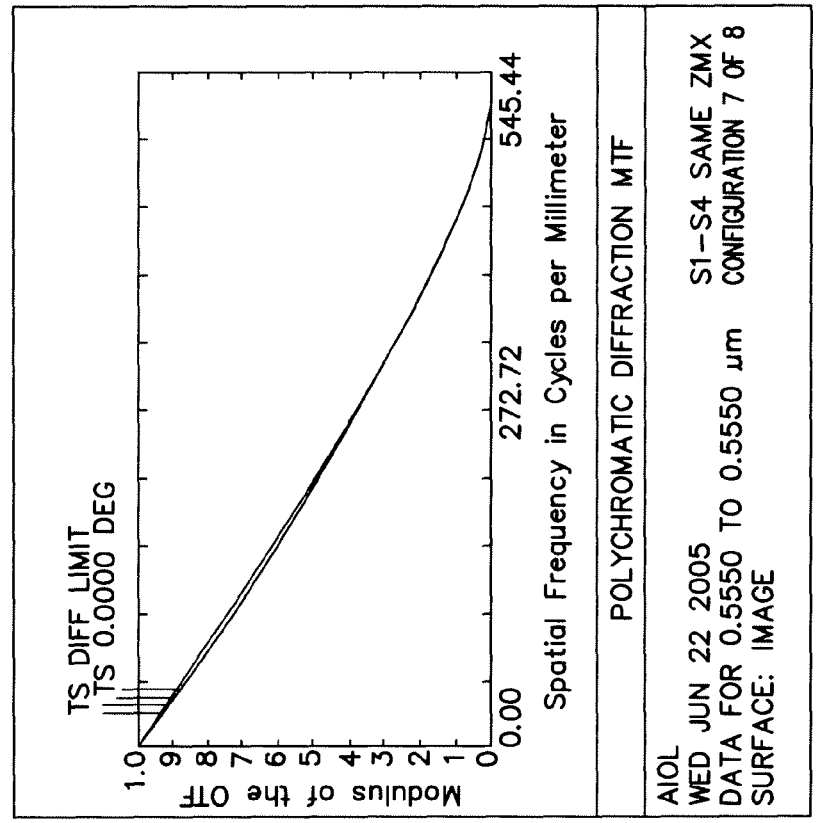
FIG. 34A

(30-D) A-IOL 600-13

| Surface | Radius | Conic Constant | Paraxial Power (D) | Accommodative Amplitude (D/mm) |
|---|---|---|---|---|
| 1 | 2.873 | -0.8325 | 44.2 | 3.44 |
| 2 | -6.379 | 1.4255 | | --- |
| 3 | -22.927 | 0 | -15.9 | --- |
| 4 | 7.418 | 0 | | --- |

Fig. 36A

(25-D) A-IOL 600-14

| Surface | Radius | Conic Constant | Paraxial Power (D) | Accommodative Amplitude (D/mm) |
|---|---|---|---|---|
| 1 | 3.045 | -0.6691 | 39.4 | 3.00 |
| 2 | -8.347 | -0.1282 | | --- |
| 3 | -22.927 | 0 | -15.9 | --- |
| 4 | 7.418 | 0 | | --- |

Fig. 36B

(20-D) A-IOL 600-15

| Surface | Radius | Conic Constant | Paraxial Power (D) | Accommodative Amplitude (D/mm) |
|---|---|---|---|---|
| 1 | 4.174 | -0.4607 | 34.8 | 2.5 |
| 2 | -6.434 | -2.9411 | | --- |
| 3 | -22.927 | 0 | -15.9 | --- |
| 4 | 7.418 | 0 | | --- |

Fig. 36C

(15-D) A-IOL 600-16

| Surface | Radius | Conic Constant | Paraxial Power (D) | Accommodative Amplitude (D/mm) |
|---|---|---|---|---|
| 1 | 4.993 | -0.4823 | 30 | 2.10 |
| 2 | -7.174 | -2.8127 | | --- |
| 3 | -22.927 | 0 | -15.9 | --- |
| 4 | 7.418 | 0 | | --- |

Fig. 36D

ASPHERIC LENSES AND LENS FAMILY

RELATED APPLICATION DATA

This application is a continuation of U.S. Ser. No. 11/248,052 filed Oct. 12, 2005, which is a continuation-in-part of U.S. Ser. No. 11/057,278 filed on Feb. 11, 2005, which is a continuation-in-part of U.S. Ser. No. 11/054,823 filed on Feb. 10, 2005, which is a continuation-in-part of U.S. Ser. No. 10/703,884 filed on Nov. 7, 2003, which is a continuation-in-part of U.S. Ser. No. 10/403,808 filed on Mar. 31, 2003, and incorporates by reference all of these prior application and claims the benefit of priority to these prior applications under 35 U.S.C. 120.

BACKGROUND OF THE INVENTION

1. Field of the Invention

Embodiments of the invention are directed to individual aspheric intra ocular lenses (IOLs) including multi-component accommodating intraocular lenses (referred to herein as "A-IOLs") that provide specialized control of spherical aberration and other physical lens parameters; to a family of aspheric intraocular lenses including a family of multi-component accommodating intraocular lenses having consistent labeling, selection and performance parameters; and to a method for designing such IOLs, A-IOLs and associated lens families.

2. Description of Related Art

A simple optical system consists of a lens, which can form an image of an object. In the most basic, ideal situation, a perfect plane wavefront coming from an object located an infinite distance from the lens will be imaged to a focal point one focal length away from the lens along an optical axis of the optical system. Lens defects induce aberrations to the wavefronts of light from an object as they pass through the lens resulting in an image that is blurry.

Different types of lens defects or optical system defects produce different types and degrees of aberrations that may generally appear similar to the naked eye. For example, if a perfect lens is moved along the optical axis of the optical system, the image of the object formed by the lens will suffer from defocus. Stated differently, if the surface upon which the image is viewed is moved along the optical axis, the image will likewise be defocused. The aberration of astigmatism results from in an optical system having a different focusing power in the horizontal direction than in the vertical direction, for example, resulting in a distorted image at every image location. Another troublesome aberration known as spherical aberration, illustrated in FIG. 1, is produced by a lens 5 having spherical surfaces 11, 12. Light ray bundle 7 passing through the lens near its center is brought to a focus at a different position on the optical axis than the light ray bundles 6, 8 passing through the lens nearer its circumference. By convention, the spherical aberration of a lens is measured by the longitudinal or transverse distance between the center- and edge-focused rays of light incident on the lens as a plane wavefront originating at an optically infinite object distance, O. This is referred to as inherent spherical aberration. If a spherical lens, which by definition has inherent spherical aberration, is decentered with respect to the optical axis passing through the center of the lens, then the resulting image will be affected by other aberrations including coma and astigmatism. As mentioned above, any one or combination of these aberrations will cause the image to appear blurry, washed out or otherwise lacking in subjective quality.

The optical system of the eye is known as an ocular system, illustrated in FIG. 2. In simple anatomical terms, the ocular system 100 is comprised of the cornea 1, the iris 2, the crystalline lens 3, and the retina 4. The cornea is the first component of the ocular system to receive light coming from an object and provides roughly two-thirds of the principal focusing capability of the ocular system. The crystalline lens provides the remaining focusing capability of the eye. If a plane wavefront coming from an object located at optical infinity is focused by the cornea and crystalline lens to a point in front of the retina, the eye is referred to as myopic. On the other hand, if the combined focusing power of the cornea and crystalline lens is too weak such that a plane wavefront is focused behind the retina, the ocular system is referred to as hyperopic. The function of the iris is to limit the amount of light passing through the ocular system. The crystalline lens is uniquely adapted to fine tune the focusing ability of the ocular system allowing the healthy eye to form sharp images of objects both far away and up close. The retina is the image detector of the ocular system and the interface between the eye and the brain.

As people age, the crystalline lens loses its capability to allow the ocular system to form images on the retina of near objects (i.e., closer than about 10 inches). This phenomenon is known as presbyopia. Presbyopia is the inability to accommodate or focus on an object close to the eye. In certain cases, an intraocular lens that is designed to restore the accommodative capability of the eye may be provided. These lenses are referred to as accommodating intraocular lenses (accommodating IOLs). These accommodating IOLs may be of a single optic design or a multi-component (typically two-optic) design referred to herein as a multi-component accommodating IOL (A-IOL). Although accommodating IOLs and A-IOLs have both shared and unique advantages, A-IOLs are considered to be able to provide a greater amount of accommodating power than their single element counterparts. Examples of alternative A-IOL designs are disclosed in U.S. Pat. Nos. 5,275,623; 6,423,094; 6,488,708; 6,858,040; and U.S. Published Application Nos. 2004/0015236 and 2003/0130732, the disclosures of which are incorporated by reference in their entireties to the fullest extent allowed by applicable laws and rules. Other complications, e.g., cataracts, may require that the defective crystalline lens be removed from the ocular system and a synthetic lens referred to as a pseudophakic intraocular lens (IOL) be put in its place. Alternatively, a phakic IOL may be implanted without removing the natural crystalline lens to correct refractive errors such as those correctable by spectacles, contact lenses or corneal refractive procedures (e.g. LASIK, CK, PRK, LASEK, etc.).

Although IOLs have been around for more than 40 years, they still do not provide the ocular system with the visual performance obtained with a healthy natural crystalline lens. This is partly due to material considerations, optical characteristics, placement accuracy and stability and other factors relating to the IOL that detract from optimal visual performance. In addition, the natural crystalline lens has certain aberrations of opposite sign to those same aberrations produced by the cornea, such that the total aberrations are reduced. This has been referred to as aberration emmetropization. In recognition of these factors, various solutions have been developed. For example, silicone has become a favored IOL material, in addition to PMMA, hydrogel, and hydrophilic and hydrophobic acrylic materials. Scores of haptic designs have been and continue to be developed to address the positioning and stability concerns of implanted IOLs. Accommodating IOLs and A-IOLs suffer from the same issues of positioning, stability and misalignment. Different surface shapes of IOLs have been provided to minimize lens weight and thickness and to control aberrations that degrade image quality. For illustration, Table 1 (Tables 1-4 are located at the end of the specification) lists the optical prescription and technical specifications of two exemplary IOLs referred to as: the LI61U, a conventional IOL with spherical anterior and posterior surfaces, manufactured by Bausch & Lomb Incorporated, Rochester, N.Y., and the Tecnis Z9000, an advanced IOL with a prolate anterior surface and a spherical posterior surface (Advanced Medical Optics, Santa Ana, Calif.). In brief, the LI61U lens has positive inherent spherical aberration as with any IOL having spherical surfaces. The Tecnis Z9000 IOL has negative spherical aberration in an amount designed to offset or counter balance the positive spherical aberration of the average cornea. While both of these lenses offer certain advantages, the Tecnis Z9000 lens is directed at controlling some component of spherical aberration in the ocular system to achieve improved image quality. The intended result thus appears as one of minimizing residual spherical aberration in the image for the average population. It is well known, however, that non-accommodating IOLs, accommodating IOLs and A-IOLs are subject to movement and resulting misalignment or decentering after implantation and, that, when a lens with spherical aberration is decentered, asymmetrical aberrations such as coma and astigmatism are introduced into the image. While the effects of spherical aberration can be effectively but not completely mitigated by spectacles, the effects of coma cannot.

In view of the foregoing, the inventor has recognized the need for IOLs accommodating IOLs and A-IOLs of alternative designs and construction that can selectively control spherical aberration, and which provide improved visual performance in ocular systems to a degree not provided by currently available lenses when used in these systems.

The availability of IOLs having different values of spherical aberration raises additional issues not heretofore dealt with in the art. Persons skilled in the art understand that an IOL is described and generally labeled for selection by two parameters: lens power and a lens constant such as, e.g., the A-constant (other lens constants may be referred to, for example, as a surgeon factor or ACD constant). A-IOLs may be similarly labeled with lens power and a lens constant, however the lens constant may differ from the typical A-constant used with IOLs and may work with a modified lens power formula. Labeled lens power is expressed as the paraxial power of the lens. The paraxial power of the lens is the power of the lens through the center region of the lens very close to the optical axis. A lens having inherent spherical aberration, however, has a true power that is different than the paraxial power of the lens. For example, in a spherical lens having positive spherical aberration, the power of the lens increases as a function of radial distance away from the center of the lens. For example, using the lens prescription data for the LI61U lens from Table 3 below, the radial profile of local power and average power is as follows:

| Ray Height | Local Power (D) | Diameter | Average Power (D) |
|---|---|---|---|
| 0 | 22.00 | 0 | 22.00 |
| 0.5 | 22.05 | 1.0 | 22.02 |
| 1.0 | 22.19 | 2.0 | 22.09 |
| 1.5 | 22.43 | 3.0 | 22.21 |
| 2.0 | 22.79 | 4.0 | 22.38 |
| 2.5 | 23.27 | 5.0 | 22.61 |
| 3.0 | 23.91 | 6.0 | 22.90 |

Although this variation in power is generally, albeit imperfectly, accounted for by the various selection formulae used by surgeons for equiconvex spherical lens products, the standard formulae do not accurately account for the power variations in aspheric IOLs having inherent spherical aberration with different radial profiles.

An additional, practical concern is addressed in the following exemplary scenario. It is not uncommon for a surgeon who regularly performs IOL procedures to consistently use a limited number of IOL types or brands in their practice. For example, assume the surgeon generally prescribes the Tecnis Z9000 lens listed in Table 1 and the LI61U lens as his common alternative IOL. Each of these lens brands carries a different labeled lens A-constant (e.g., $A_{Z9000}$=119; $A_{LI61U}$=118). Using the standard lens power equation (P=A−2.5L−0.9K, where P is the power of the IOL to be implanted, A is the A-constant of the IOL, L is the measured axial length of the eye and K is the keratometric power of the cornea; see below) for selecting the appropriate IOL power would indicate the use of the Tecnis Z9000 lens having a paraxial power of 23D (and inherent negative spherical aberration), or the LI61U lens having a paraxial power of 22D (and inherent positive spherical aberration). Stated differently, because these lenses will have the same shape factor to account for their spherical aberration values; i.e., they are both equiconvex), they will be labeled as having different A-constants despite both of them having a power equal to 22D. Unless the surgeon (or more typically an assistant) correctly modifies the entry of data to account for the different A constant values of the two lenses, the patient risks having an IOL implanted whose power correction is off by one diopter. Not only is the patient's resulting vision sub-optimal, but there may be additional time, effort and inconvenience for the physician.

Accordingly, as different lenses, lens families and lens brands (including those now having different spherical aberration amounts) are available for selection by the surgeon, lenses having consistently labeled parameters that inform the surgeon of the desired, correct selection would be advantageous. The obvious advantages are the removal of guesswork on the part of the surgeon and removal of the need for the surgeon to invent new formulae to account for characteristics of the lens that may vary, such as true power and spherical aberration value. Another advantageous benefit will be realized by the lens manufacturer and pertains to various governmental approval processes for regulated products such as IOLs. For example, the approval from the US-FDA for a child-IOL having a labeled power and A-constant consistent with a parent-IOL in the exemplary case of the parent-IOL and the child-IOL having different spherical aberration values, will be considerably less burdensome and expensive than if the labeled parameters for the parent-IOL and child-IOL are necessarily different. (The term "parent-IOL" as used herein refers to an existing spherical lens or lens line identified by a labeled power and lens constant; the term "child-IOL" refers to a subsequent aspheric lens or lens line that is (or can be) labeled with the same lens power and lens constant as the parent lenses). Thus, there is a need for a family of IOLs whose individual members have characteristics that allow consistent, selection-based labeling of the lens products.

The inventor has also recognized that standardization of certain physical characteristics of A-IOLs would be advantageous both in terms of evaluating lens performance and for handling and inserting the A-IOL. For instance, if the anterior lens of a two-lens A-IOL has a substantially constant positive optical power over a broad power range for the A-IOL family, the posterior lens shape will necessarily change in order to vary the overall power of the A-IOL. For a certain range of negative optical powers, one or more physical parameters of the posterior lens (and thus the A-IOL) may become undesirable. For example, center thickness may become too thin for lens integrity, edge thickness may become too thick for a particular injector bore, lens volume, cross sectional area, thickness profile and/or shape may cause stability, insertion or other problems. Accordingly, a degree of constancy or standardization of one or more of these parameters over a family of A-IOLs will provide improvements in efficiency, cost and performance.

SUMMARY OF THE INVENTION

An embodiment of the invention is directed to an aspheric IOL having shape and other characteristics such that the transmission of a wavefront of light through the lens imparts no additional spherical aberration to the wavefront. As used herein, the term "shape" will specifically be referred to as "surface shape" meaning the contour or profile shape of a lens surface, or "shape factor" (defined in numerical terms below) meaning the overall shape of the lens (e.g., concave, convex, plano-convex, equiconcave, etc.). For the ocular system aspects described herein, the wavelength range of light will be the visible spectrum centered at 555 nm. A non-ocular optical system can be designed to minimize aberrations over a different wavelength range. In an aspect, the lens has no inherent spherical aberration. In other words, a plane wavefront coming from an object at an optically infinite distance will be refracted by the lens to a sharp focal point on the optical axis of the lens. In another aspect in which the lens is used in an optical system having an optical axis, that includes a focusing optical element located on an object side of the lens and an image plane located on an image side of the lens, the lens will not induce any spherical aberration to a converging wavefront passing through the lens produced by the focusing element acting upon a plane wavefront incident upon the focusing element. In an aspect in which the optical system is an ocular system; i.e., the focusing element is the cornea of an eye that typically produces positive spherical aberration, the lens is an aspheric IOL that induces no additional spherical aberration to the converging wavefront incident on the IOL from the cornea. In this aspect, the IOL has a finite amount of inherent negative spherical aberration substantially less than an amount required to balance the positive spherical aberration of the cornea. In a particular variation of the second aspect, an IOL has an inherent amount of negative spherical aberration that mimics the spherical aberration of a healthy, natural crystalline lens in a relaxed state; i.e., between about negative (−)0.13 micron to negative (−)0.07 micron of spherical aberration and, in a particular variation of this aspect, about negative (−)0.1 micron of spherical aberration, induced in a converging wavefront propagating from the cornea through the IOL.

A lens having no inherent spherical aberration is advantageous in that the amount of misalignment or decentering from the visual axis typically encountered in an ocular system will not induce asymmetric aberrations such as coma or astigmatism. Alternatively, an aspheric IOL having a known amount of inherent negative spherical aberration may be advantageous in the exemplary case of a post-LASIK myopic patient having additional positive spherical aberration induced by the LASIK procedure. It is known that the human brain is adapted to effectively process a finite amount of positive spherical aberration in the ocular image. According to an aspect of the embodiment, the inherent negative spherical aberration of the IOL will be limited to a range wherein the induced coma and/or astigmatism due to decentering or movement of the IOL will not exceed a predetermined value. In another aspect, an aspheric IOL having inherent positive spherical aberration will be advantageous in certain circumstances.

In an aspect, the lens has a constant ratio of a posterior apical radius of curvature to an anterior apical radius of curvature as a function of lens power. In another aspect, the ratio of an anterior surface conic constant of the lens to the posterior surface conic constant of the lens is constant for all lens radii. In a particular aspect, the ratio of anterior conic constant to posterior surface conic constant is equal to one. The apical radii will be used to influence the lens shape factor, defined as $(R_2+R_1)/(R_2-R_1)$, where $R_1$ and $R_2$ are the posterior and anterior apical radii, respectively.

Another embodiment of the invention is directed to a family of aspheric IOLs. According to an aspect, the family of IOLs may be any two or more individual aspheric IOLs having the same labeled lens power values, different spherical aberration values, identical lens-constant values (e.g., A-constant) and different shape factors. Alternatively, the individual aspheric IOLs may have different labeled lens power values. More generally, a family may consist of lens lines A and B, each line having a different value for spherical aberration throughout the entire range of labeled lens powers for each line. In this case, the A-constant can remain the same for both the A and B line by producing each line with a different lens shape factor. Alternatively, the family of aspheric IOLs may consist of a single line of lenses having distinct discontinuous shifts in the value of spherical aberration through different ranges of labeled lens powers. In this case, the A-constant can remain the same throughout the full range of labeled powers as long as the lens shape factor is different for each range of powers with different spherical aberration values. In an aspect, the family of IOLs comprises at least one IOL in a first group having an inherent negative spherical aberration value, at least one IOL in a second group having an inherent spherical aberration value substantially equal to zero and at least one IOL in a third group having an inherent positive spherical aberration value. According to an aspect, at least one of the IOLs in each of the groups has the same labeled lens power values. In the case of an ocular system in which the cornea has a typical focusing power between about 37 diopters to 49 diopters, the IOL has an inherent amount of negative spherical aberration such that no spherical aberration is induced in the converging wavefront passing through the IOL from the cornea. In a particular aspect, the amount of inherent negative spherical aberration in the IOL mimics that in a healthy crystalline lens in a relaxed state. In an alternative aspect, the IOL in the ocular system has no inherent spherical aberration, thus minimizing induced aberrations such as coma and astigmatism due to lens misalignment. In a further aspect, the IOL in the ocular system has an amount of inherent positive spherical aberration.

Another embodiment of the invention is directed to a method for designing a family of aspheric IOLs that includes a plurality of individual aspheric IOLs each having a lens power and each having a different value of inherent spherical aberration, involving the steps of determining a lens constant that is the same for each of the plurality of individual IOLs, and providing a lens shape factor that is different for each of the plurality of individual IOLs for maintaining the same lens constant. According to an aspect, the design method provides a child-IOL or a family of child-IOLs having selection-based labeling parameters of lens power and lens constant that are the same as a respective spherical parent-IOL or family of spherical parent-IOLs, which have already received necessary approval from an appropriate governmental agency or regulating authority as the case may be.

Another embodiment of the invention is directed to a multi-component accommodating intraocular lens (A-IOL). The A-IOL includes an anterior lens component having a first (1), anterior surface and a second (2), posterior surface; a posterior lens component having a third (3), anterior surface and a fourth (4), posterior surface; and a biasing element operably coupling the anterior lens component and the posterior lens component. The biasing element allows the anterior lens component to translate along an optical axis relative to the posterior lens component. According to a particular aspect of the embodiment, at least one of the surfaces will be aspheric. As such, the A-IOL will introduce substantially no residual spherical aberration to a wavefront incident upon and passing through the A-IOL. According to an aspect, the A-IOL will have substantially no inherent spherical aberration. In a particular aspect, the anterior lens component will have substantially no inherent spherical aberration and the posterior lens component will have substantially no inherent spherical aberration. In another particular aspect, the anterior lens component will have a finite amount of inherent spherical aberration, $SA_A$, and the posterior lens component will have an equal amount of inherent spherical aberration, $SA_P$, of opposite sign to that of the anterior lens component, such that the A-IOL will have no overall inherent spherical aberration. According to another aspect, at least three of the surfaces of the A-IOL will be aspheric. More particularly, the at least three aspheric surfaces will be rotationally symmetric. In another aspect, the posterior lens component may have a diffractive, Fresnel or other discontinuous type optical surface. These alternative types of posterior lens surfaces or posterior optical components may be advantageous in controlling a physical characteristic such as, for example, size, shape, volume and/or thickness of the A-IOL. This degree of control may offer resultant advantages that include standardization of an A-IOL characteristic over a family of A-IOLs to realize efficiencies in the manufacturing and/or surgical application of the A-IOLs. In a related aspect of the embodiment, the alternative diffractive, Fresnel or other discontinuous type surface(s) may advantageously be incorporated into an A-IOL as described herein that does not have any non-spherical surfaces and which, therefore, does not provide the selective spherical aberration control obtainable with one or more aspheric surfaces.

Another embodiment of the invention is directed to a family of multi-component accommodating intraocular lenses (A-IOLs) that includes a plurality (at least two) of member A-IOLs, each having a different optical power. The A-IOL family extends over at least a portion of a power range, and will be considered a family for all serial member A-IOLs that differ in overall optical power by a constant power differential (e.g., a consistent power differential between 0.25D to 15.0D). According to a particular aspect of the embodiment, at least one surface of each member A-IOL of the family will be aspheric, and each member A-IOL will introduce substantially no residual spherical aberration to a wavefront passing through the member A-IOL. Each member A-IOL will have the characteristics of the various A-IOL embodiments and aspects thereof described above. According to an aspect, each member A-IOL of a family will have a first (1) surface and a fourth (4) surface characterized by respective radius and conic constant values that remain substantially constant over the power range of the A-IOL family. This feature would present an advantageous benefit relating to increased efficiency in the manufacture of A-IOLs by reducing the number and/or complexity of lens mold components, for example. In a related aspect of the embodiment, the member A-IOLs may comprise all spherical surfaces while maintaining first and fourth surfaces characterized by respective radius values that remain substantially constant over the power range of the A-IOL family. This feature shares the potential benefit of increased molding efficiency referred to immediately above. According to another aspect, each posterior lens component of the member A-IOLs may be characterized by an edge thickness, a center thickness, a cross sectional area and/or a lens volume (overall, lens size) that remains generally constant over the power range of the A-IOL family. Such a condition may be advantageous in relation to the use of standardized lens injectors, for example. More particularly, the posterior lens components of at least some of the member A-IOLs of the family may be of a diffractive optical design. In an alternative aspect, an A-IOL surface may be a Fresnel surface. These features are applicable to A-IOLs having all spherical surfaces as well as to A-IOLs having one or more aspheric surfaces.

In another embodiment, an A-IOL will have a finite amount of inherent negative spherical aberration. In a particular aspect, the finite amount of inherent negative spherical aberration will be less than an amount required to balance the inherent positive spherical aberration of the cornea. According to an aspect, the amount of the inherent positive spherical aberration of the cornea will be determined from a statistically significant subject population to determine an average value of inherent positive corneal spherical aberration. In a particular variation of this aspect, the A-IOL will have an inherent amount of negative spherical aberration that mimics the inherent spherical aberration of a healthy, natural crystalline lens in a relaxed state; i.e., between about negative (−)0.13 micron (µ) to negative (−)0.07µ of spherical aberration. In a more particular variation of this aspect, the A-IOL will induce about negative (−)0.1µ of spherical aberration in a converging wavefront propagating from the cornea through the A-IOL.

According to a related embodiment, a family of A-IOLs will comprise a plurality (at least two) of member A-IOLs. Each member A-IOL will be as described in the embodiment immediately above; i.e., each member A-IOL have a finite amount of inherent negative spherical aberration, however, each member A-IOL will have a respective power that differs from an adjacent member A-IOL of the family by a constant power differential as described above.

In another embodiment, the power of the posterior lens element of an A-IOL as referred to in the embodiments above is kept constant and the power of the anterior lens element varies to achieve the desired A-IOL power. Due to the variable anterior lens element power, the accommodative amplitude per millimeter of anterior lens translational movement will increase with A-IOL power. This feature is applicable to A-IOLs having all spherical surfaces as well as to A-IOLs having one or more aspheric surfaces.

In all of the recited embodiments, lens materials may include silicone, PMMA, hydrophilic acrylics, hydrophobic acrylics, natural or artificial collagens, or urethane. Particular silicones may have an index of refraction of between 1.40 to 1.60 and, in a particular aspect, equal to about 1.43. In a particular hydrophilic acrylic aspect, the index of refraction is about 1.46.

The disadvantages, shortcomings and challenges in the current state of the art, as well as the recited objects and advantages and others are addressed and met by embodiments of the invention described below with reference to the detailed description and drawings that follow, and by embodiments of the invention as defined in the appended claims.

BRIEF DESCRIPTION OF THE DRAWINGS

FIGS. 20-23 are tables showing lens parameters for an equiconvex spherical lens family, a biconvex spherical lens family, a biconvex aspherical lens family according to an embodiment of the invention, and an equiconvex aspherical lens family according to an embodiment of the invention;

FIGS. 29A-29D are lens parameter tables for each of the member A-IOLs, respectively, shown in FIGS. 28A-D;

FIG. 30 is an Excel formatted spreadsheet listed comparative lens parameter values according to an embodiment of the invention;

FIGS. 33A-33D are lens parameter tables for each of the member A-IOLs, respectfully, shown in FIGS. 32A-D;

FIGS. 34A-34D are MTF comparison curves at two optical vergence values for each of the member A-IOLs, respectfully, shown in FIGS. 32A-D;

FIGS. 36A-36D are lens parameter tables for each of the member A-IOLs, respectfully, shown in FIGS. 35A-D.

DETAILED DESCRIPTION OF A PREFERRED EMBODIMENT OF THE INVENTION

Embodiments of the invention described below relate to an aspheric lens for use in an optical system, in which the lens has physical and optical characteristics that control the spherical aberration in a wavefront passing through the lens. For the reader's clarity, the lens will be described in terms of an intraocular lens (IOL) for use in a human ocular system. In particular, the ocular system will be a pseudophakic ocular system; that is, an ocular system in which the natural crystalline lens has been removed and replaced with an implanted IOL. It is to be recognized, however, that the various embodiments of the invention apply to a phakic IOL system in which the natural crystalline lens of the ocular system has not been removed. Most generally, embodiments of the invention are directed to an aspheric lens for use in an optical system, in which the lens is designed to control spherical aberration. As used herein, the term aspheric lens refers to a lens having at least one aspheric surface that may be rotationally symmetric or asymmetric.

Figure 1:
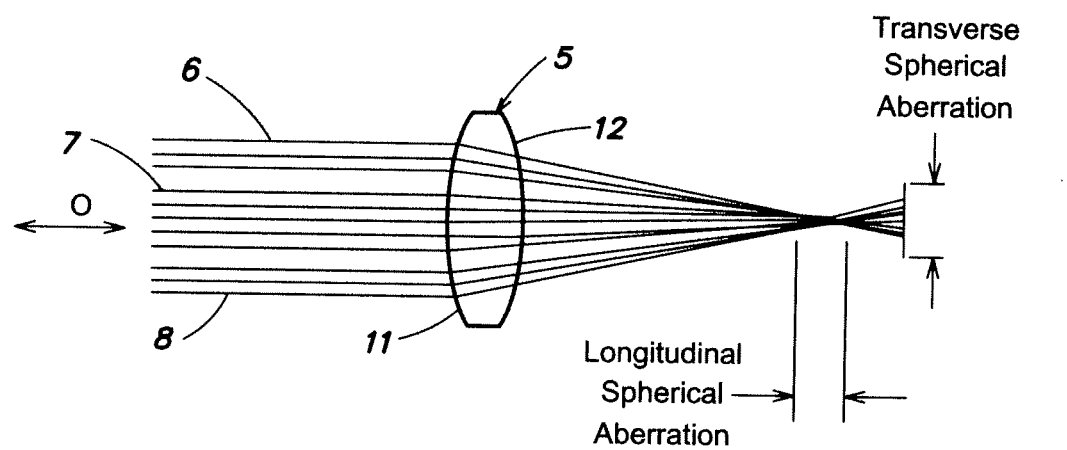
FIG. 1 is a diagrammatic illustration of a spherical lens having inherent spherical aberration.
Figure 2:
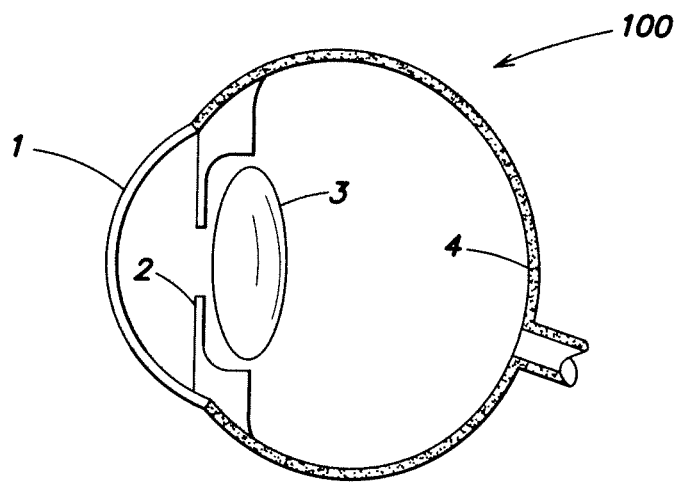
FIG. 2 is a schematic illustration of a human ocular system.
Figure 3:
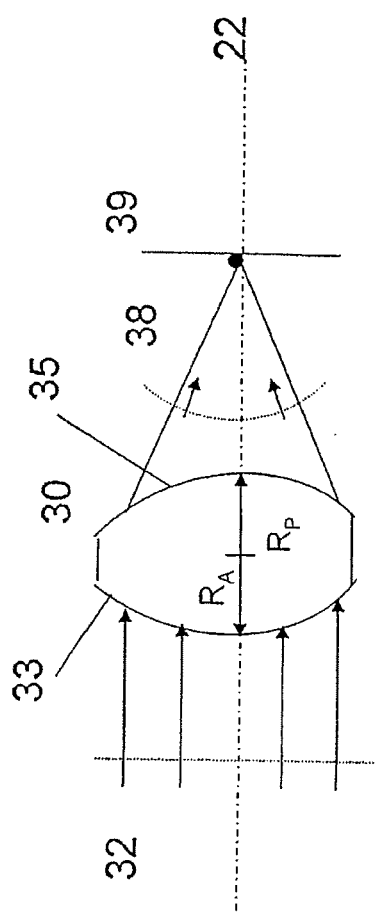
FIG. 3 is a schematic illustration of an aspheric IOL according to an embodiment of the invention.

An embodiment of the invention is directed to an aspheric IOL characterized in that the lens has a shape factor that induces substantially no spherical aberration to a wavefront of light passing through the lens. An aspect of the embodiment is illustrated in FIG. 3, which shows a plane wavefront 32 on an object side of the lens incident upon IOL 30. The IOL 30 has an anterior surface 33 and a posterior surface 35, at least one of which is an aspheric surface characterized by a conic constant and an apical radius of curvature. The lens 30 has positive optical power and focuses the wavefront 38 to a point on the optical axis at image plane 39. The lens surface asphericity is such that substantially no additional positive or negative spherical aberration is introduced into the wavefront 32 by lens 30. The lens 30 by definition has no inherent spherical aberration.

The physical characteristics of lens 30 include the apical or vertex radii of curvature, $R_a$, for the anterior surface and $R_p$ for the posterior surface, and the surface shape, or SAG, of the anterior and posterior surfaces. The SAG of an optical surface is expressed by the well-known equation $$SAG=(x^2/R_v)/1+[1-(1+k)(x^2/R^2v)]^{1/2}$$

where x is the radial distance from the point at which the lens surface intersects the optical axis 22 (where x equals 0) to another point on the lens surface; $R_v$ is the vertex radius of curvature of the lens surface and k is the conic constant. For a hyperbola, $k<-1$; for a parabola, $k=-1$; for a prolate ellipse, $-1<k<0$; for a sphere, $k=0$; for an oblate ellipse, $k>0$. Table 2 lists the physical and optical characteristics of a typical equiconvex IOL and an exemplary aspheric IOL according to an embodiment of the invention, both having a lens power of 20D. As shown in Table 2, the exemplary IOL has equal apical radii of curvature and the conic constant of both surfaces is the same. Table 3 compares the parameters of the prior mentioned spherical LI61U IOL with another exemplary spherical aberration-free aspheric IOL according to an embodiment of the invention.

In various aspects, the IOL 30 may have various shape factors including equiconvex, biconvex, plano-convex, equiconcave, biconcave or meniscus. One or both surfaces are aspheric and may or may not have the same conic constant value. Likewise, the apical radii of curvature may or may not be equal. In an exemplary aspect, the apical anterior radius, $R_A$, is not equal to the apical posterior radius of curvature, $R_p$, however the ratio of the radii remain constant over the power range of the lens.

By convention, the lens is inherently corrected for spherical aberration at a wavelength of light equal to 555 nm. The lens body may be made from a biocompatible, optically transparent polymeric chemical compound such as silicone, PMMA, hydrogel, a hydrophilic or hydrophobic acrylic, natural or artificial collagen, silicone acrylic or urethane. In a particular aspect, the IOL has a lens body made of silicone having an index of refraction, n, of between 1.40 to 1.60. In a particular aspect, the lens body is made of silicone having an index of refraction of about 1.43. In another aspect, the lens body is made of a hydrophilic acrylic having an index of refraction of about 1.46. The IOL has a paraxial power of between about −10D to +40D and, more particularly, between about +15D to +40D.

The advantages of the IOL embodiment described above will now be apparent to a person skilled in the art. Since the average cornea produces approximately 0.28 micron of positive spherical aberration over the central 6 mm and a healthy natural crystalline lens in a relaxed state provides about −0.1 micron of (negative) spherical aberration, the retinal image of an object will generally have a residual amount of positive spherical aberration. The advantages of having a finite amount of residual positive spherical aberration are known to include: an increased depth of focus, which in certain circumstances may partially compensate for loss of accommodation in a presbyopic eye; positive spherical aberration may help patients with hyperopic postoperative refraction; and modest amounts of positive spherical aberration may mitigate the adverse effects of chromatic aberration and higher order monochromatic aberrations. In addition, since the IOL 30 has no inherent spherical aberration, tilting or decentering of the lens within the range of normal viewing tolerance (up to about 1 mm displacement transverse to the visual axis of the eye and up to ±10 degrees of rotation) will introduce a minimum amount, and perhaps no, asymmetric aberrations such as coma and/or astigmatism, which typically are induced by the misalignment of a lens with a significant amount of either positive or negative spherical aberration. Spherical aberration can be compensated with spectacle correction, but asymmetrical aberrations, like coma, cannot. Thus, in a pseudophakic ocular system including IOL 30, the resulting retinal image will have residual positive spherical aberration but no induced coma or astigmatism. An exemplary prescription of the inherent aberration free lens is as follows:

$R_a$=8.014 mm
$R_p$=−10.418 mm
$k_a$=$k_p$=−1.085657
Center thickness (CT)=1.29 mm Inherent spherical aberration (Z400)=0 micron over a 5 mm aperture. When this lens is placed 4.71 mm behind a perfect optical element with a power of 43D (e.g., a cornea with average power and no spherical aberration), the resulting wavefront has 0.0167μ of spherical aberration. When this lens decenters 0.5 mm, 0μ of coma and astigmatism are induced. The exemplary lens has an effective focal length (EFL) equal to 50 mm (i.e., 20D lens), an edge thickness of 0.3 mm for a radial position of 3 mm, and a refractive index of 1.427. The ratio between the apical radii of the anterior and posterior surfaces is −1.3 (i.e., $R_p$=−1.3 $R_a$). The ratio between the conic constants of the anterior and posterior surfaces is 1 (i.e., $k_a$=$k_p$).

A study was performed using a sophisticated ray tracing program (ZEMAX, Focus Software) to evaluate the effects of lens decentration on the optical designs of three silicone IOLs in an experimental model eye: the LI61U (conventional spherical IOL), the Tecnis Z9000 (aspheric IOL) and the inherent aberration free IOL described as IOL 30 above. The study was carried out using pupil diameters of 3 mm, 4 mm and 5 mm and lens decentrations of 0, 0.25, 0.5, 0.75 and 1.0 mm. The modulation transfer functions (MTFs) were computed and plotted. A Monte Carlo simulation analysis with one thousand trials was performed with lens decentration randomly varying for each pupil size. Various reasons for lens decentration include: in-out of the bag placement, incongruency between bag diameter and overall diameter of lens, large capsulorhexis, asymmetrical capsular coverage, lens placement in sulcus, capsular fibrosis, capsular phimosis and radial bag tears. Even if the lens is perfectly centered, the other optical components of the human eye are very rarely, if ever, centered on the visual axis or any common axis. The optical performance of each IOL was evaluated in a theoretical model of a pseudophakic eye. Details about the theoretical model eye can be found in U.S. Pat. No. 6,609,793, the teachings of which are herein incorporated by reference in their entirety to the fullest allowable extent. In addition, a Gaussian apodization filter was placed in the entrance pupil to simulate the Stiles-Crawford effect. In the eye model, the positive spherical aberration of the single surface model cornea matched the average value measured in recent clinical studies. The Z(4,0) Zernike coefficient for spherical aberration for the average cornea is approximately 0.28 microns over a 6 mm central zone. The model eye uses an anterior chamber depth of 4.5 mm, which matches the measurements of IOL axial positioning in pseudophakic eyes. The optical prescription of the model eye is given in Table 4.

In this study, each of the IOLs was a silicone lens having a power of 22D. Each lens was evaluated by centering the lens in the theoretical model eye such that the anterior surface of the IOL was 0.9 mm behind the iris. For each combination of lens model and pupil diameter, the distance between the posterior surface of the IOL and the retina was optimized to obtain the best optical performance for an on-axis object located at infinity at a wavelength of 555 nm. When an IOL is perfectly centered, only axial aberrations (e.g., spherical aberration) of the model cornea and the lens itself degrade the image on the model retina. Each IOL was successfully decentered in the tangential plane by 0.25 mm, 0.50 mm, 0.75 mm and 1.0 mm. The cornea, pupil and retina were always centered on the optical axis of the theoretical model eye. An array of 512×512 (262,144) rays was traced and the MTF was computed for each simulation. The resultant tangential and sagittal MTF curves over a spatial frequency range of 0 to 60 cycles/degree (cpd) were plotted for each simulation.

3 mm Pupil

Figure 5:
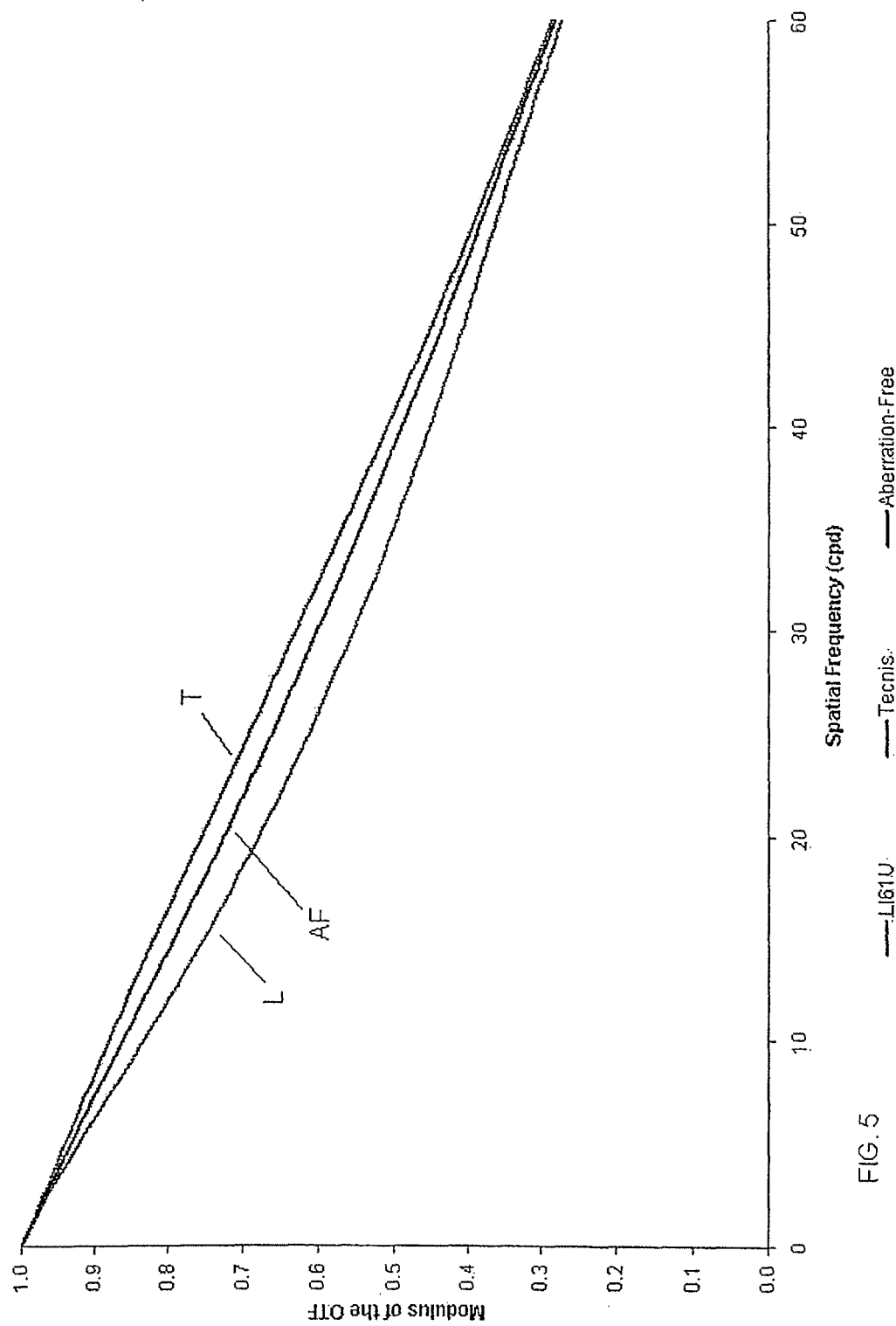
FIGS. 5, 6 and 7 are MTF curves for decentering values of three comparative IOLs in a theoretical pseudophakic model eye with a 3 mm pupil.
Figure 6:
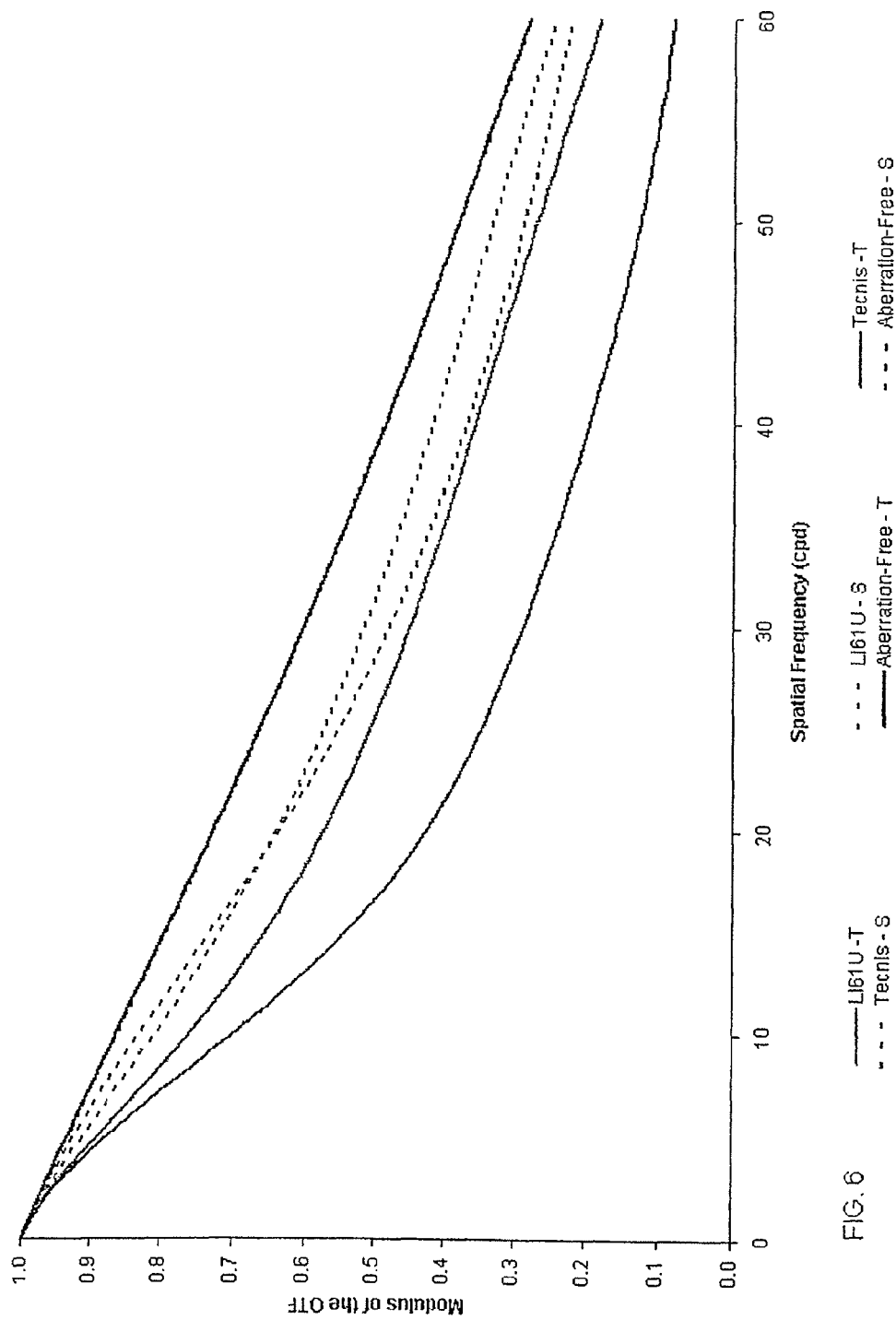
Figure 7:
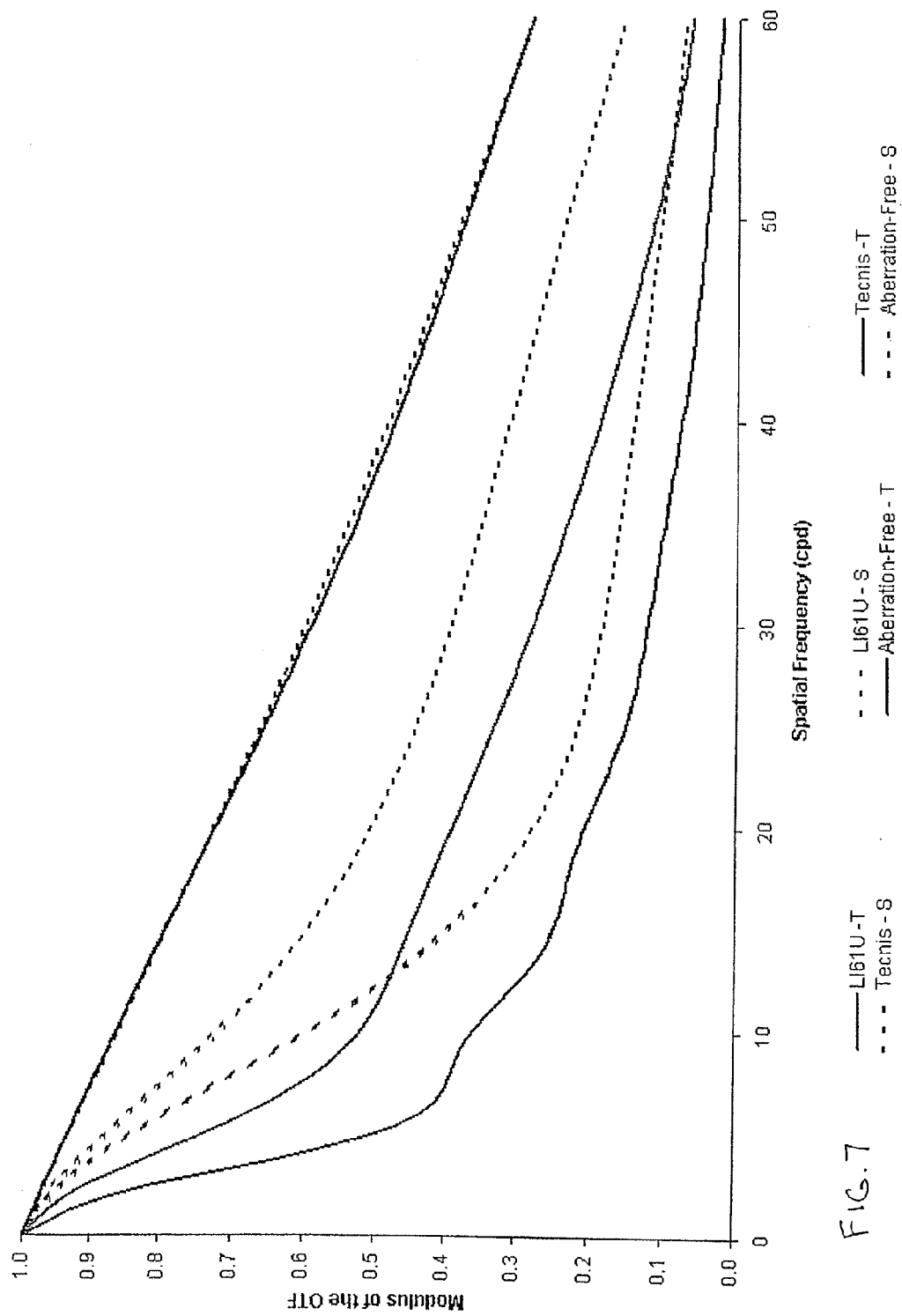

For a 3 mm. pupil, the adverse effects of the spherical aberration of the cornea and the lens are small. The Z(4,0) coefficient for corneal spherical aberration was 0.016 microns. The centered performance of the model eye with any of the three lenses is near diffraction limited, as shown in FIG. 5. As the lenses decenter, the performances of the model eyes with LI61U and Z9000 lenses degrade, but the performance with the aberration free lens does not, as shown in FIGS. 6 and 7. Since the LI61U and Z9000 have inherent spherical aberration, higher order, asymmetrical aberrations are created when the lens is decentered, causing the tangential and sagittal MTF curves to separate and droop.

The aberration free lens was determined to outperform the LI61U over all spatial frequencies for all lens decentrations. When the aberration free lens was decentered 1 mm, it continued to outperform a perfectly centered LI61U lens, and it outperformed the Z9000 lens, decentered by only 0.15 mm.

4 mm Pupil

Figure 8:
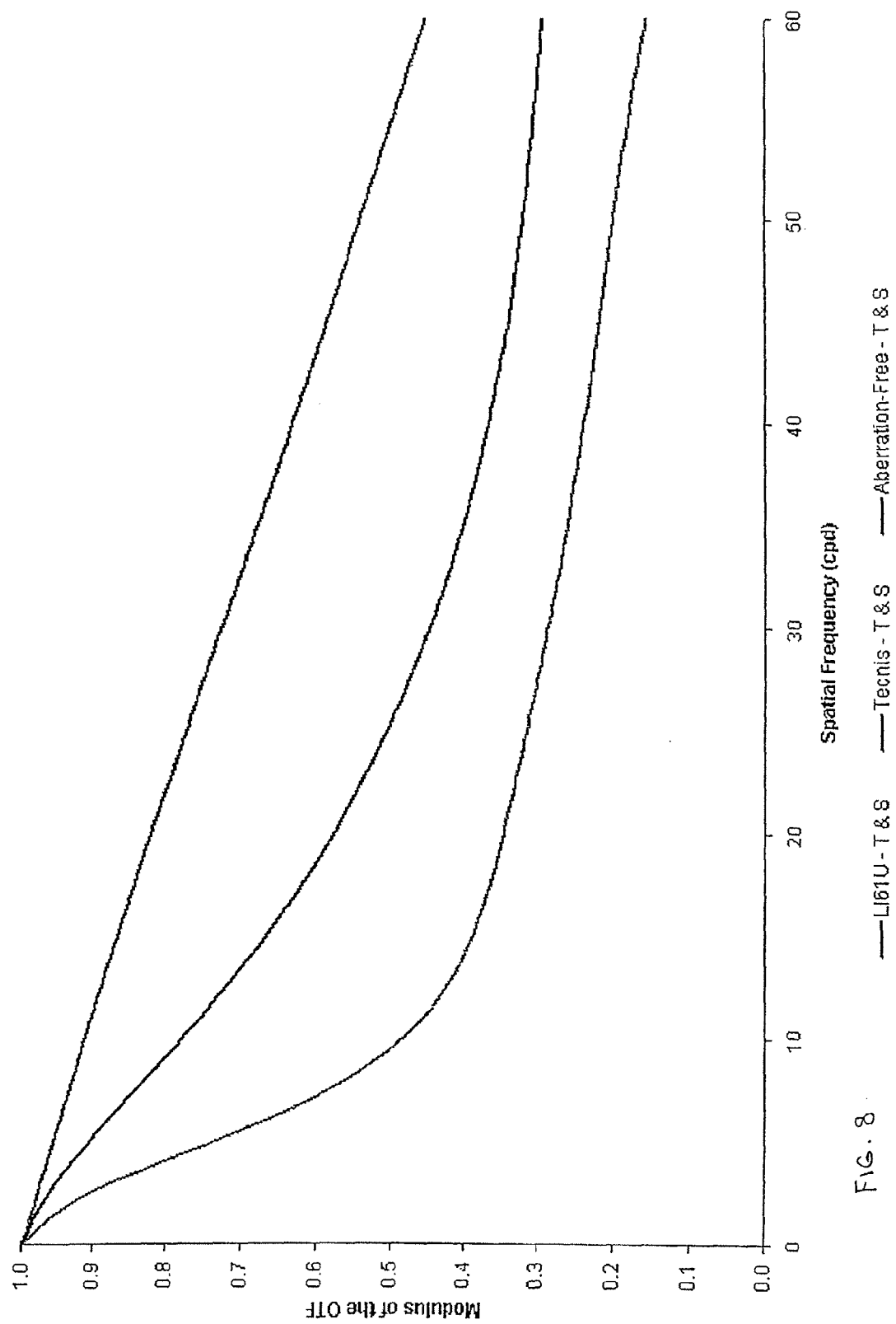
FIGS. 8, 9 and 10 are MTF curves for decentering values of three comparative IOLs in a theoretical pseudophakic model eye with a 4 mm pupil.
Figure 9:
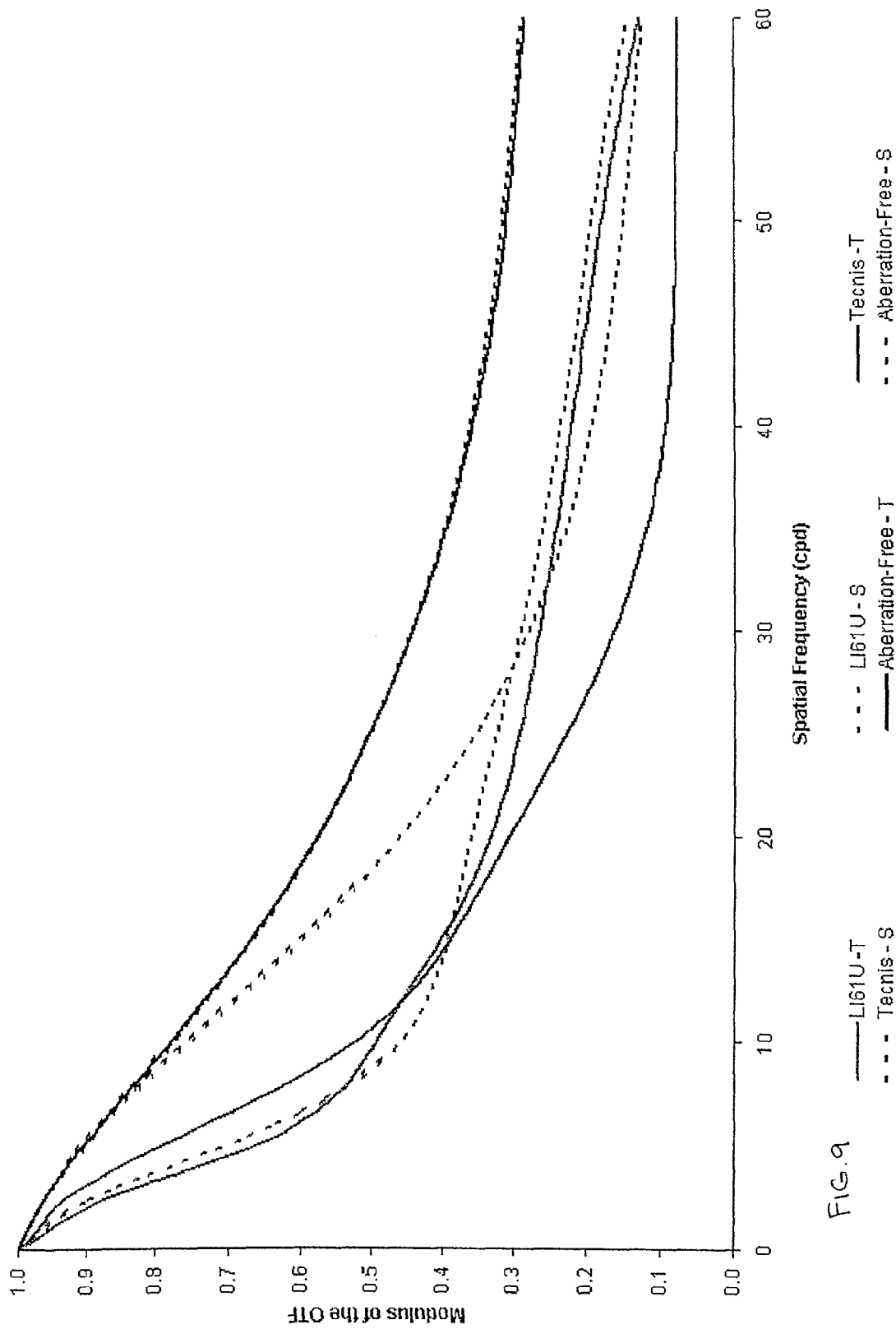
Figure 10:
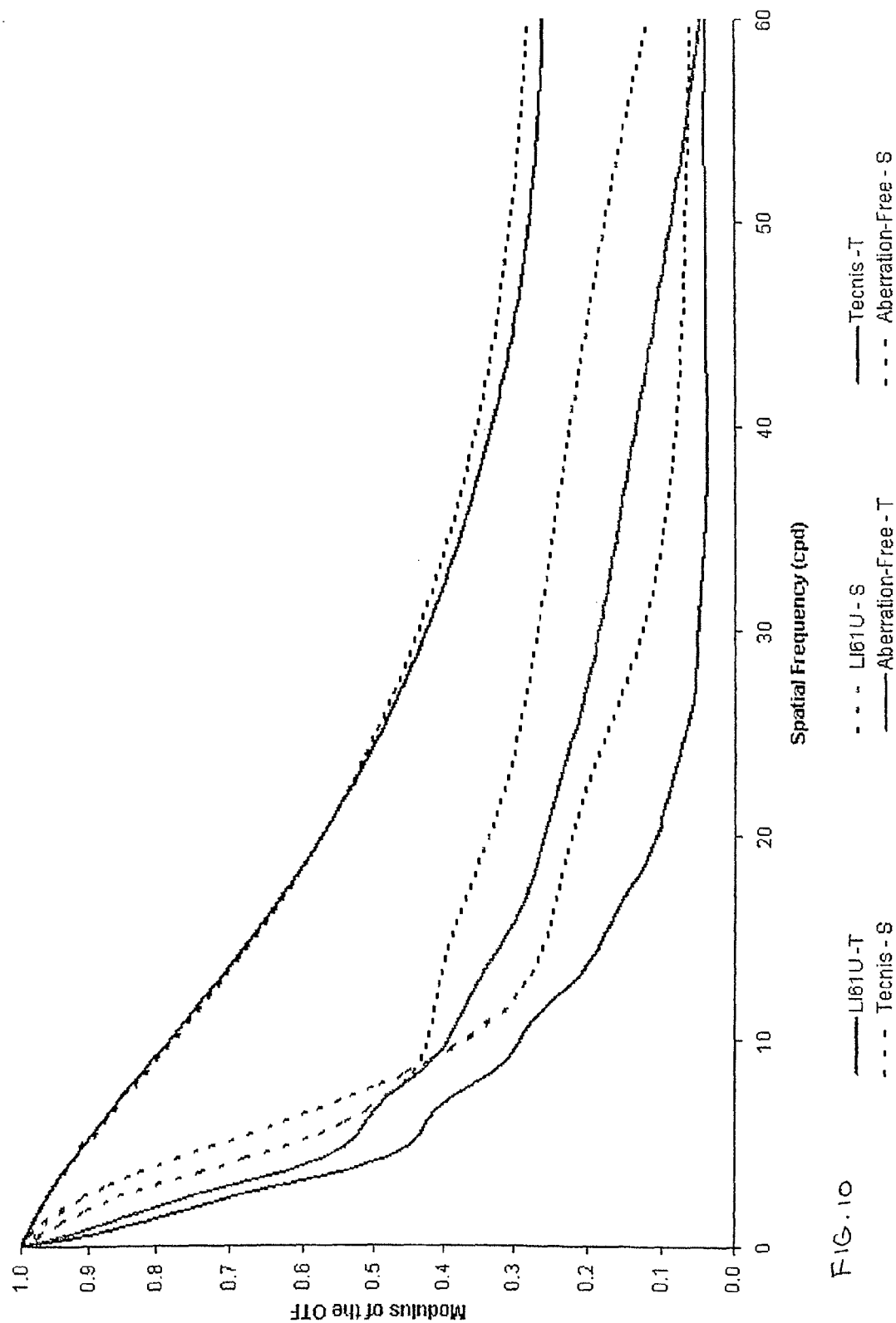

For a 4 mm pupil, the adverse effects of the spherical aberration of the cornea and the lens are more problematic. The Z(4,0) coefficient for corneal spherical aberration is 0.051 micron. When the lenses are perfectly centered, the performance of the model eye with the Z9000 is diffraction limited by design as show in FIG. 8. The performance of the model eye with the aberration free lens is reduced by spherical aberration of the cornea, and the performance of the LI61U is further reduced by the inherent positive spherical aberration of the lens. As the lenses are decentered, the performance of the model eyes with LI61U and Z9000 lens degrade, but the performance with the aberration free lens remains steady, as shown in FIGS. 9 and 10.

Similar to the 3 mm pupil case, the aberration free lens outperforms the LI61U over all spatial frequencies for all lens decentrations. The aberration free lens outperforms the Z9000 lens for all spatial frequencies if the lens decentration exceeds 0.3 mm. Even if the aberration free lens decentered 1 mm, it outperforms the Z9000 lens decentered by only 0.3 mm.

5 mm Pupil

Figure 11:
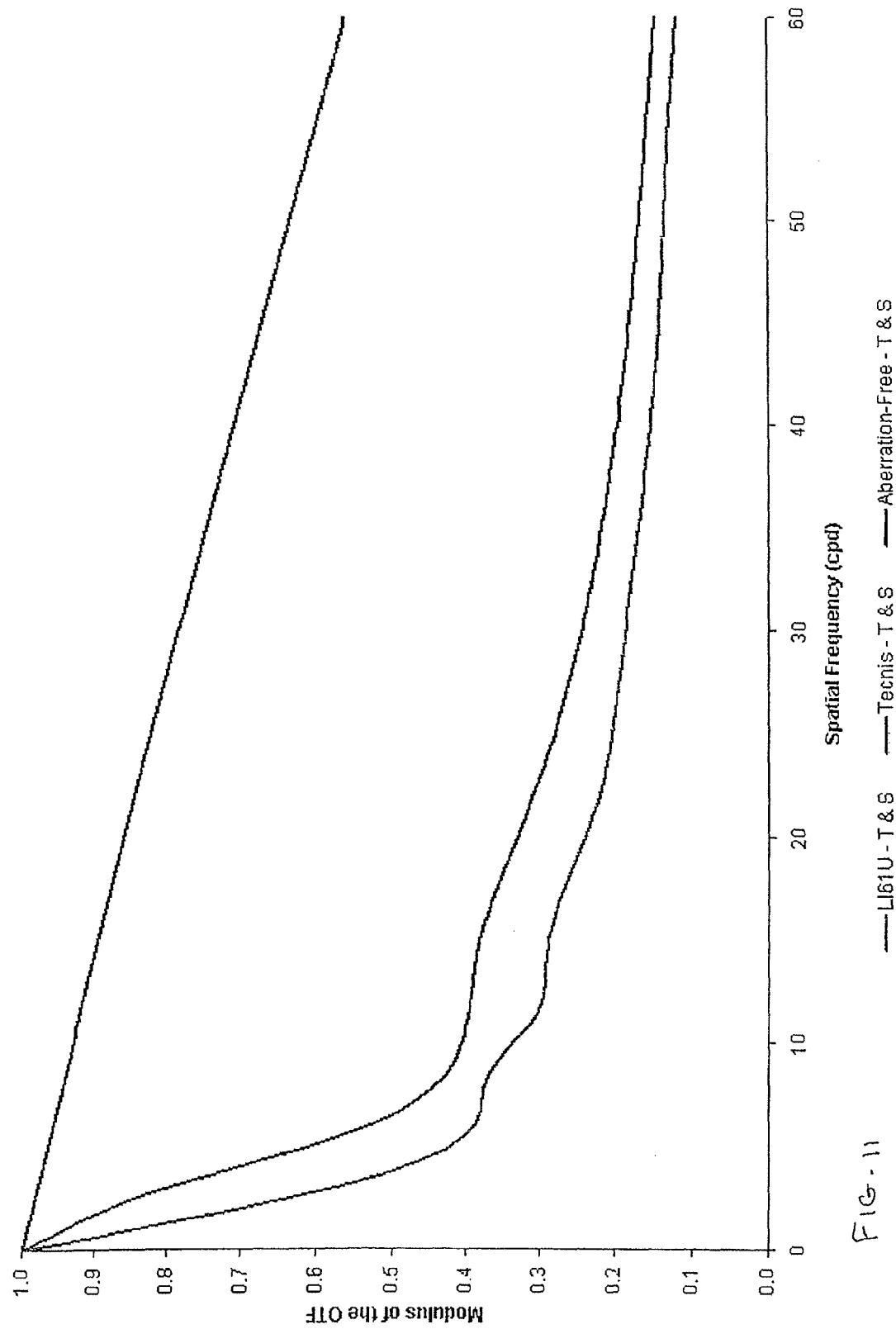
FIGS. 11, 12 and 13 are MTF curves for decentering values of three comparative IOLs in a theoretical pseudophakic model eye with a 5 mm pupil.
Figure 12:
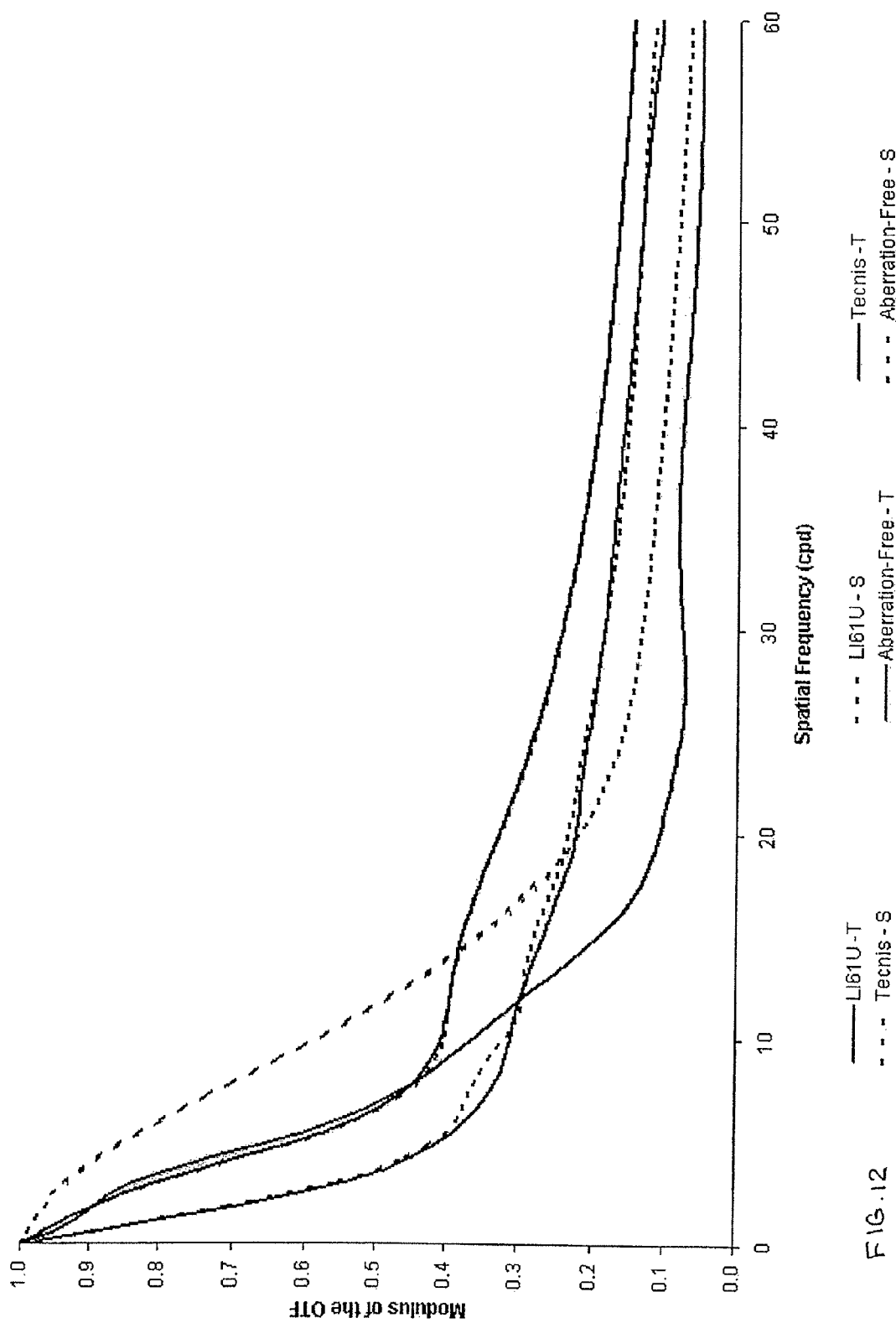
Figure 13:
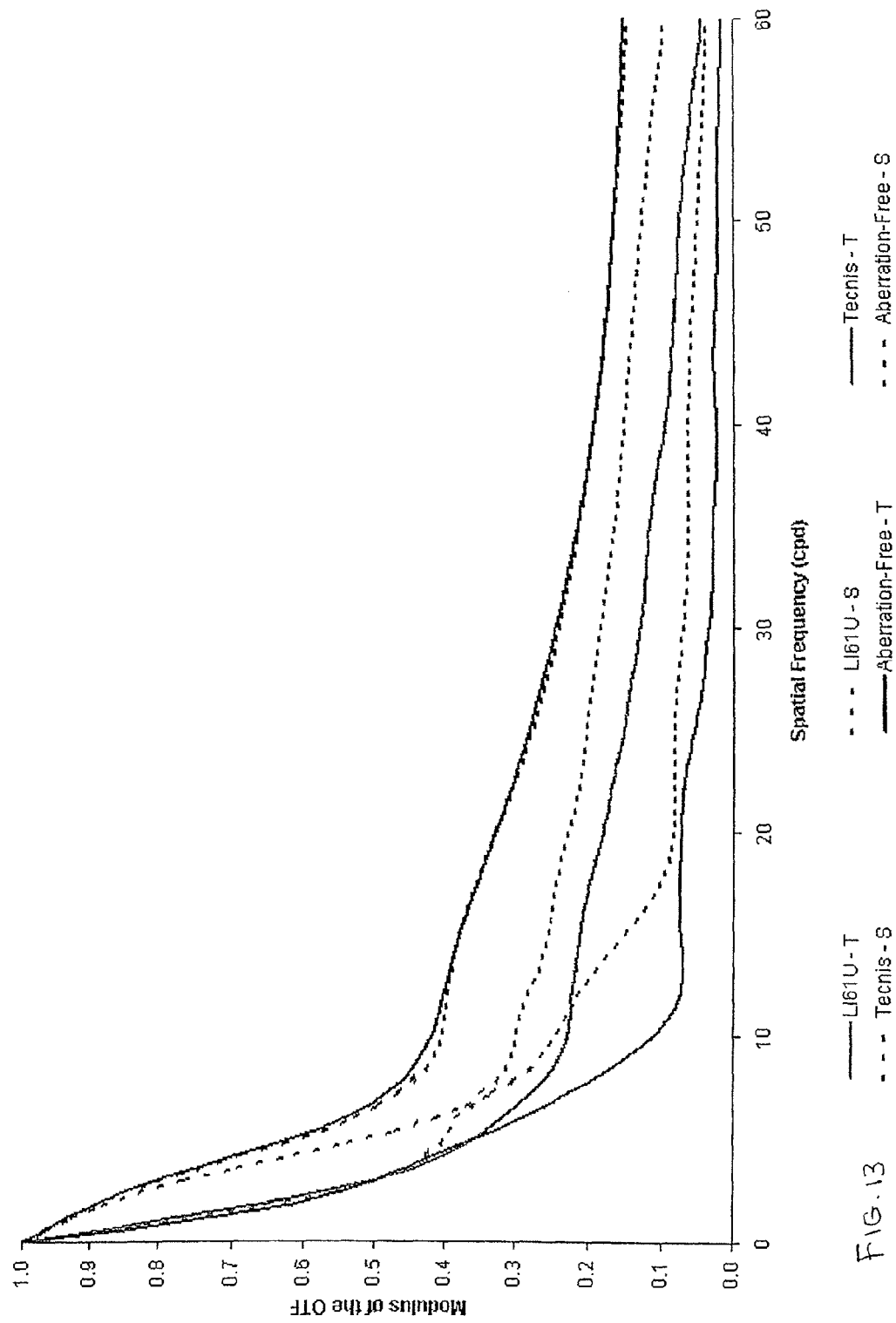

For a 5 mm pupil, the adverse effects of spherical aberration of the cornea and lens are most significant. The Z(4,0) coefficient for corneal spherical aberration is 0.130 micron. When the lens are perfectly centered, the performance of the model eye with the Z9000 lens is diffraction limited by design, as shown in FIG. 11. The performance of the model eye with the aberration free lens is reduced by the spherical aberration of the cornea, and the performance with the LI61U is further reduced by the inherent spherical aberration of the lens. As the lenses decenter, the performance of the model eye with LI61U and Z9000 lens degrade, but the performance with the aberration free lens does not, as shown in FIGS. 12 and 13.

In this case, the aberration free lens outperforms the Z9000 lens if the lens decentration exceeds 0.38 mm. Even if the aberration free lens is decentered 1 mm, it outperforms the Z9000 lens decentered only 0.38 mm.

Monte Carlo Analysis

Figure 14:
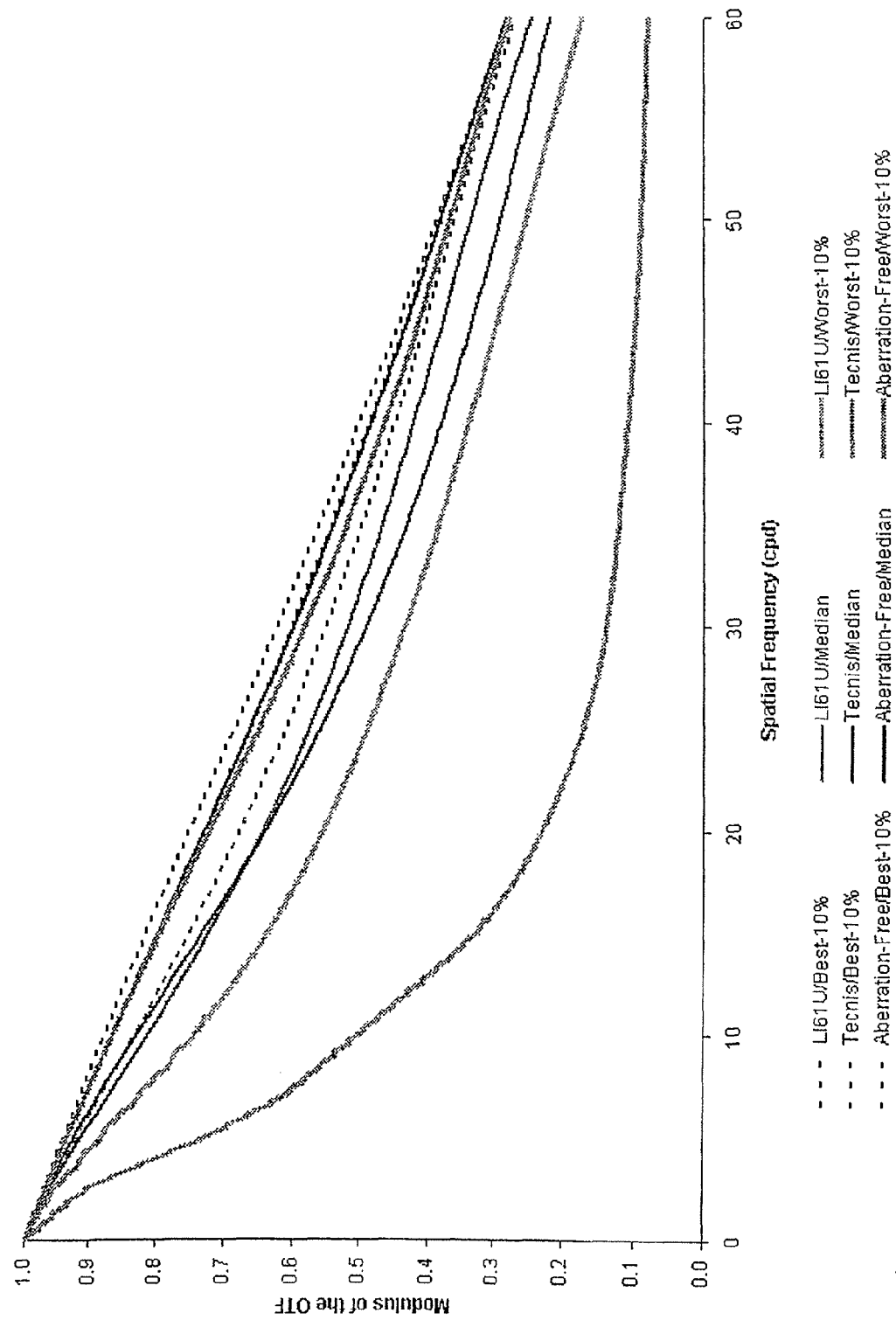
FIGS. 14, 15 and 16 are MTF curves of a Monte Carlo analysis for three comparative IOLs in a theoretical pseudophakic model eye with a 3 mm, 4 mm and 5 mm pupil, respectively.
Figure 15:
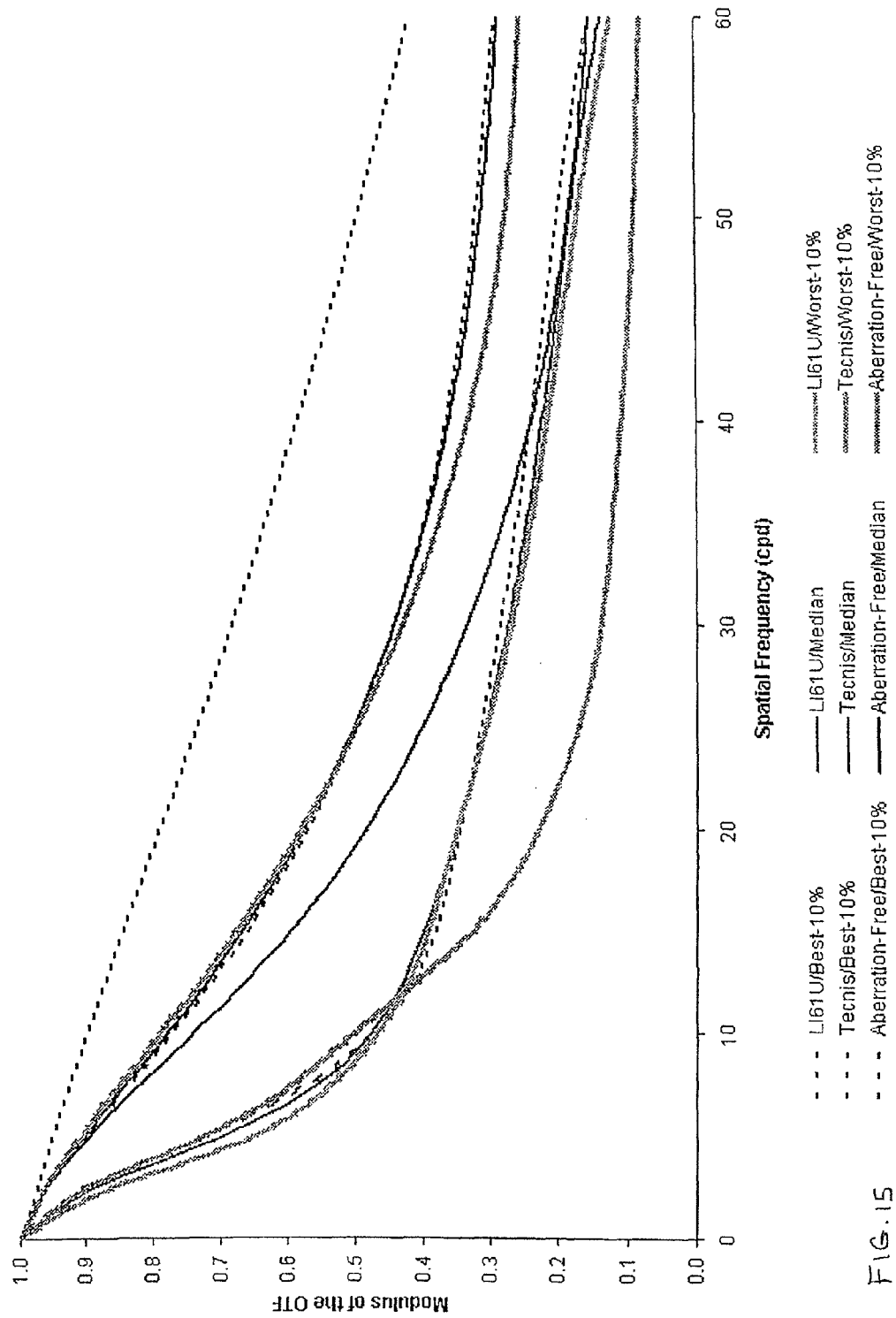
Figure 16:
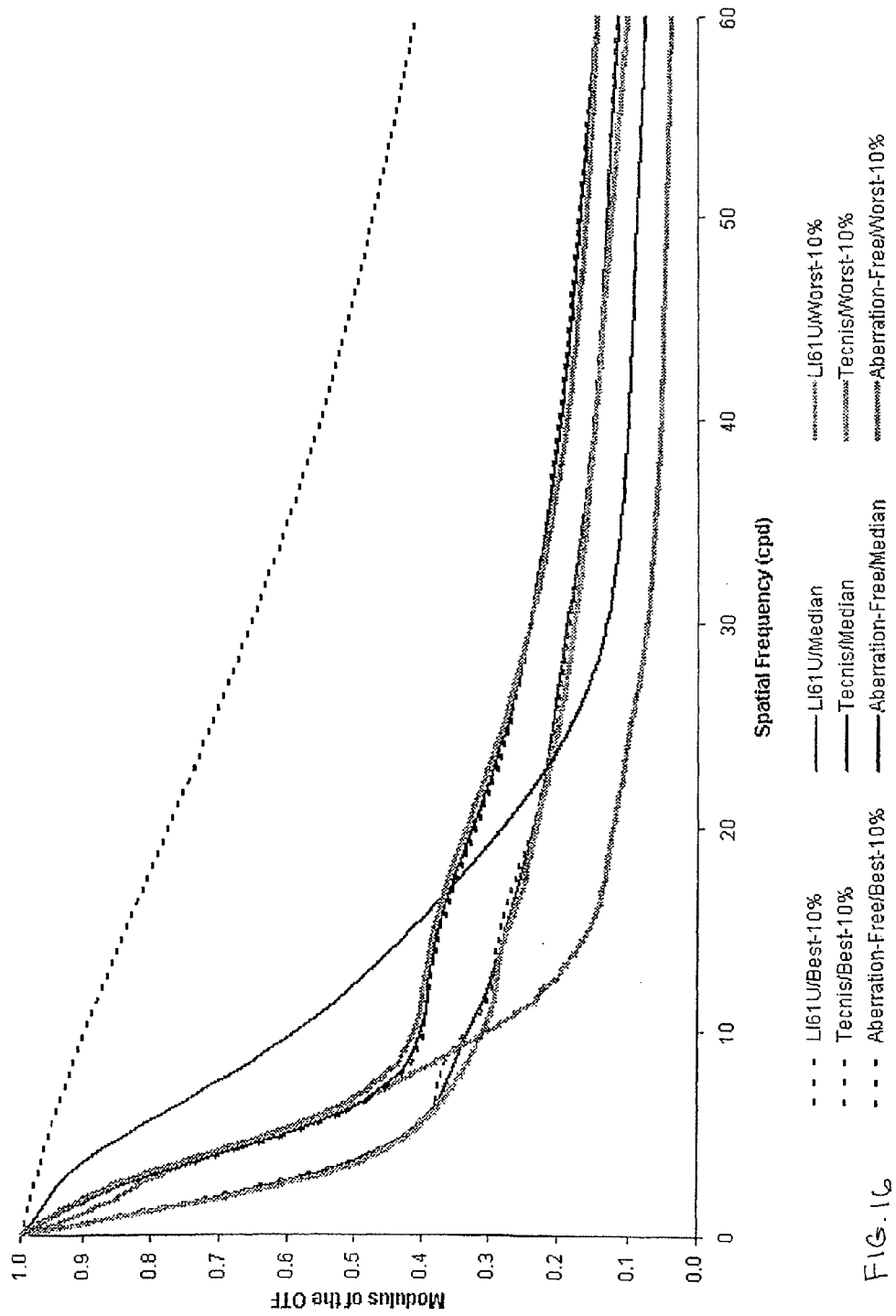

The averages of the tangential and sagittal MTF curves for 3 mm, 4 mm and 5 mm pupil diameters are shown on FIGS. 14-16, respectively. For each lens model, the MTF curves for the worst 10 percent, best 10 percent and median cases are shown. Because the performance of the aberration free lens is independent of lens decentration, the worst 10 percent, best 10 percent and median MTF curves lie upon one another. Since the LI61U and Z9000 designs have inherent spherical aberration, their performances are dependent upon lens decentration, and thus the worst 10 percent, best 10 percent and median MTF curves are separated. Greater separation between the worst 10 percent and best 10 percent MTF curves indicates less repeatability and predictability in post-operative outcomes.

For a 3 mm pupil (FIG. 14), all of the MTF curves for the aberration free lens lie above the MTF curve for a perfectly centered LI61U and very nearly coincide with the best 10 percent MTF curve for the Z9000.

For a 4 mm pupil (FIG. 15), all of the MTF curves for the aberration free lens lie above the MTF curve for a perfectly centered LI61U and the median MTF curve for the Z9000.

For a 5 mm pupil (FIG. 16), all of the MTF curves for the aberration free lens lie above the MTF curve for a perfectly centered LI61U, meaning the aberration free lens outperforms the LI61U in 100% of the cases. In the majority of cases, the aberration free lens outperforms the Z9000 for spatial frequencies greater than 17 cpd.

Figure 4:
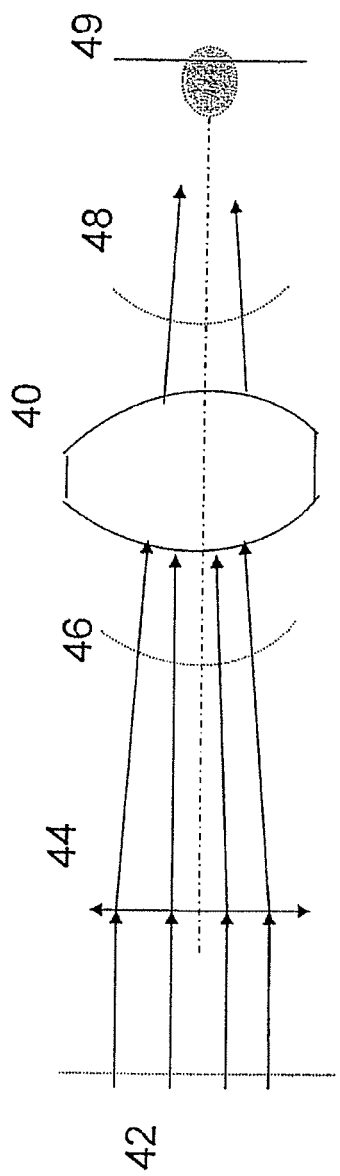
FIG. 4 is a schematic illustration of an aspheric IOL according to an embodiment of the invention.

According to another variation of the embodiment described above, an aspheric IOL has a shape that induces no spherical aberration to a converging wavefront incident from a focusing element on an object side of the lens as the wavefront passes through the IOL. FIG. 4 schematically shows a pseudophakic ocular system including focusing element 44, aspheric IOL 40 and image plane 49. The focusing element 44 is representative of the cornea of the eye and image plane 49 is the retinal image plane of the ocular system. A plane wavefront 42 from an infinitely distant object is transformed into a converging wavefront 46 by the positive optical power of cornea 44. Converging wavefront 46 has positive spherical aberration induced by the cornea. The IOL 40 is characterized in that no spherical aberration is added to or subtracted from the converging wavefront 46 passing through the IOL. Thus, the converging wavefront 48 incident on the retinal image plane 49 will have a finite amount of residual positive spherical aberration produced by the cornea. In this embodiment, the IOL 40 has a small amount of negative inherent spherical aberration, such that an incident convergent wavefront will be refracted without the addition of any spherical aberration. However, the IOL 40 has substantially less negative inherent spherical aberration than the Z9000 lens referred to above. In an aspect, the aspheric IOL 40 will compensate for less than 50% of the spherical aberration created by the cornea. An exemplary prescription for the converging aberration-free lens is as follows:

$R_a$=8.014 mm
$R_p$=−10.418 mm
$k_a$=$k_p$=−1.449

Center thickness (CT)=1.28 mm (CT is reduced 10μ over aberration free lens described above);

Inherent spherical aberration (Z400)=−0.0327 micron over a 5 mm aperture. When this lens is placed 4.71 mm behind a perfect optical element with a power of 43D (e.g., a cornea with average power and no spherical aberration), the resulting wavefront has 0μ of spherical aberration. However, when this lens decenters 0.5 mm, only 0.016μ of coma and 0.0115μ of astigmatism are induced. These amounts of coma and astigmatism are small, and their adverse effects on retinal image quality will not be significant.

In a particular variation of the IOL 40, the IOL has at least one aspheric surface that induces an amount of negative spherical aberration substantially equivalent to that of a healthy natural crystalline lens in a relaxed state. Thus, the lens will induce between about −0.13μ to −0.07μ of spherical aberration to a converging wavefront incident upon and refracted by the lens. In a more particular aspect, the lens surface shape is adjusted such that the lens induces about −0.1μ of spherical aberration to the converging wavefront. An exemplary prescription for the equivalent natural lens is as follows:

$R_a$=8.014 mm
$R_p$=−10.419 mm
$k_a$=$k_p$=−2.698399

Center thickness (CT)=1.2492 mm (CT is reduced by 41μ over aberration free lens described above);

Inherent spherical aberration (Z400)=−0.135 micron over a 5 mm aperture. When this lens is placed 4.71 mm behind a perfect optical element with a power of 43D (e.g., a cornea with average power and no spherical aberration), the resulting wavefront has −0.0877μ of spherical aberration. However, when this lens decenters 0.5 mm, 0.1428μ of coma and 0.0550μ of astigmatism are induced.

Another embodiment of the invention is directed to a family of aspheric IOLs. The family may consist of any two or more individual aspheric IOLs having different values of inherent spherical aberration and having a lens constant (A-constant) value that is the same for all of the lenses in the family. This can be achieved by providing a different lens shape factor for each lens having a different spherical aberration value. Different family constructs can be thought of as follows: a family may consist of a plurality of aspheric IOLs, which will have different spherical aberration values over a standard power range of −10D to 40D and more particularly over a power range of 15D to 40D. For reasons stated herein above, assume that the lens manufacturer wishes to designate this family of IOLs (the child-family) with the same A-constant as a family of standard equiconvex spherical IOLs (the parent-family) having spherical aberration values that increase as lens power increases. If the manufacturer were to keep the shape factor of the child-family of IOLs the same as the parent-family of spherical IOLs, then the A-constant should be changed, because, for each labeled paraxial power the true powers for the parent IOLs and child IOLs will be different. Hence, the manufacturer is faced with a dilemma of launching a lens with the same A-constant, which will cause post-operative refractive errors, or launch the child-family with a new A-constant (at additional labeling expense), which would cause confusion between surgeons who use both the parent spherical and child aspherical lenses. According to an embodiment of the invention, the A-constant can be maintained between the parent-family and the child-family by changing the shape factor of the child aspheric IOLs with respect to the parent spherical IOLs.

In a different scenario, a manufacturer may wish to launch a completely new family of IOLs having two or more lines (A, B, . . . ) where each lens line has a different value for spherical aberration. In this case, there is no parent-family of lenses. Line A may be assumed to have a spherical aberration value of A throughout the entire range of powers, and line B having a spherical aberration value of B throughout the entire range of powers. The range of powers will be the same for both lines. If the manufacturer wishes to keep the same lens shape factor for both lines, then the A-constant will have to be different for each line, again causing potential labeling changes and surgeon confusion. However, according to an embodiment of the invention, each line of lenses may be produced with a different lens shape factor, thus maintaining the A-constant the same for both lens lines.

A further scenario may involve a new family of aspheric IOLs having only a single line of lenses, but through different ranges of powers, there are distinct discontinuous shifts in the value of spherical aberration (i.e., not the continuous increase in spherical aberration as lens power increases for spherical lenses). According to an embodiment of the invention, the A-constant can remain the same throughout the full range of powers by changing the lens shape factor for each range of powers with different spherical aberration values.

In the cases recited above, it is intended that the parent-family of IOLs or any parent lens has already obtained FDA, CE or other government regulatory agency approval such that the child-family or child lens having the same power value and A-constant will get approval more efficiently than if the labeling parameters of the child-family are different than those of the parent-family.

In an illustrative aspect, a family of aspheric IOLs includes at least one aspheric IOL in a first group having an inherent negative value of spherical aberration; at least one aspheric IOL in a second group having a value of inherent spherical aberration substantially equal to zero; and at least one aspheric IOL in a third group having a value of inherent positive spherical aberration. More particularly, the value of inherent spherical aberration (i.e., the Z(4,0) Zernike coefficient using Born & Wolf notation) of the first group is in a range from less than zero to about −2.0 micron over a 6 mm pupil aperture while the inherent spherical aberration in the third group is in the range of greater than zero to about 1 micron over a 6 mm pupil aperture. Each group of lenses may have the same range of lens powers, but each of the at least one lenses in each group may have the same power or a different power.

According to an aspect, at least one of the aspheric IOLs in the first group having inherent negative spherical aberration is designed such that when it is used in a pseudophakic ocular system exhibiting a corneal focusing power of between about 37D to 49D, the IOL will induce no spherical aberration in a converging wavefront propagating from the cornea through the IOL. In a particular aspect, the IOL in the first group is designed so as to mimic the inherent spherical aberration of a healthy natural crystalline lens in a relaxed state such that the IOL induces between about −0.13 micron to −0.07 micron of spherical aberration to a converging wavefront of light propagating from the corneal focusing element through the lens. More particularly, the IOL will induce about −0.1 micron of spherical aberration. Thus, for all of the lenses in the first group, the resulting retinal image will have residual positive spherical aberration.

Each of the individual aspheric IOLs in the various families of lenses described herein are represented by lenses having the physical and optical characteristics of the lens embodiments described above. That is to say, each of the lenses has at least one aspheric surface characterized by a conic constant; the lens may have both anterior and posterior aspheric surfaces respectively characterized by conic constants in which the ratio of the anterior conic constant to the posterior conic constant is a constant value for all lens radii. Moreover, the apical radii of curvature of the lens play a key role in the position of the principle planes of the lens. It may be advantageous to maintain a fixed ratio between the anterior apical radius and the posterior apical radius that may or may not be equal to unity over the selected range of lens powers.

In summary, lenses described in accordance with the various embodiments of the invention control the effects of spherical aberration as a function of lens surface shape, and further, labeling characteristics of IOLs and IOL families can be made consistent between parent-families and child-families of lenses or within a family of lenses as a function of lens shape factor. The relationships between lens power, spherical aberration, lens constant and other lens variables can be further understood as follows.

As referred to above, an IOL is described by two parameters: lens power and A-constant. The extensive use of conventional equiconvex IOLs over many years enabled the development of regression formulae for selecting the power of an equiconvex IOL. The original SRK formula, developed around 1980, is $$\text{Power} = A - 2.5L - 0.9K$$

where Power is the power of the IOL to be implanted; A is the A-constant of the IOL; L is the axial length of the eye and K is the average keratometric power of the cornea. The axial length and average keratometry values are measured prior to surgery for use in the various formulae, the most recent of which continue to use a lens constant that is directly related to the original A-constant.

Equiconvex spherical lenses have the unique property that the principal planes move very little relative to the edge of the lens throughout an exemplary power range of zero to 30D. Thus, the A-constant is nearly constant over that range of power, as will be understood by the person skilled in the art.

Biconvex lenses, however, have A-constants that vary over the power range due to the different radii of curvature of the posterior and anterior surfaces. Spherical aberration, inherently present in all spherical lenses, also affects the A-constant.

Figure 17:
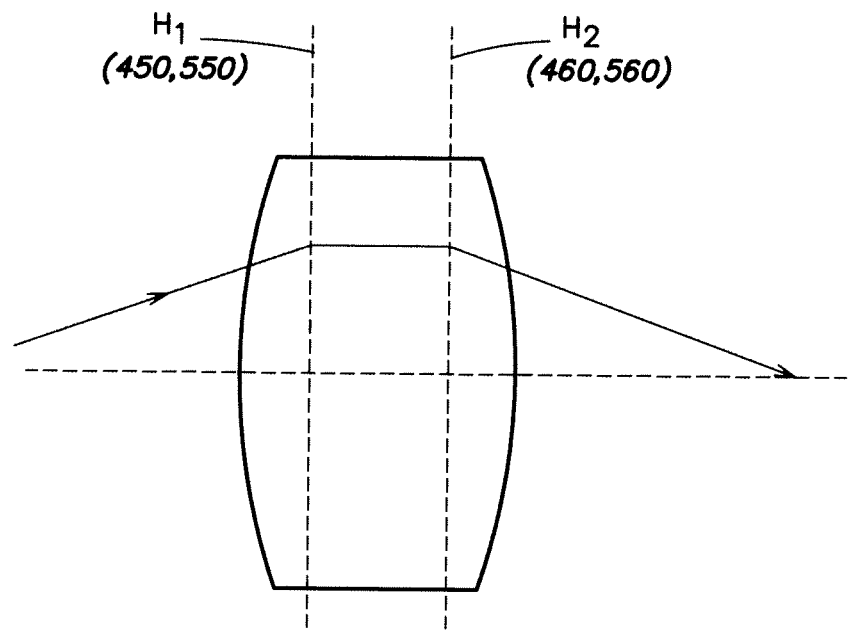
FIG. 17 is a schematic drawing of an equiconvex spherical thick lens illustrating the principal planes of the lens.
Figure 18:
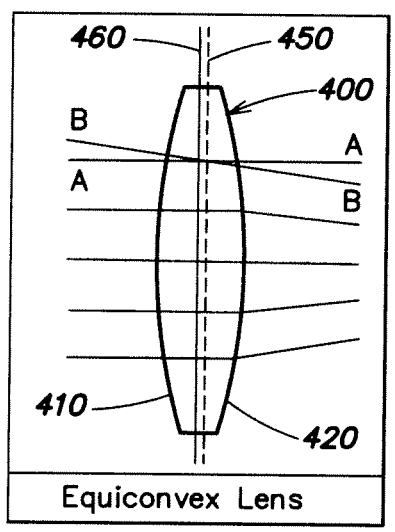
FIG. 18 is a schematic drawing of an equiconvex spherical IOL illustrating the location of the principal planes with respect to the edges of the lens.
Figure 19:
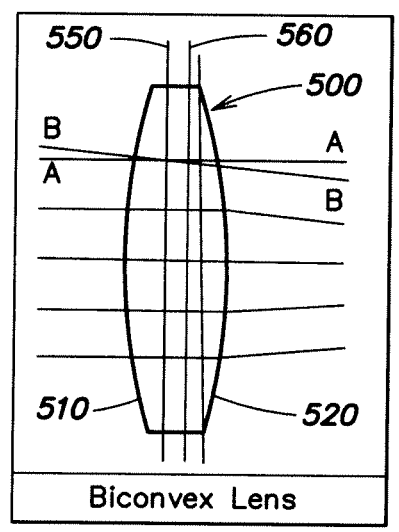
FIG. 19 is a schematic drawing of an biconvex spherical IOL illustrating the location of the principal planes as a function of lens surface radius.

FIG. 17 shows a thick lens that has first and second principal planes, H1, H2. The principal planes of a lens are hypothetical planes where all lens refraction is considered to occur. For a given lens, the principal planes are fixed and do not depend on the object position. As is known, the location of the principal planes with respect to each other and with respect to the edge location of a lens can be changed by changing the surface shape of the lens. FIGS. 18 and 19, respectively, show an equiconvex spherical lens 400 and a biconvex spherical lens 500. Lens 400 has first and second principal planes, 450, 460 that virtually coincide. Lens 500 has first and second principal planes 550, 560 that are separated from each other. For the equiconvex spherical lens 400, the principal planes 450, 460 are near the center of the lens because the anterior surface 410 and the posterior surface 420 have the same radius of curvature. As the radii of curvature change, the principal planes will remain substantially in the center of the lens. Thus, the A-constant of an equiconvex spherical lens remains virtually (but not entirely) constant over a wide range of powers. For the biconvex lens 500, as the radius of curvature of the posterior surface 520 increases relative to that of the anterior surface 510, the second principal plane 560 moves in the anterior direction. This will cause a change in the A-constant unless both radii of curvature are changed equally. As a result, each power of a lens and a family of biconvex spherical lenses may have a different A-constant. As referred to above, this is undesirable for the manufacturer and the physician.

Figure 24:
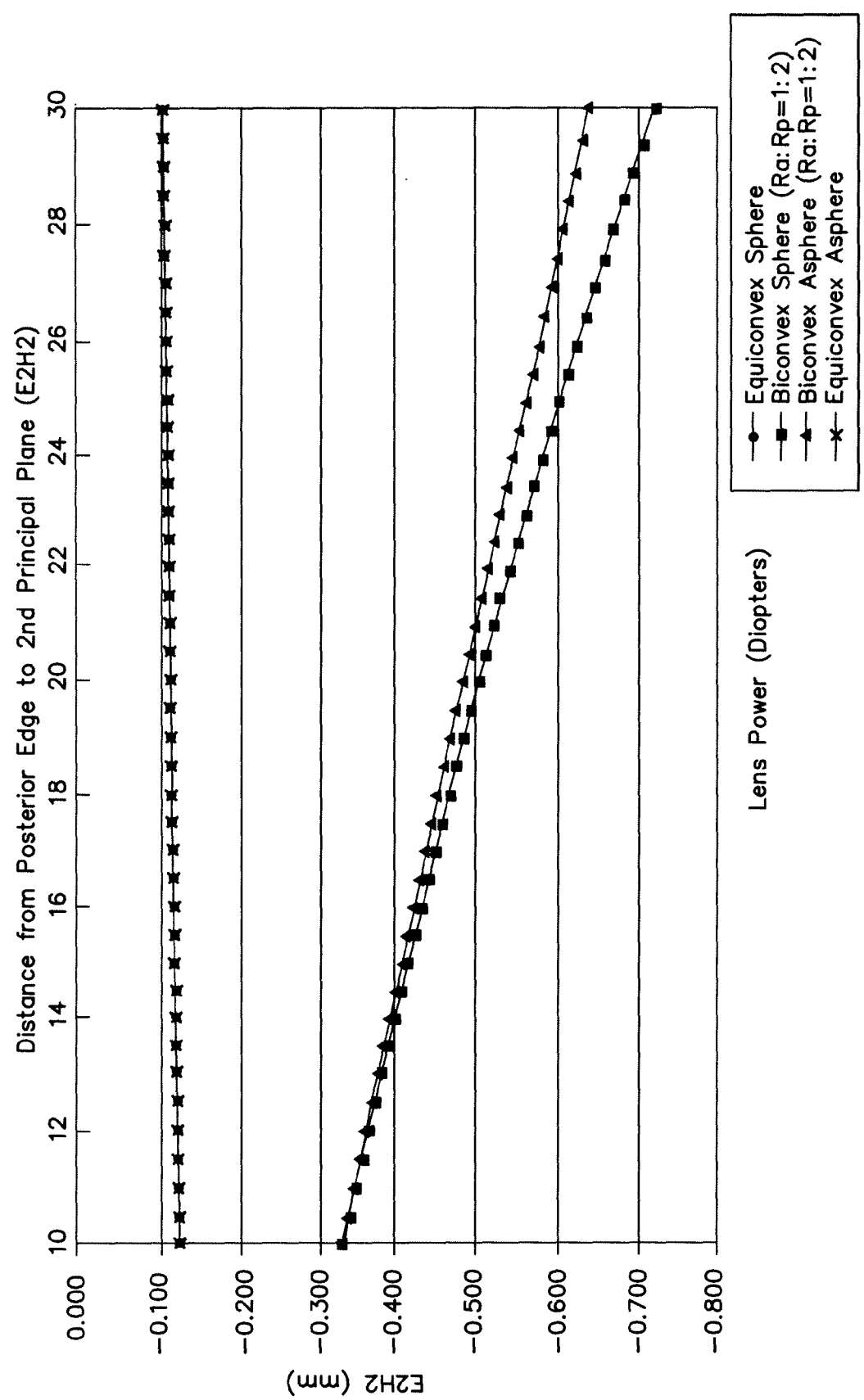
FIG. 24 is a graph of comparative experimental results of principal plane movement in a lens as a function of lens power for prior art spherical lenses and aspheric IOLs according to embodiments of the invention.

A computer-generated experiment was made to compare the difference in the shift of the second principal plane for an equiconvex spherical lens, a biconvex spherical lens, a biconvex aspheric lens and an equiconvex aspheric lens for powers from 10D to 30D. FIG. 20 shows the relevant measurement parameters for the equiconvex spherical lens; FIG. 21 shows the relevant lens parameters for the biconvex spherical lens; FIG. 22 shows the relevant lens parameters for the biconvex aspheric lens with anterior and posterior conic constants of (minus)-0.97799; and FIG. 23 shows the relevant lens parameters for the equiconvex aspheric lens with anterior and posterior conic constants of −1.16133. Comparative experimental results are shown in FIG. 24. In all of the cases, the index of refraction of the lens was 1.427 and the index of refraction of the surrounding medium (i.e., the aqueous) was 1.336. In each table of FIGS. 20-23, the anterior apical radius of curvature, the posterior apical radius of curvature, center thickness, edge thickness and the difference between the position of the second principal plane and the second edge (E2, H2) are listed for each paraxial power. The last column in each table shows the cumulative effect on power due to the location of the second principal plane and spherical aberration.

It can be seen from the figures that both the spherical and aspheric equiconvex lenses show little or no change in the distance between the second edge and the second principal plane. In contrast, the spherical and aspheric biconvex lenses show more dramatic changes in the location of the second principal plane with respect to the second edge. As the second principal plane H2 moves more anteriorly, the apparent power of the lens in the eye increases and vice versa. For example, if there are two lenses, A and B with the same measured power of 20D, but H2 is shifted 0.2 mm anteriorly for A relative to B, then the true power of A will appear to be 0.26D stronger than B.

Figure 25:
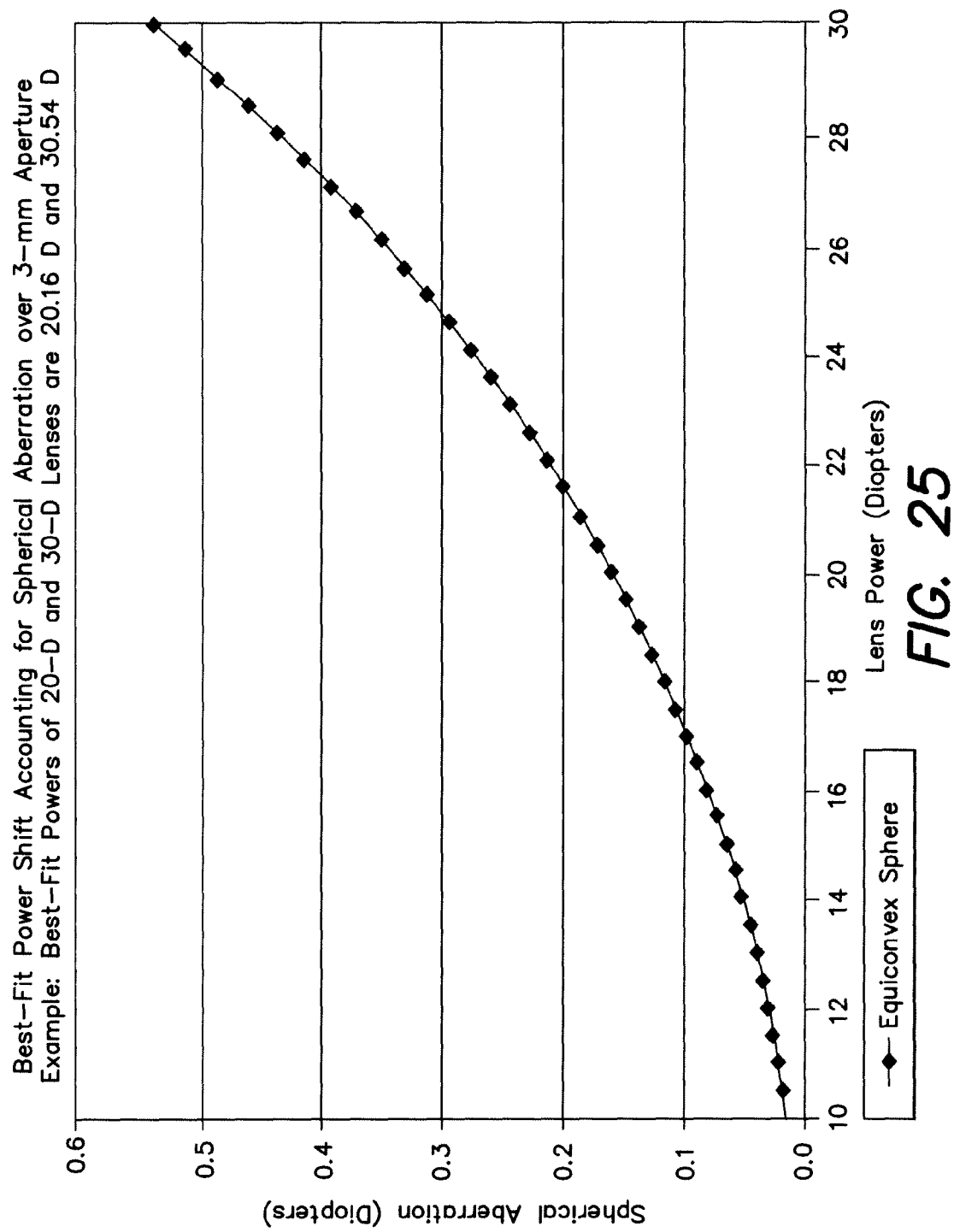
FIG. 25 is a graph showing spherical aberration as a function of lens power for a prior art spherical IOL.
Figure 26:
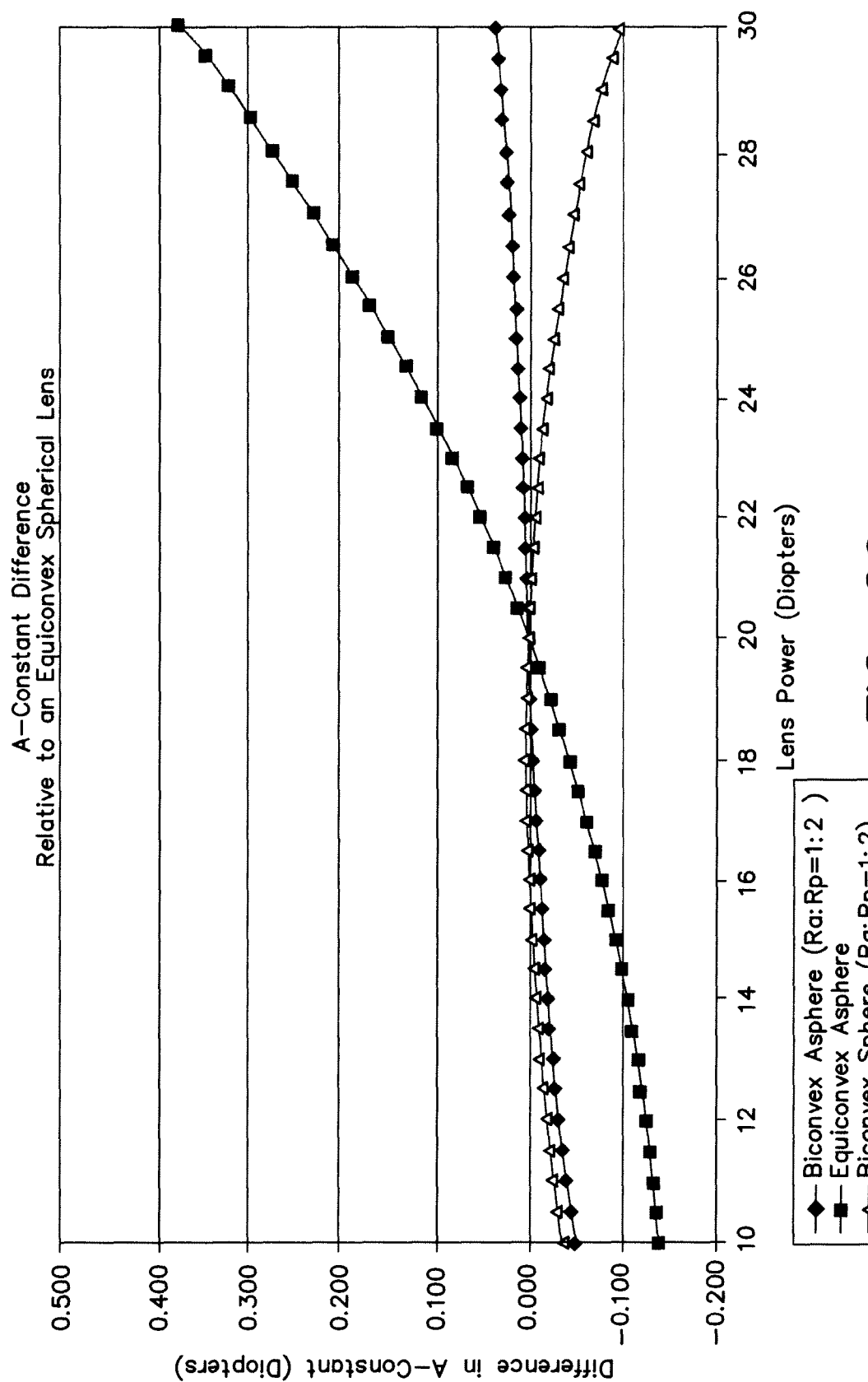
FIG. 26 is a comparative graph illustrating the balancing of spherical aberration and radii asymmetry as a function of lens power.

It should be noted that an aspheric lens having no inherent spherical aberration will not have the same A-constant as a spherical lens with the same lens shape factor. The effect of the spherical aberration on the A-constant is shown in FIG. 25, which illustrates that the A-constant of the equiconvex spherical lens is not necessarily constant at large powers. The effects of spherical aberration and asymmetry between the anterior and posterior radii can be set to off-set or balance the changes in the A-constant, such that the in-vivo power of the aspheric lens will be similar to that of a parent spherical lens throughout the range of powers. In other words, an aspheric biconvex IOL can mimic the A-constant features of a spherical equiconvex IOL and provide virtually no difference between a biconvex aspheric lens and equiconvex IOL. FIG. 26 illustrates the balancing of spherical aberration and radii asymmetry in order to minimize the difference in A-constant throughout the range of lens powers relative to an equiconvex design. The biconvex aspheric lens is fashioned to have even less variance in A-constant over the full range of powers. Since the A-constant of the biconvex aspheric lens can be controlled, a manufacturer may set the A-constant to be identical to the variation in the A-constant of the equiconvex lens. In effect, the A-constant of the biconvex aspheric lens can be controlled to mimic or approximate the A-constant of any known IOL.

Another embodiment of the invention is directed to a method for designing a family of aspheric IOLs, the family including a plurality of individual aspheric IOLs each having a lens power and a different value of inherent spherical aberration, each characterized by a lens constant and a lens shape factor. The method involves the steps of determining a lens constant that is the same for each of the plurality of IOLs, and providing the lens shape factor that is different for each of the plurality of IOLs. The spherical aberration for the family may reasonably range from between about −2.0 microns to 1.0 micron over a 6 mm pupil aperture. Over this range, an aspect of the design method contemplates designing lenses in groups having inherent negative spherical aberration, inherent positive spherical aberration and zero inherent spherical aberration. An aspect of the design method also includes designing at least one of the group of IOLs to induce between about −0.13 micron to −0.07 micron of spherical aberration to a converging wavefront propagating from a focusing optical element such as a cornea having a focusing power of between 37D to 49D. In another aspect, the design method contemplates designing an IOL that induces substantially no spherical aberration to a converging wavefront propagating from a focusing optical element such as a cornea.

In accordance with the family embodiments described above, each of the pluralities of IOLs is an aspheric child-lens designed such that its lens constant is the same as the lens constant of a spherical parent-lens that is not one of the family of IOLs.

Figure 27:
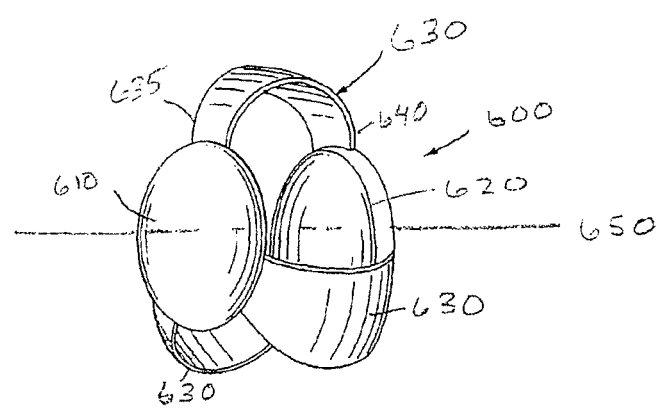
FIG. 27 is a perspective illustration of a multi-component accommodating intraocular lens (A-IOL) according to an exemplary embodiment of the invention.

Another embodiment of the invention is directed to a multi-component accommodating intraocular lens (A-IOL). An exemplary A-IOL 600 is illustrated in FIG. 27. The design of exemplary A-IOL 600 is patterned after what is known in the industry as the Safarazi accommodating IOL (See, e.g., U.S. Pat. Nos. 5,275,623, 6,423,094 and 6,488,708, the disclosures of which are hereby incorporated by reference in their entireties). The A-IOL 600 includes an anterior lens 610, a posterior lens 620 and at least one biasing element 630 coupling the anterior lens component and the posterior lens component. In FIG. 27, the A-IOL 600 is shown having three biasing elements 630. The biasing elements 630 are also known in the art as haptics. As shown, each biasing element is coupled to a portion of the periphery of the anterior lens (or a lens frame) 610 at an anterior region 635 of the biasing element and to a portion of the periphery of the posterior lens (or a lens frame) 620 at a posterior region 640 of the biasing element. A primary function of the biasing element(s) 630 is to allow the anterior lens 610 to translate along the optical axis 650 of the A-IOL relative to the posterior lens 620.

Figure 28A:
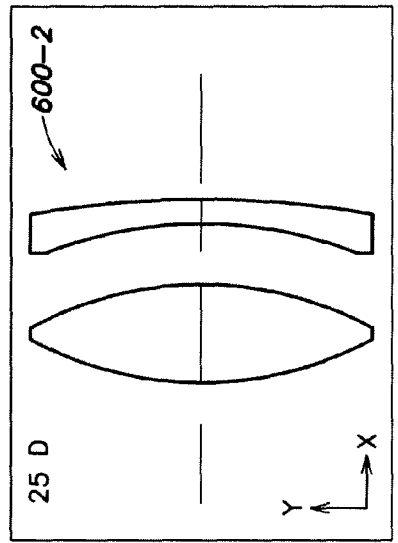
FIGS. 28A-28D are cross sectional schematic diagrams of four member A-IOLs of an A-IOL family according to an embodiment of the invention.
Figure 28B:
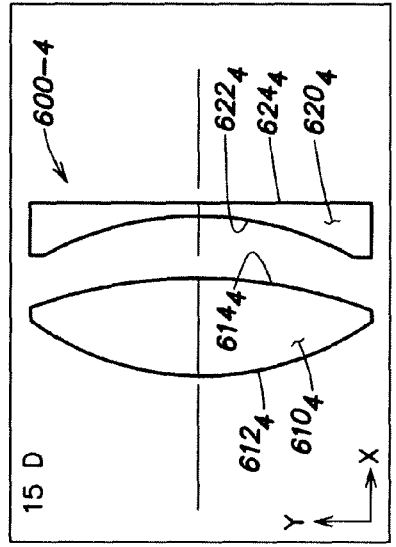
Figure 28C:
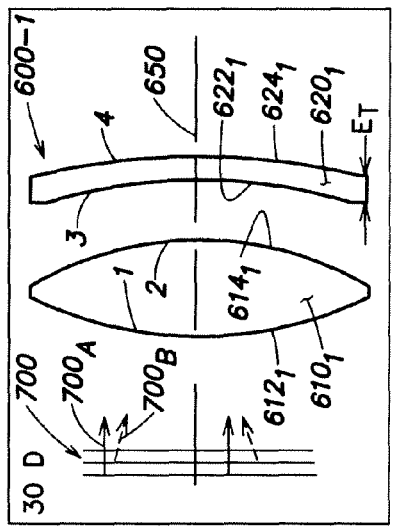
Figure 28D:
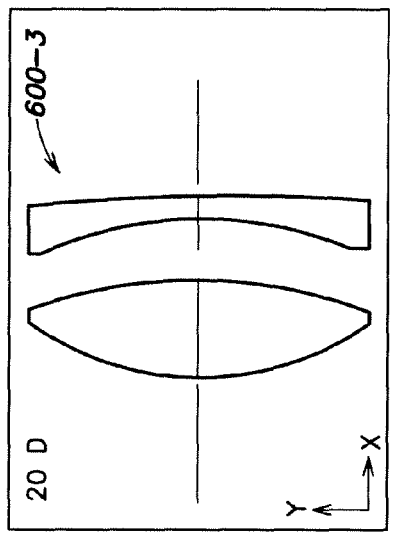

FIG. 28A is a cross sectional diagram of an exemplary A-IOL 600-1 as shown in FIG. 27 including the anterior lens 610$_1$ and the posterior lens 620$_1$. The biasing element(s) 630 are not shown. A-IOL 600-1 has an exemplary power of 30D. As will be further described below, A-IOL 600-1 is a representative member A-IOL of an exemplary A-IOL family comprising A-IOLs 600-1, 600-2, 600-3 and 600-4. In FIG. 28A, the lenses are at an arbitrary separation distance that is not relevant for an understanding of the present embodiment of the invention. Anterior lens 610$_1$ has an anterior surface 612$_1$ referred to herein as the first surface (1) of the A-IOL, and a posterior surface 614$_1$ referred to herein as the second (2) surface of the A-IOL. Posterior lens 620$_1$ similarly has an anterior surface 622$_1$ referred to herein as the third (3) surface of the A-IOL and a posterior surface 624$_1$ referred to herein as the fourth (4) surface of the A-IOL. The terms anterior and posterior refer to lenses and/or surfaces that are towards the front of the eye and towards the rear of the eye, respectively. According to a particularly advantageous aspect of the present embodiment, the A-IOL is designed to introduce substantially no spherical aberration to a wavefront incident upon and passing through the A-IOL. In this aspect, at least one of the first, second, third or fourth surfaces of the A-IOL 600-1 is aspheric so as to impart a desired spherical aberration effect on the wavefront 700 that is incident upon and passing through the A-IOL 600-1. As a result of the at least one surface having a given asphericity, the A-IOL 600-1 is designed to impart substantially no residual spherical aberration to the wavefront 700 passing through the A-IOL.

According to an exemplary aspect of the embodiment, the A-IOL 600-1 is designed to have no inherent spherical aberration; that is, the A-IOL 600-1 will not introduce any spherical aberration to a plane wavefront 700$_A$ passing through the A-IOL. According to this aspect, both the anterior lens 610$_1$ and the posterior lens 620$_1$ will be free of inherent spherical aberration. Thus, at least one of the first and second surfaces 612$_1$, 614$_1$ and at least one of the third and fourth surfaces 622$_1$, 624$_1$ will be aspheric surfaces. The aspheric surfaces of the A-IOL 600-1 may be rotationally symmetric or non-rotationally symmetric aspheric surfaces. Alternatively, the anterior lens 610$_1$ may have a finite amount of spherical aberration and the posterior lens 620$_1$ will then have a substantially equal amount of inherent spherical aberration of opposite sign such that overall the A-IOL has zero inherent spherical aberration. According to another aspect in which the wavefront 700$_B$ incident upon the A-IOL is converging after being refracted, for example, by the cornea or an optical element of an optical system, the A-IOL 600-1, having at least one suitably designed aspheric surface, will introduce substantially no residual spherical aberration to the converging wavefront 700B passing through the A-IOL.

A related embodiment according to the invention is directed to a family of A-IOLs comprising a plurality (at least two) of member A-IOLs 600$_n$ as described above. As is well known in the art, each intraocular lens, whether an IOL, an accommodating IOL (single element) or an A-IOL (multi-element), is designed to provide a particular correcting power within a correcting power range. Conventional intraocular lenses are designed in differential power steps of 0.25 diopters (D). However, according to illustrative embodiments of the invention, the power differential between any two serial (i.e., sequential in power) member A-IOLs may be set to any constant value, e.g., 0.25D to 15.0D, over the given power range, to constitute a family.

FIGS. 28A-28D illustrate four respective member A-IOLs 600-1, 600-2, 600-3 and 600-4 of an exemplary A-IOL family. The family may have more than four member A-IOLs (at least two) depending upon the dioptric power range of the family and the power differential between sequential member A-IOLs. As illustrated, A-IOL 600-1 has a correcting power of 30D; A-IOL 600-2 has a correcting power of 25D; A-IOL 600-3 has a correcting power of 20D and A-IOL 600-4 has a correcting power of 15D. All surfaces of the member A-IOLs are smooth, continuous type refracting surfaces.

Figure 31:
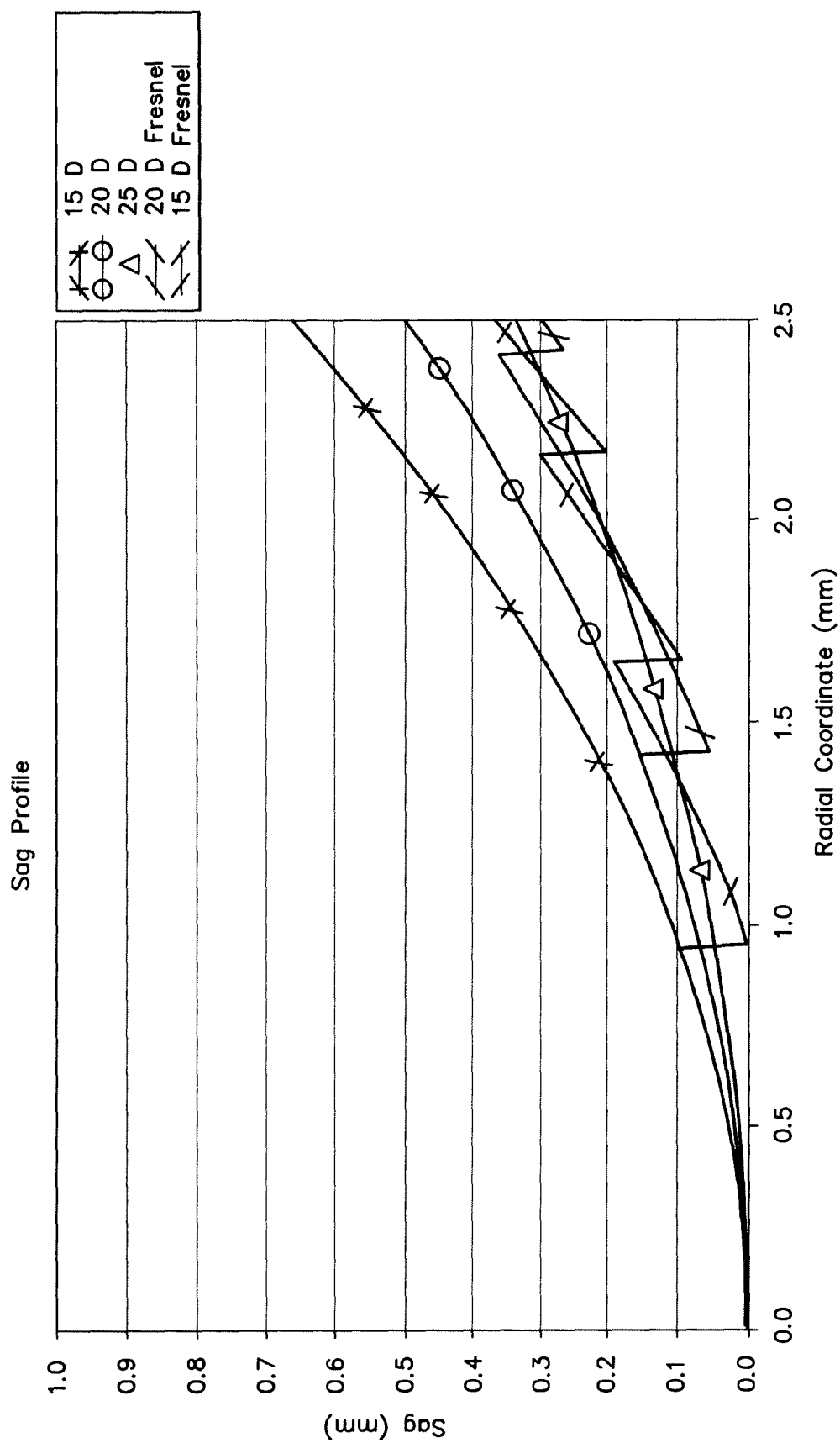
FIG. 31 is a graphical view showing comparative data between A-IOLs having continuous type refracting surfaces and discontinuous (e.g., Fresnel) surfaces according to an embodiment of the invention.
Figure 32B:
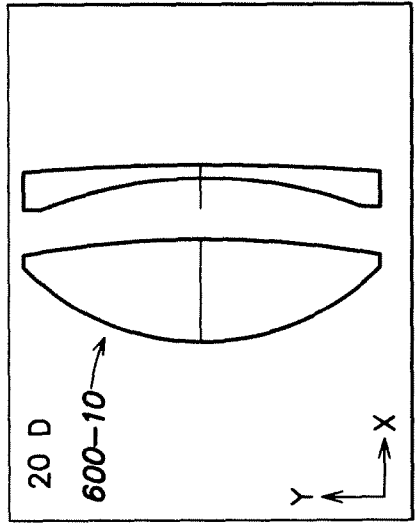
FIGS. 32A-32D are cross sectional schematic diagrams of four member A-IOLs of another exemplary A-IOL family according to an embodiment of the invention.
Figure 32D:
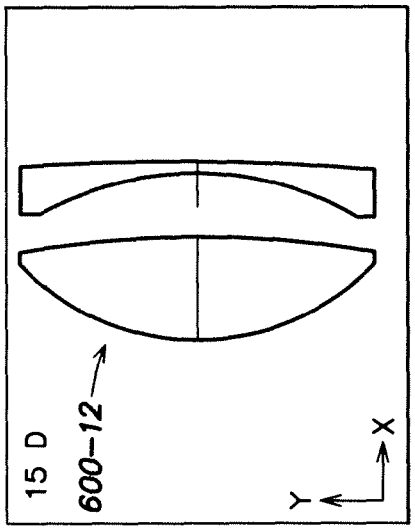
Figure 32A:
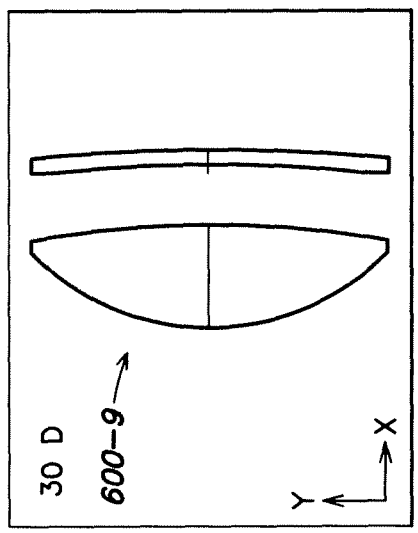
Figure 32C:
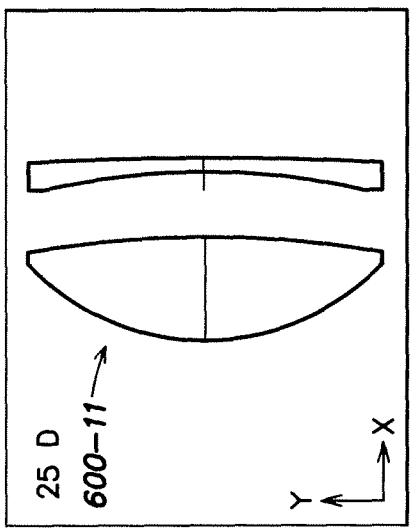
Figure 34B:
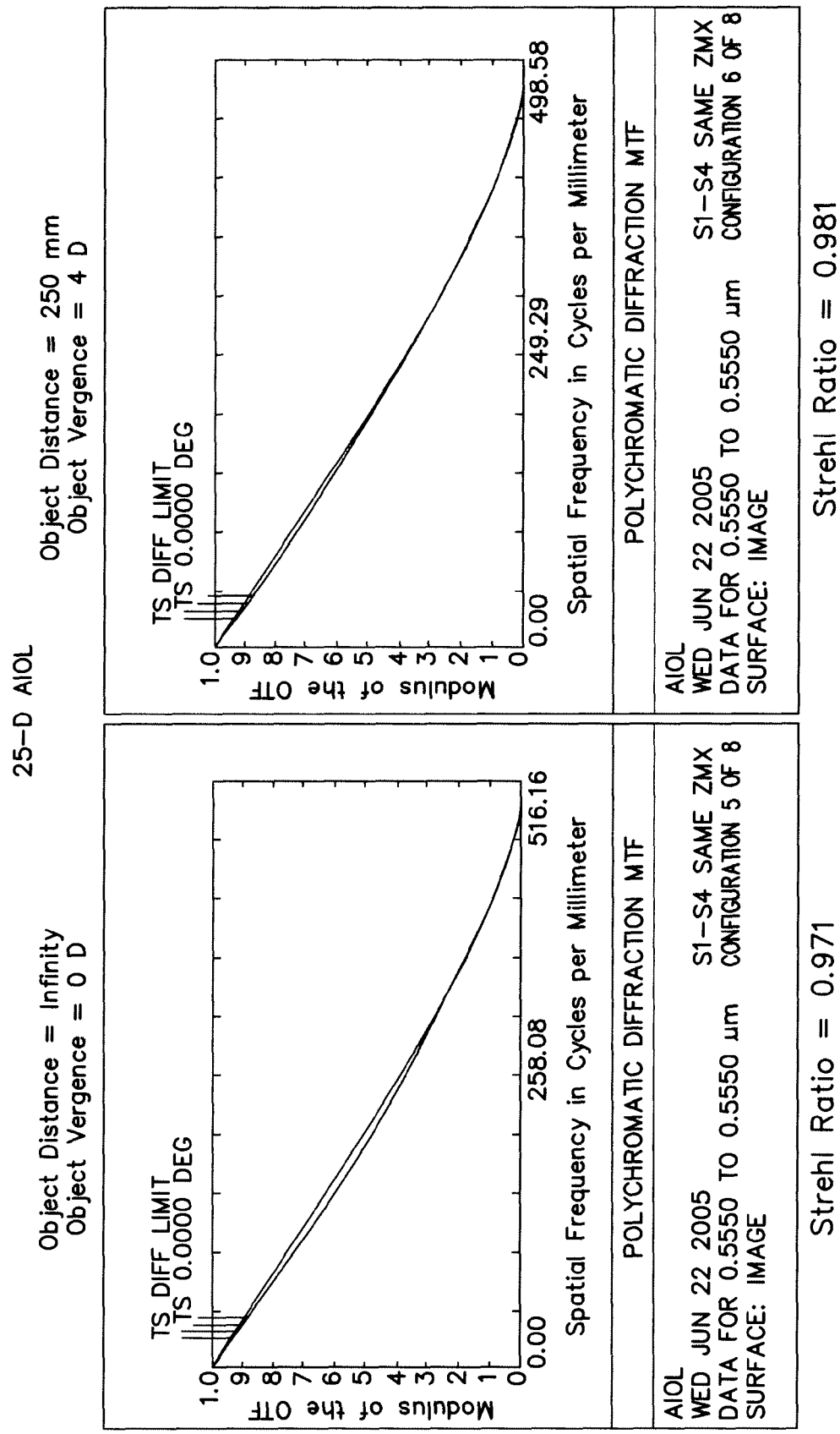
Figure 34C:
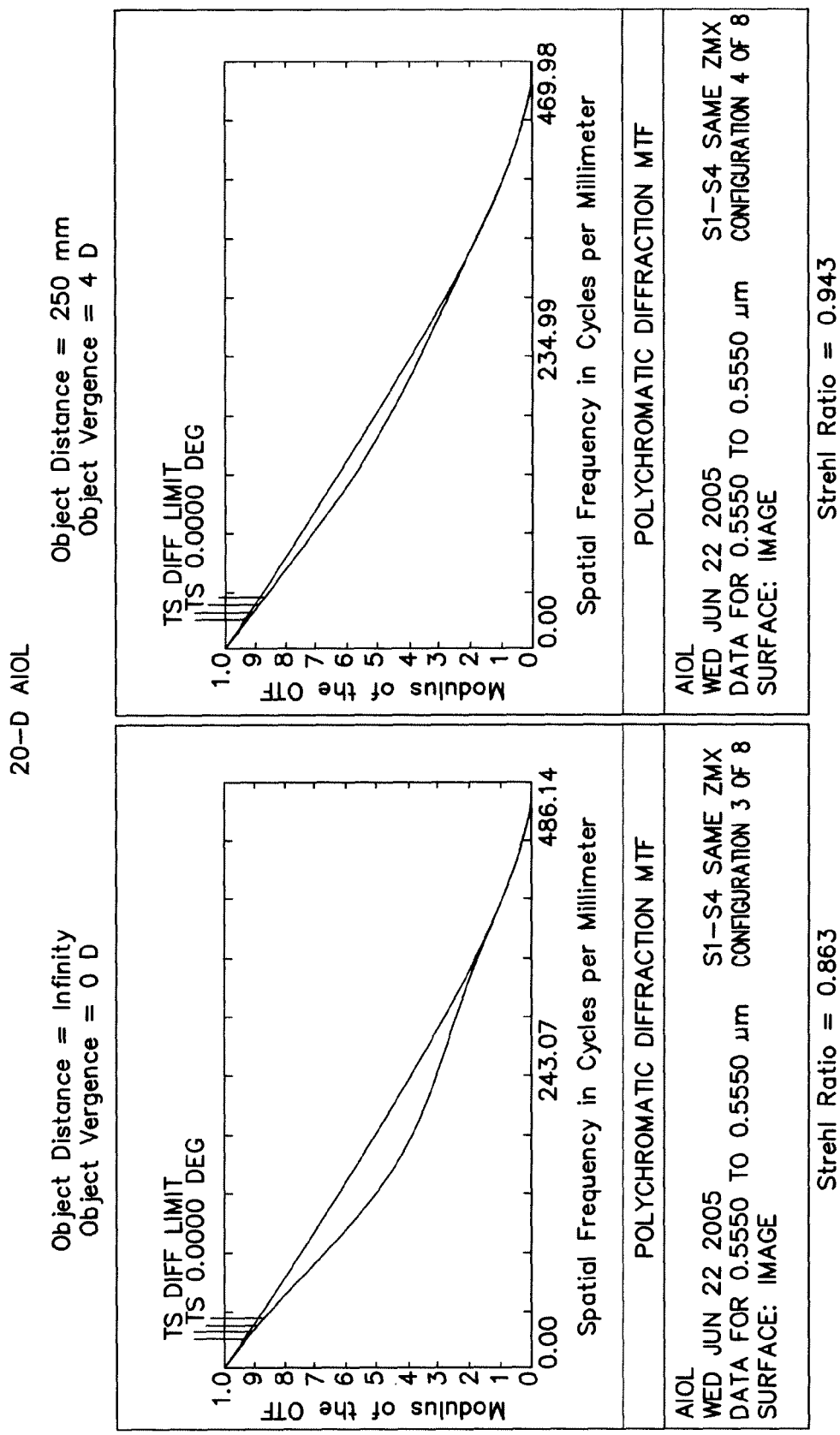
Figure 34D:
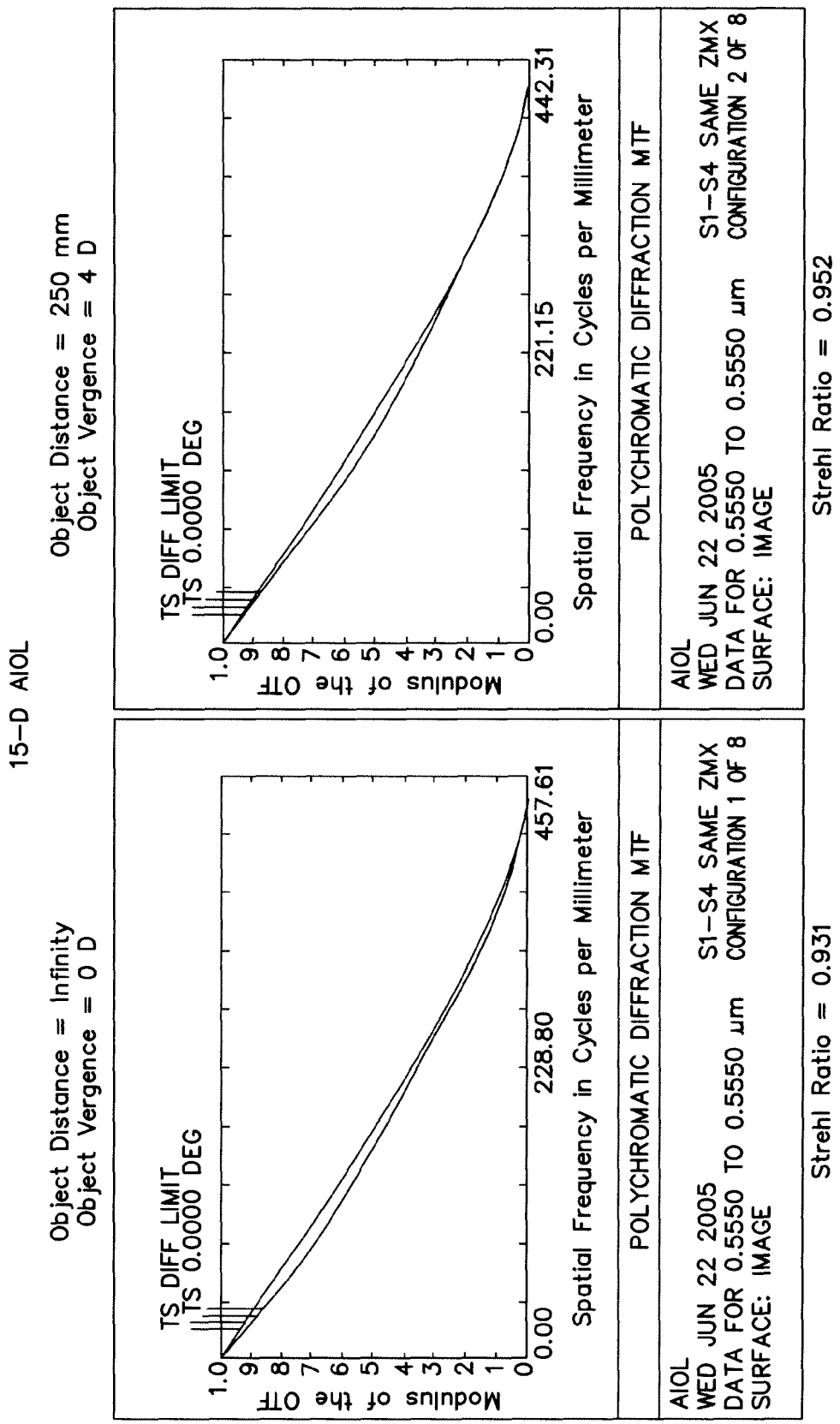
Figure 35A:
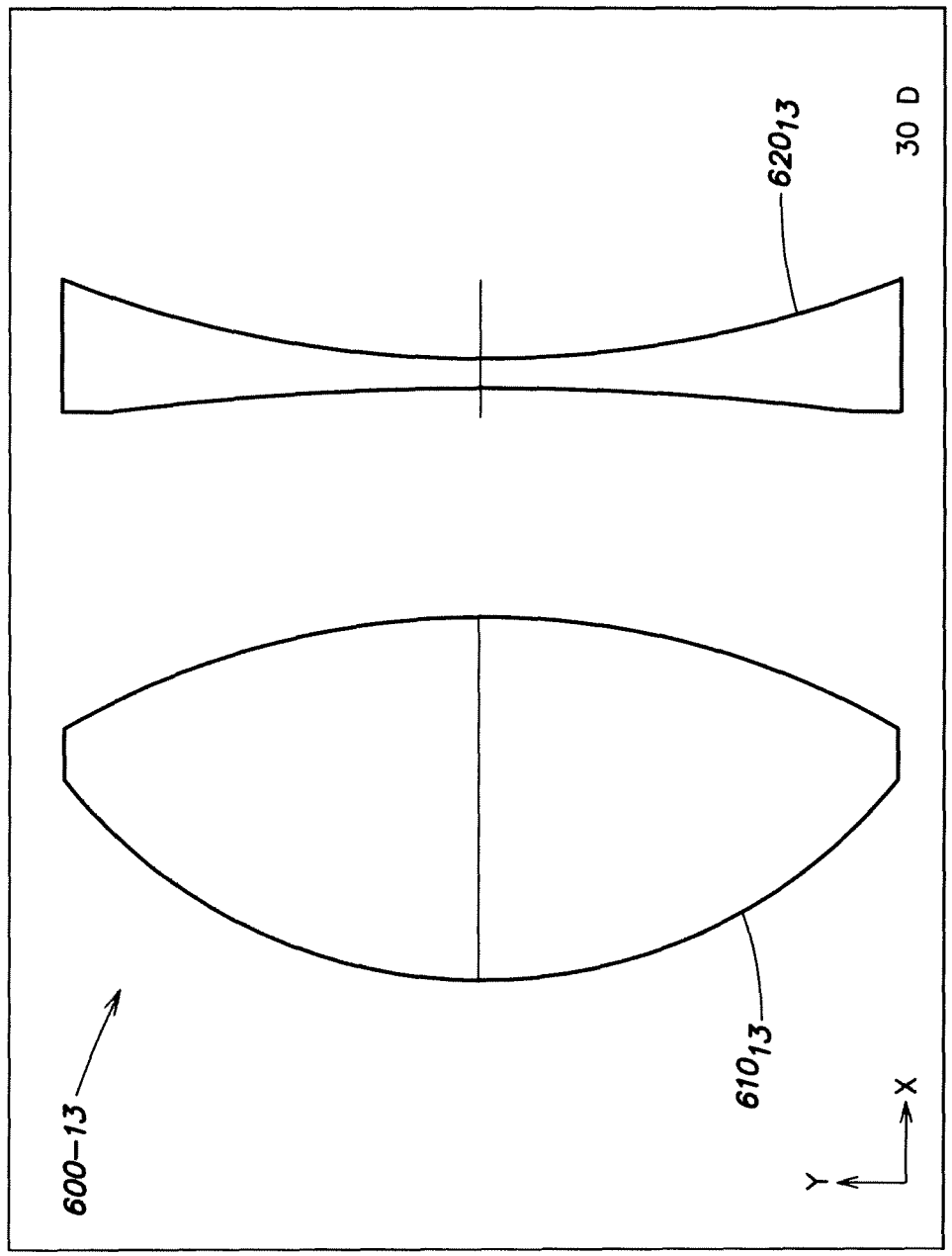
FIGS. 35A-35D are cross sectional schematic diagrams of four member A-IOLs of another exemplary A-IOL family according to an embodiment of the invention.
Figure 35B:
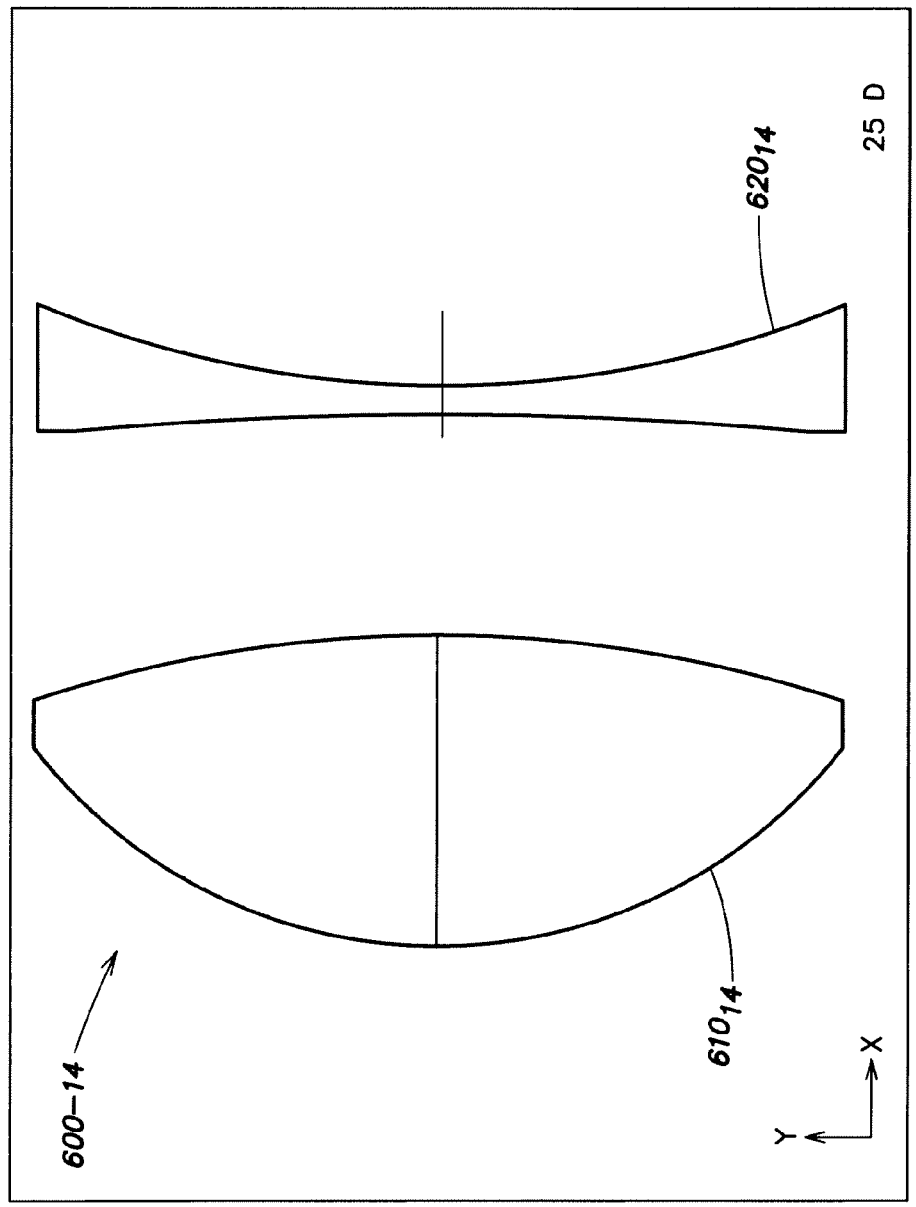
Figure 35C:
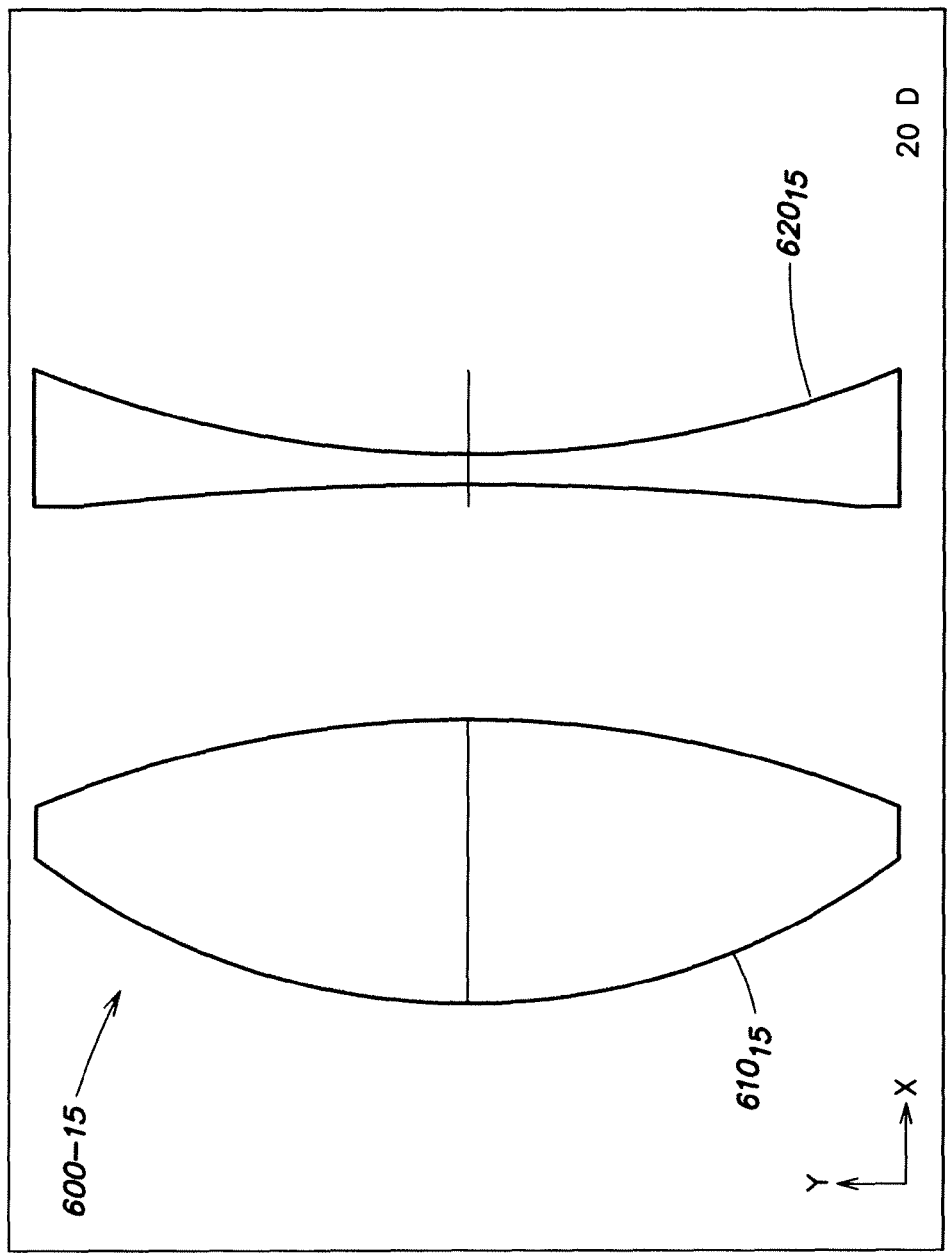
Figure 35D:
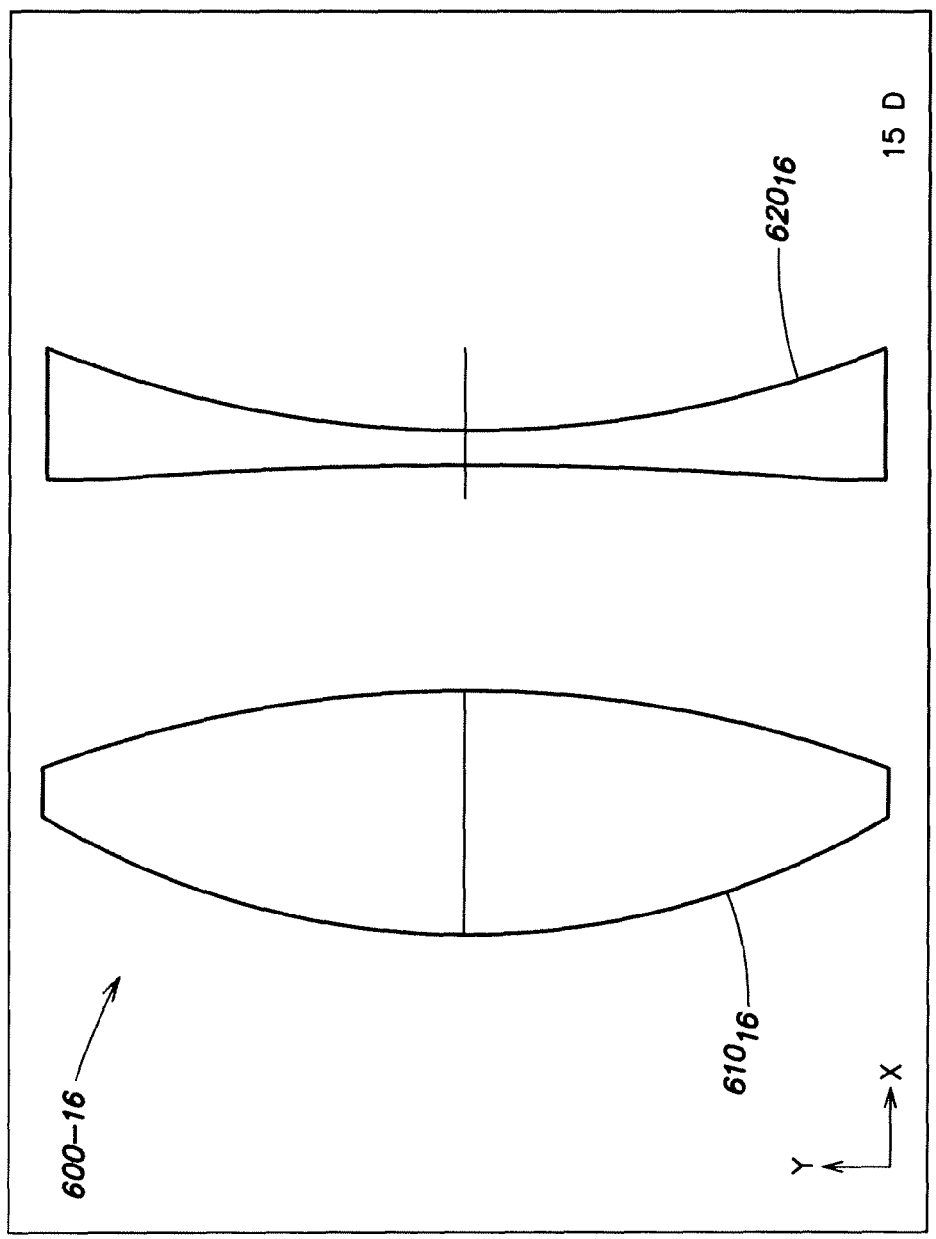

FIGS. 29A-29D, respectively, are tables that contain selected physical and optical parameter data of the member A-IOLs 600-1 through 600-4. As the table entries indicate, only surface (1) of each member A-IOL is aspheric. Moreover, despite a relatively constant volume of lens material for each member A-IOL, the edge thickness $E_T$ of the posterior component of each member A-IOL changes, thus changing the overall lens size. Generally, the dimension $E_T$ will increase as a function of increasing negative optical power of the posterior lens component. A relatively large variation in the physical dimension of member A-IOLs over the full dioptic range of the A-IOL family may limit the use of a single lens injector device for injecting all member A-IOLs of the family. This may necessitate the use of accessory components at increased cost. To address this concern, the edge thickness or other physical parameters including, but not limited to, lens volume, lens mass, cross sectional area and shape of each member A-IOL may be controlled. Thus, according to another exemplary aspect as illustrated in FIGS. 30 and 31, each of the representative member A-IOLs 600-5, 600-6, 600-7 and 600-8 are characterized by having constant edge thickness values. This may be achieved by replacing at least one of the continuous type refracting surfaces 622$_n$, 624$_n$ with a diffractive, a Fresnel or other discontinuous type of optical surface.

FIG. 30 is an Excel spreadsheet showing comparative optical surface (3) SAG data between 15D, 20D, 25D and 30D continuous type refracting surface member A-IOLs (columns 2-5) and 15D and 20D Fresnel (discontinuous) surface member A-IOLs (columns 6-7) as a function of increasing radial distance of the optical zone of the lens from 0.0 to 2.5 mm (column 1). In this illustrative embodiment, surfaces (1) and (4) remain unchanged, as described in more detail below with reference to A-IOLs 600-9, 600-10, 600-11 and 600-12 illustrated in FIGS. 32A-D and 33A-D. In the instant embodiment, the mean curvature of surface (3) for the 15D and 20D A-IOLs was set similar to the surface (3) curvature of the 25D A-IOL. This was motivated by the ideal maximum lens thickness parameter exhibited by the 25D A-IOL. For lens powers greater than 25D, surface (3) is already sufficiently flat, so there is no need to make the surface discontinuous (i.e., diffractive, Fresnel, etc.). As a general rule, a Fresnel surface is less desirable than a smooth, continuous type refracting surface because it is more difficult to make and may exhibit dysphotopic effects.

FIG. 31 graphically shows the comparative surface shapes of surface (3) of a 15D, 20D and 25D continuous type (smooth) refracting surface A-IOL and a 15D and 20D Fresnel (discontinuous type) surface A-IOL. If FIG. 31 is viewed with the coordinate origin (0,0) at lower right position (radial coordinate axis up and Sag axis left), the curves illustrate the concave profiles of surface (3) for the lenses. It can be seen that the Fresnel geometry provides a relatively constant posterior lens thickness of about 0.3 to 0.4 mm at the 2.5 mm radial edge of the optical zone. Although the Fresnel steps are shown in 100μ increments, this value can be adjusted to customize the design. It will be appreciated by a person skilled in the art that the potential and actual benefits derived from the replacement of a continuous type refracting surface by a diffracting, Fresnel or other discontinuous type surface, for example, are not dependent upon the spherical or aspherical characteristics of the A-IOL. As such, the benefits obtainable by spherical aberration control as described herein as well as the benefits associated with control of the physical parameters of an A-IOL may be realized independently or cumulatively.

In another illustrative aspect described with reference to FIGS. 32A-32D and 33A-33D the member A-IOLs 600-9, 600-10, 600-11 and 600-12 are designed such that the respective radius and conic constant values of the first and fourth surfaces of each member A-IOL remain constant over the full power range of the family. As such only at least one of the second and third surfaces of each member A-IOL will change to change the power value of each respective member A-IOL. Advantages associated with this embodiment include molding process and apparatus efficiencies. For example, the mold components for each member A-IOL currently include two mold halves for surfaces (1) and (4) and a paddle component including two diamond-turned surfaces corresponding to surfaces (2) and (3). Four different precision surfaces are thus required for each member A-IOL. This is costly and requires a significant time investment. According to the instant embodiment, the need to supply different mold halves for surfaces (1) and (4) for each member A-IOL is eliminated. FIGS. 34A-34D show MTF curves and Strehl ratio values for each of the member A-IOLs of FIGS. 32A-32D, respectively, between an accommodating range of 0D and 4D. The data show that the A-IOLs have near diffraction-limited performance. It is to be further appreciated by a person skilled in the art that the lens component molding apparatus and process efficiencies referred to and obtainable by keeping the first and fourth surface parameters constant apply equally to A-IOLs in which all surface conic constant values are zero (spherical surfaces) as well as to those having one or more aspheric surfaces as in the illustrative embodiments.

According to another A-IOL embodiment, a representative A-IOL (and each member A-IOL of a family) has a finite amount of inherent negative spherical aberration that is less than an amount of spherical aberration required to balance the inherent positive spherical aberration produced by the human cornea. In an exemplary aspect, each member A-IOL will have between (−)0.23μ to (−)0.08μ of inherent spherical aberration, assuming an average cornea having about (+)0.28μ of spherical aberration over a 6 mm pupil diameter. In a particular exemplary aspect, the representative A-IOL has an inherent amount of negative spherical aberration that mimics the spherical aberration of a healthy, natural crystalline lens in a relaxed state: i.e., between about (−)0.13μ to (−)0.07μ of spherical aberration and, more particularly, about (−)0.1μ of spherical aberration, induced in a converging wavefront propagating from the cornea thru the A-IOL. According to an aspect, the representative A-IOL will have an amount of inherent negative spherical aberration that is less than a corresponding amount of inherent positive corneal spherical aberration that is an average value for a statistically significant population of subjects. According to another aspect, at least one of the anterior lens component and the posterior lens component will be free of inherent spherical aberration while the other lens component will have the inherent negative spherical aberration of the A-IOL. In a particular aspect, the anterior lens component, which typically is the lens component that translates in relation to the posterior lens component in the accommodating process, will be the component that is designed to be free of inherent spherical aberration. Thus, misalignment or tilt of the anterior lens component will not induce other aberrations such as coma, for example, as would occur if the anterior lens component had a finite amount of inherent spherical aberration.

A related embodiment according to the invention is directed to a family of A-IOLs, including at least two member A-IOLs, wherein each of the member A-IOLs has an inherent amount of negative spherical aberration as described immediately above, and a different power value within the power range of the A-IOL family. Each of the member A-IOLs will have at least one aspheric surface. At least some of the member A-IOLs of the family may have a posterior lens component of a diffractive or Fresnel optical type so as to keep a desired physical lens parameter constant over the A-IOL family power range, as described above. In another aspect, the optical parameters of the first and fourth surfaces of each member A-IOL of the family will remain constant over the power range of the A-IOL family, as described above.

Another embodiment according to the invention is directed to member A-IOLs and an A-IOL family characterized by an accommodative power amplitude that varies as a function of A-IOL optical power. In the exemplary A-IOL embodiments described above, the positive power of the anterior lens element remains substantially constant (e.g., +32D) for all member A-IOL power values. Thus the power of the posterior lens element is varied to achieve the desired member A-IOL power. In an illustrative aspect, the accommodative amplitude per millimeter of translational anterior lens movement is the same for all member A-IOL powers; that is, 2.2 D/mm. For a two-optic lens system, accommodative amplitude increases as a function of increasing lens power of the anterior element. For example, the illustrative accommodative amplitude of 2.2 D/mm for a 20D A-IOL (+32D anterior element, −12D posterior element) would increase to an exemplary value of 4.5 D/mm for an anterior element power value of 50D. However, as mentioned above, since lens size (e.g., thickness, volume, etc.) generally increases with increasing negative power of the posterior lens element, the necessary (−)30D power of the posterior lens element for an A-IOL power of 20D would result in a relatively massive and undesirable lens size. According to the instant embodiment, the power of the posterior element is kept relatively constant while the power of the anterior element is varied to achieve the desired member A-IOL power. Accordingly, the accommodative amplitude per millimeter of anterior lens translational movement will increase as a function of increasing member A-IOL power. In an illustrative aspect, the power of the posterior element may be between −5D and −20D. The power of the anterior element will vary to achieve the desired total power of the lenses. For example, if the posterior element power is −5D, then the anterior element could vary between +20D and +35D. If the posterior element power is −20D, then the anterior element could vary between +35D and +50D. FIGS. 35A-35D show schematic cross sectional views of exemplary member A-IOLs 600-13, 600-14, 600-15 and 600-16 having respective powers of 30D, 25D, 20D and 15D. Corresponding FIGS. 36A-36D list lens parameter data for each of the illustrated member A-IOLs. As illustrated in FIGS. 35A-35D and 36A-36D, the posterior elements $620_{13}$, $620_{14}$, $620_{15}$ and $620_{16}$ retain a constant size and shape while anterior elements $610_{13}$, $610_{14}$, $610_{15}$ and $610_{16}$ vary over the power range (15D to 30D) of the exemplary A-IOL family. The resulting accommodative amplitude per millimeter of anterior lens translational movement for each of the member A-IOLs becomes 2.10 D/mm, 2.50 D/mm, 3.00 D/mm and 3.44 D/mm, respectively. In a practical aspect, the power of either element would not remain strictly constant throughout the power range of the A-IOL family, but would in all likelihood vary as necessary to achieve optimum optical quality and relatively uniform lens cross-sectional area and volume. In an aspect, all lens surfaces may be spherical. Alternatively, at least one of the surfaces may be aspheric as described above.

According to all of the exemplary A-IOL embodiments described above, the full power range of the family will advantageously range between 30D and (−)15D in selected power increments not limited to the exemplary member A-IOLs described herein above.

The foregoing description of the preferred embodiments of the invention have been presented for the purposes of illustration and description. It is not intended to be exhaustive or to limit the invention to the precise form disclosed. Many modifications and variations are possible in light of the above teaching. It is intended that the scope of the invention be limited not by this detailed description but rather by the claims appended hereto.

I claim:

1. A family of aspheric IOLs, comprising:
a plurality of individual aspheric IOLs each having a same lens power value and a different value of inherent spherical aberration (SA), wherein each of the lenses is characterized by a lens constant that is the same for the plurality of lenses, further wherein each lens has a lens shape factor that is different for the plurality of lenses.

2. The family of IOLs of claim 1, wherein the plurality of IOLs consists of any two or more individual IOLs.

3. The family of IOLs of claim 1, wherein each of the plurality of IOLs is a childlens whose lens constant is the same as the lens constant of a spherical parent-lens that is not one of the family of IOLs.

4. The family of IOLs of claim 1, wherein the value of inherent spherical aberration is in the range of $-2.0\mu \leq SA \leq 1.0\mu$ over a 6mm pupil aperture.

5. The family of IOLs of claim 1, wherein the family of IOLs comprises at least one IOL in a first group having a value of inherent spherical aberration (SA) in the range of $-2.0\mu \leq SA < 0\mu$ over a 6mm pupil aperture, at least one IOL in a second group having a value of inherent spherical aberration substantially equal to zero, and at least one IOL in a third group having a value of inherent spherical aberration (SA) in the range of $0 < SA \leq 1\mu$ over a 6mm pupil aperture.

6. The family of IOLs of claim 5, wherein at least one lens in the first group and at least one lens in the second group and at least one lens in the third group have equal values of lens power.

7. The family of IOLs of claim 1, wherein each of the lenses has a different lens power.

8. The family of IOLs of claim 1, further wherein each of the lenses has a paraxial power (P) in the range $+15D \leq P \leq +40D$.

9. The family of IOLs of claim 5, further comprising an optical system having an optical axis, the system including a focusing optical element having a focusing power between 37 diopters to 49 diopters and including a single one of the plurality of the first group of IOLs, said focusing optical element disposed on an object side of the one lens, wherein the lens induces no spherical aberration in a converging wavefront propagating from the focusing optical element through the lens.

10. The family of IOLs of claim 5, further comprising an optical system having an optical axis, the system including a focusing optical element and a single one of the plurality of the first group of IOLs, said focusing optical element disposed on an object side of the one lens, wherein the lens induces between about −0.13μ to −0.07μ of spherical aberration to a converging wavefront propagating from the focusing optical element through the lens, further wherein the spherical aberration amount is analogous to an amount of spherical aberration induced by a healthy natural crystalline lens in a relaxed state.

11. The family of IOLs of claim 10, wherein the lens induces about −0.1μ of spherical aberration to a converging wavefront propagating from the focusing optical element through the lens.

12. The family of IOLs of claim 1, comprising phakic IOLs, pseudophakic IOLs or a combination of phakic IOLs and pseudophakic IOLs.

13. The family of IOLs of claim 1, wherein each of the plurality of individual IOLs has a posterior surface and an anterior surface characterized by a respective conic constant, $k_p$, $k_a$, further wherein the ratio $k_a : k_p$ is constant for all radii.

14. The family of IOLs of claim 1, wherein each of the plurality of individual IOLs has a lens body made of silicone having an index or refraction (n) of between $1.40 \leq n \leq 1.60$.

15. The family of IOLs of claim 14, wherein each of the plurality of individual IOLs has a lens body made of silicone having an index or refraction (n) of about 1.43.

16. The family of IOLs of claim 1, wherein each of the plurality of individual IOLs has a lens body made of a hydrophilic acrylic having an index or refraction (n) of about 1.46.

17. The family of IOLs of claim 1, where each lens is labeled as having a same power as other lenses in the family.

18. The family of IOLs of claim 1, wherein each of the lenses has a paraxial power (P) in the range $-10D \leq P \leq +40D$.

* * * * *